(12) United States Patent
Shelton, IV et al.

(10) Patent No.: US 8,783,543 B2
(45) Date of Patent: Jul. 22, 2014

(54) TISSUE ACQUISITION ARRANGEMENTS AND METHODS FOR SURGICAL STAPLING DEVICES

(75) Inventors: Frederick E. Shelton, IV, Hillsboro, OH (US); John W. Willis, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 269 days.

(21) Appl. No.: 12/846,964

(22) Filed: Jul. 30, 2010

(65) Prior Publication Data

US 2012/0024935 A1 Feb. 2, 2012

(51) Int. Cl.
*A61B 17/068* (2006.01)

(52) U.S. Cl.
USPC .................................. 227/179.1; 227/180.1

(58) Field of Classification Search
USPC ......... 227/179.1, 180.1, 181.1; 606/151, 153, 606/219
See application file for complete search history.

(56) References Cited

U.S. PATENT DOCUMENTS

| | | |
|---|---|---|
| 3,166,072 A | 1/1965 | Sullivan, Jr. |
| 4,505,273 A | 3/1985 | Braun et al. |
| 4,506,671 A | 3/1985 | Green |
| 4,655,222 A | 4/1987 | Florez et al. |
| 4,921,479 A | 5/1990 | Grayzel |
| 5,071,430 A | 12/1991 | de Salis et al. |
| 5,104,025 A | 4/1992 | Main et al. |
| 5,139,513 A | 8/1992 | Segato |
| 5,158,567 A | 10/1992 | Green |
| 5,197,648 A | 3/1993 | Gingold |
| 5,205,459 A | 4/1993 | Brinkerhoff et al. |
| 5,222,963 A | 6/1993 | Brinkerhoff et al. |
| 5,222,975 A | 6/1993 | Crainich |

(Continued)

FOREIGN PATENT DOCUMENTS

| | | |
|---|---|---|
| CA | 2458946 A1 | 3/2003 |
| CA | 2512960 A1 | 1/2006 |

(Continued)

OTHER PUBLICATIONS

Disclosed Anonymously, "Motor-Driven Surgical Stapler Improvements," Research Disclosure Database No. 526041, Published: Feb. 2008.

(Continued)

*Primary Examiner* — Thanh Truong
*Assistant Examiner* — Nathaniel Chukwurah

(57) ABSTRACT

A surgical instrument that includes an elongated shaft that defines defining a central axis. The elongated shaft may have a distal end portion that is configured to operably support a circular staple cartridge therein. A tissue acquisition shaft may be axially movable within the elongated shaft such that a distal end portion of the tissue acquisition shaft may be distally advanced beyond the distal end portion of the elongated shaft. At least one tissue acquisition member may be pivotally attached to the distal end portion of the tissue acquisition shaft such that at least one tissue acquisition member is selectively pivotable about a corresponding acquisition axis that is substantially parallel to the central axis from a retracted position to deployed positions upon application of a deployment motion thereto. Various embodiments include an annular cutting member that is supported by the distal end of the elongated shaft for selective axial travel relative thereto.

16 Claims, 61 Drawing Sheets

(56) References Cited

U.S. PATENT DOCUMENTS

| | | |
|---|---|---|
| 5,234,447 A | 8/1993 | Kaster et al. |
| 5,236,440 A | 8/1993 | Hlavacek |
| 5,239,981 A | 8/1993 | Anapliotis |
| 5,258,009 A | 11/1993 | Conners |
| 5,282,829 A | 2/1994 | Hermes |
| 5,285,945 A | 2/1994 | Brinkerhoff et al. |
| 5,304,204 A | 4/1994 | Bregen |
| 5,309,927 A | 5/1994 | Welch |
| 5,336,232 A | 8/1994 | Green et al. |
| 5,342,395 A | 8/1994 | Jarrett et al. |
| 5,342,396 A | 8/1994 | Cook |
| 5,344,059 A | 9/1994 | Green et al. |
| 5,350,400 A | 9/1994 | Esposito et al. |
| 5,366,479 A | 11/1994 | McGarry et al. |
| 5,411,508 A | 5/1995 | Bessler et al. |
| 5,425,745 A | 6/1995 | Green et al. |
| 5,445,644 A | 8/1995 | Pietrafitta et al. |
| 5,478,354 A | 12/1995 | Tovey et al. |
| 5,483,952 A | 1/1996 | Aranyi |
| 5,484,095 A | 1/1996 | Green et al. |
| 5,487,500 A | 1/1996 | Knodel et al. |
| 5,489,256 A | 2/1996 | Adair |
| 5,503,635 A | 4/1996 | Sauer et al. |
| 5,507,426 A | 4/1996 | Young et al. |
| 5,554,169 A | 9/1996 | Green et al. |
| 5,569,161 A | 10/1996 | Ebling et al. |
| 5,575,803 A | 11/1996 | Cooper et al. |
| 5,609,285 A | 3/1997 | Grant et al. |
| 5,620,452 A | 4/1997 | Yoon |
| 5,630,782 A | 5/1997 | Adair |
| 5,632,433 A | 5/1997 | Grant et al. |
| 5,639,008 A * | 6/1997 | Gallagher et al. ......... 227/175.1 |
| 5,653,677 A | 8/1997 | Okada et al. |
| 5,653,721 A | 8/1997 | Knodel et al. |
| 5,658,238 A | 8/1997 | Suzuki et al. |
| 5,667,517 A | 9/1997 | Hooven |
| 5,667,527 A | 9/1997 | Cook |
| 5,669,918 A * | 9/1997 | Balazs et al. .................. 606/139 |
| 5,685,474 A | 11/1997 | Seeber |
| 5,695,504 A | 12/1997 | Gifford, III et al. |
| 5,697,943 A | 12/1997 | Sauer et al. |
| 5,702,409 A | 12/1997 | Rayburn et al. |
| 5,713,505 A | 2/1998 | Huitema |
| 5,718,360 A | 2/1998 | Green et al. |
| 5,725,554 A | 3/1998 | Simon et al. |
| 5,730,758 A | 3/1998 | Allgeyer |
| 5,749,889 A | 5/1998 | Bacich et al. |
| 5,752,644 A | 5/1998 | Bolanos et al. |
| 5,752,965 A | 5/1998 | Francis et al. |
| 5,758,814 A | 6/1998 | Gallagher et al. |
| 5,766,188 A | 6/1998 | Igaki |
| 5,772,578 A | 6/1998 | Heimberger et al. |
| 5,782,749 A | 7/1998 | Riza |
| 5,799,857 A | 9/1998 | Robertson et al. |
| 5,810,855 A | 9/1998 | Rayburn et al. |
| 5,814,057 A | 9/1998 | Oi et al. |
| 5,911,353 A | 6/1999 | Bolanos et al. |
| 5,915,616 A | 6/1999 | Viola et al. |
| 5,964,774 A | 10/1999 | McKean et al. |
| 5,971,916 A | 10/1999 | Koren |
| 6,024,748 A | 2/2000 | Manzo et al. |
| 6,050,990 A | 4/2000 | Tankovich et al. |
| 6,053,390 A * | 4/2000 | Green et al. ................ 227/179.1 |
| 6,063,097 A | 5/2000 | Oi et al. |
| 6,071,233 A | 6/2000 | Ishikawa et al. |
| 6,083,234 A | 7/2000 | Nicholas et al. |
| 6,083,242 A | 7/2000 | Cook |
| 6,099,551 A | 8/2000 | Gabbay |
| 6,102,271 A | 8/2000 | Longo et al. |
| 6,117,148 A | 9/2000 | Ravo et al. |
| 6,120,433 A | 9/2000 | Mizuno et al. |
| 6,126,058 A | 10/2000 | Adams et al. |
| 6,132,368 A | 10/2000 | Cooper |
| 6,159,146 A | 12/2000 | El Gazayerli |
| 6,171,330 B1 | 1/2001 | Benchetrit |
| 6,179,776 B1 | 1/2001 | Adams et al. |
| 6,193,129 B1 | 2/2001 | Bittner et al. |
| 6,258,107 B1 | 7/2001 | Balázs et al. |
| 6,264,086 B1 | 7/2001 | McGuckin, Jr. |
| 6,264,087 B1 | 7/2001 | Whitman |
| 6,315,184 B1 | 11/2001 | Whitman |
| 6,325,810 B1 | 12/2001 | Hamilton et al. |
| 6,352,503 B1 | 3/2002 | Matsui et al. |
| 6,387,113 B1 | 5/2002 | Hawkins et al. |
| 6,391,038 B2 | 5/2002 | Vargas et al. |
| 6,398,797 B2 | 6/2002 | Bombard et al. |
| RE37,814 E | 8/2002 | Allgeyer |
| 6,440,146 B2 | 8/2002 | Nicholas et al. |
| 6,443,973 B1 | 9/2002 | Whitman |
| 6,488,197 B1 | 12/2002 | Whitman |
| 6,491,201 B1 | 12/2002 | Whitman |
| 6,503,257 B2 | 1/2003 | Grant et al. |
| 6,503,259 B2 | 1/2003 | Huxel et al. |
| 6,505,768 B2 | 1/2003 | Whitman |
| 6,517,565 B1 | 2/2003 | Whitman et al. |
| 6,517,566 B1 | 2/2003 | Hovland et al. |
| 6,551,333 B2 | 4/2003 | Kuhns et al. |
| 6,569,085 B2 | 5/2003 | Kortenbach et al. |
| 6,589,164 B1 | 7/2003 | Flaherty |
| 6,592,597 B2 | 7/2003 | Grant et al. |
| 6,601,749 B2 | 8/2003 | Sullivan et al. |
| 6,616,686 B2 | 9/2003 | Coleman et al. |
| 6,629,630 B2 | 10/2003 | Adams |
| 6,629,988 B2 | 10/2003 | Weadock |
| 6,638,285 B2 | 10/2003 | Gabbay |
| 6,648,816 B2 | 11/2003 | Irion et al. |
| 6,648,901 B2 | 11/2003 | Fleischman et al. |
| 6,656,193 B2 | 12/2003 | Grant et al. |
| 6,681,979 B2 | 1/2004 | Whitman |
| 6,692,507 B2 | 2/2004 | Pugsley et al. |
| 6,695,199 B2 | 2/2004 | Whitman |
| 6,698,643 B2 | 3/2004 | Whitman |
| 6,716,233 B1 | 4/2004 | Whitman |
| 6,726,697 B2 | 4/2004 | Nicholas et al. |
| 6,740,030 B2 | 5/2004 | Martone et al. |
| 6,749,560 B1 | 6/2004 | Konstorum et al. |
| 6,761,685 B2 | 7/2004 | Adams et al. |
| 6,780,151 B2 | 8/2004 | Grabover et al. |
| 6,786,864 B2 | 9/2004 | Matsuura et al. |
| 6,790,173 B2 | 9/2004 | Saadat et al. |
| 6,805,273 B2 | 10/2004 | Bilotti et al. |
| 6,817,974 B2 | 11/2004 | Cooper et al. |
| 6,821,284 B2 | 11/2004 | Sturtz et al. |
| 6,837,846 B2 | 1/2005 | Jaffe et al. |
| RE38,708 E | 3/2005 | Bolanos et al. |
| 6,872,214 B2 | 3/2005 | Sonnenschein et al. |
| 6,878,106 B1 | 4/2005 | Herrmann |
| 6,913,608 B2 | 7/2005 | Liddicoat et al. |
| 6,939,358 B2 | 9/2005 | Palacios et al. |
| 6,960,163 B2 | 11/2005 | Ewers et al. |
| 6,960,220 B2 | 11/2005 | Marino et al. |
| 6,978,922 B2 | 12/2005 | Bilotti et al. |
| 6,981,978 B2 | 1/2006 | Gannoe |
| 6,984,203 B2 | 1/2006 | Tartaglia et al. |
| 7,029,435 B2 | 4/2006 | Nakao |
| 7,056,284 B2 | 6/2006 | Martone et al. |
| 7,056,330 B2 | 6/2006 | Gayton |
| 7,063,712 B2 | 6/2006 | Vargas et al. |
| 7,066,944 B2 | 6/2006 | Laufer et al. |
| 7,070,559 B2 | 7/2006 | Adams et al. |
| 7,077,856 B2 | 7/2006 | Whitman |
| 7,083,571 B2 | 8/2006 | Wang et al. |
| 7,090,637 B2 | 8/2006 | Danitz et al. |
| 7,091,412 B2 | 8/2006 | Wang et al. |
| 7,094,202 B2 | 8/2006 | Nobis et al. |
| 7,094,247 B2 | 8/2006 | Monassevitch et al. |
| 7,108,701 B2 | 9/2006 | Evens et al. |
| 7,108,709 B2 | 9/2006 | Cummins |
| 7,114,642 B2 | 10/2006 | Whitman |
| 7,118,528 B1 | 10/2006 | Piskun |
| 7,128,254 B2 | 10/2006 | Shelton, IV et al. |
| 7,128,748 B2 | 10/2006 | Mooradian et al. |
| 7,147,139 B2 | 12/2006 | Schwemberger et al. |
| 7,156,863 B2 | 1/2007 | Sonnenschein et al. |

(56) References Cited

U.S. PATENT DOCUMENTS

| | | |
|---|---|---|
| 7,159,750 B2 | 1/2007 | Racenet et al. |
| 7,179,223 B2 | 2/2007 | Motoki et al. |
| 7,179,267 B2 | 2/2007 | Nolan et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et |
| 7,213,736 B2 | 5/2007 | Wales et al. |
| 7,220,272 B2 | 5/2007 | Weadock |
| 7,234,624 B2 | 6/2007 | Gresham et al. |
| 7,238,195 B2 | 7/2007 | Viola |
| 7,267,679 B2 | 9/2007 | McGuckin, Jr. et al. |
| 7,278,563 B1 | 10/2007 | Green |
| 7,303,108 B2 | 12/2007 | Shelton, IV |
| 7,328,828 B2 | 2/2008 | Ortiz et al. |
| 7,354,447 B2 | 4/2008 | Shelton, IV et al. |
| 7,377,928 B2 | 5/2008 | Zubik et al. |
| 7,407,078 B2 | 8/2008 | Shelton, IV et al. |
| 7,416,101 B2 | 8/2008 | Shelton, IV et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,491,232 B2 | 2/2009 | Bolduc et al. |
| 7,494,039 B2 | 2/2009 | Racenet et al. |
| 7,500,979 B2 | 3/2009 | Hueil et al. |
| 7,506,791 B2 | 3/2009 | Omaits et al. |
| 7,510,107 B2 | 3/2009 | Timm et al. |
| 7,546,940 B2 | 6/2009 | Milliman et al. |
| 7,547,312 B2 | 6/2009 | Bauman et al. |
| 7,549,564 B2 | 6/2009 | Boudreaux |
| 7,566,300 B2 | 7/2009 | Devierre et al. |
| 7,568,603 B2 | 8/2009 | Shelton, IV et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,615,003 B2 | 11/2009 | Stefanchik et al. |
| 7,644,848 B2 | 1/2010 | Swayze et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,682,307 B2 | 3/2010 | Danitz et al. |
| 7,721,931 B2 | 5/2010 | Shelton, IV et al. |
| 7,721,934 B2 | 5/2010 | Shelton, IV et al. |
| 7,721,936 B2 | 5/2010 | Shelton, IV et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,770,775 B2 | 8/2010 | Shelton, IV et al. |
| 7,776,060 B2 | 8/2010 | Mooradian et al. |
| 7,780,685 B2 | 8/2010 | Hunt et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,692 B2 | 10/2010 | Hall et al. |
| 7,810,693 B2 | 10/2010 | Broehl et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,612 B2 | 11/2010 | Baxter, III et al. |
| 7,837,080 B2 | 11/2010 | Schwemberger |
| 7,845,537 B2 | 12/2010 | Shelton, IV et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,887,530 B2 | 2/2011 | Zemlok et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,913,891 B2 | 3/2011 | Doll et al. |
| 7,914,543 B2 | 3/2011 | Roth et al. |
| 7,918,377 B2 | 4/2011 | Measamer et al. |
| 7,922,061 B2 | 4/2011 | Shelton, IV et al. |
| 7,934,630 B2 | 5/2011 | Shelton, IV et al. |
| 7,938,307 B2 | 5/2011 | Bettuchi |
| 7,942,890 B2 | 5/2011 | D'Agostino et al. |
| 7,981,132 B2 | 7/2011 | Dubrul et al. |
| 8,002,795 B2 | 8/2011 | Beetel |
| 8,034,077 B2 | 10/2011 | Smith et al. |
| 8,038,046 B2 | 10/2011 | Smith et al. |
| D650,074 S | 12/2011 | Hunt et al. |
| 8,097,017 B2 | 1/2012 | Viola |
| 8,113,410 B2 | 2/2012 | Hall et al. |
| 8,123,103 B2 | 2/2012 | Milliman |
| 8,211,125 B2 | 7/2012 | Spivey |
| 2003/0195387 A1 | 10/2003 | Kortenbach et al. |
| 2003/0220660 A1 | 11/2003 | Kortenbach et al. |
| 2004/0006372 A1 | 1/2004 | Racenet et al. |
| 2004/0068161 A1 | 4/2004 | Couvillon, Jr. |
| 2004/0094597 A1 | 5/2004 | Whitman et al. |
| 2004/0097987 A1 | 5/2004 | Pugsley et al. |
| 2004/0167572 A1 | 8/2004 | Roth et al. |
| 2004/0222268 A1 | 11/2004 | Bilotti et al. |
| 2004/0254608 A1 | 12/2004 | Huitema et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0085693 A1 | 4/2005 | Belson et al. |
| 2005/0119525 A1 | 6/2005 | Takemoto |
| 2005/0124855 A1 | 6/2005 | Jaffe et al. |
| 2005/0137454 A1 | 6/2005 | Saadat et al. |
| 2005/0137455 A1 | 6/2005 | Ewers et al. |
| 2005/0145675 A1* | 7/2005 | Hartwick et al. .......... 227/180.1 |
| 2005/0154258 A1 | 7/2005 | Tartaglia et al. |
| 2005/0177181 A1 | 8/2005 | Kagan et al. |
| 2005/0182298 A1 | 8/2005 | Ikeda et al. |
| 2005/0187576 A1 | 8/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2006/0011699 A1 | 1/2006 | Olson et al. |
| 2006/0015009 A1 | 1/2006 | Jaffe et al. |
| 2006/0020213 A1* | 1/2006 | Whitman et al. ............ 600/478 |
| 2006/0047307 A1 | 3/2006 | Ortiz et al. |
| 2006/0052825 A1 | 3/2006 | Ransick et al. |
| 2006/0079735 A1 | 4/2006 | Martone et al. |
| 2006/0085033 A1 | 4/2006 | Criscuolo et al. |
| 2006/0108393 A1 | 5/2006 | Heinrich et al. |
| 2006/0161185 A1 | 7/2006 | Saadat et al. |
| 2006/0173470 A1 | 8/2006 | Oray et al. |
| 2006/0235469 A1 | 10/2006 | Viola |

(56) References Cited

U.S. PATENT DOCUMENTS

| | | |
|---|---|---|
| 2006/0241692 A1 | 10/2006 | McGuckin et al. |
| 2006/0258904 A1 | 11/2006 | Stefanchik et al. |
| 2006/0258910 A1 | 11/2006 | Stefanchik et al. |
| 2006/0289602 A1 | 12/2006 | Wales et al. |
| 2007/0034668 A1 | 2/2007 | Holsten et al. |
| 2007/0073341 A1 | 3/2007 | Smith et al. |
| 2007/0102472 A1 | 5/2007 | Shelton, IV |
| 2007/0106317 A1 | 5/2007 | Shelton, IV et al. |
| 2007/0135803 A1 | 6/2007 | Belson |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194081 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0225562 A1 | 9/2007 | Spivey et al. |
| 2007/0295780 A1 | 12/2007 | Shelton et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082114 A1 | 4/2008 | McKenna et al. |
| 2008/0082115 A1 | 4/2008 | Morgan et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0140115 A1 | 6/2008 | Stopek |
| 2008/0167522 A1 | 7/2008 | Giordano et al. |
| 2008/0167671 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172088 A1 | 7/2008 | Smith et al. |
| 2008/0185419 A1 | 8/2008 | Smith et al. |
| 2008/0228029 A1 | 9/2008 | Mikkaichi et al. |
| 2008/0237296 A1 | 10/2008 | Boudreaux et al. |
| 2008/0255413 A1 | 10/2008 | Zemlok et al. |
| 2008/0296346 A1 | 12/2008 | Shelton, IV et al. |
| 2008/0300580 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0314957 A1 | 12/2008 | Boudreaux |
| 2009/0001121 A1 | 1/2009 | Hess et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012556 A1 | 1/2009 | Boudreaux et al. |
| 2009/0076534 A1 | 3/2009 | Shelton, IV et al. |
| 2009/0078736 A1 | 3/2009 | Van Lue |
| 2009/0149871 A9 | 6/2009 | Kagan et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206138 A1 | 8/2009 | Smith et al. |
| 2009/0206139 A1 | 8/2009 | Hall et al. |
| 2009/0206140 A1 | 8/2009 | Scheib et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0209946 A1 | 8/2009 | Swayze et al. |
| 2009/0242610 A1 | 10/2009 | Shelton, IV et al. |
| 2009/0255978 A1 | 10/2009 | Viola et al. |
| 2010/0012704 A1 | 1/2010 | Tarinelli Racenet et al. |
| 2010/0032470 A1 | 2/2010 | Hess et al. |
| 2010/0065605 A1 | 3/2010 | Shelton, IV et al. |
| 2010/0069942 A1 | 3/2010 | Shelton, IV |
| 2010/0072252 A1 | 3/2010 | Baxter, III et al. |
| 2010/0076474 A1 | 3/2010 | Yates et al. |
| 2010/0076475 A1 | 3/2010 | Yates et al. |
| 2010/0089970 A1 | 4/2010 | Smith et al. |
| 2010/0089974 A1 | 4/2010 | Shelton, IV |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0145146 A1 | 6/2010 | Melder |
| 2010/0163598 A1 | 7/2010 | Belzer |
| 2010/0179382 A1 | 7/2010 | Shelton, IV et al. |
| 2010/0181364 A1 | 7/2010 | Shelton, IV et al. |
| 2010/0193566 A1 | 8/2010 | Schieb et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0237132 A1 | 9/2010 | Measamer et al. |
| 2010/0243709 A1 | 9/2010 | Hess et al. |
| 2010/0264193 A1 | 10/2010 | Huang et al. |
| 2010/0264194 A1 | 10/2010 | Huang et al. |
| 2010/0268030 A1 | 10/2010 | Viola et al. |
| 2010/0276471 A1 | 11/2010 | Whitman |
| 2010/0294829 A1 | 11/2010 | Giordano et al. |
| 2010/0301095 A1 | 12/2010 | Shelton, IV et al. |
| 2010/0301096 A1 | 12/2010 | Moore et al. |
| 2010/0305552 A1 | 12/2010 | Shelton, IV et al. |
| 2010/0308100 A1 | 12/2010 | Boudreaux |
| 2010/0312261 A1 | 12/2010 | Suzuki et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0042441 A1 | 2/2011 | Shelton, IV et al. |
| 2011/0060363 A1 | 3/2011 | Hess et al. |
| 2011/0062212 A1 | 3/2011 | Shelton, IV et al. |
| 2011/0068145 A1 | 3/2011 | Bedi et al. |
| 2011/0068148 A1 | 3/2011 | Hall et al. |
| 2011/0084113 A1 | 4/2011 | Bedi et al. |
| 2011/0084115 A1 | 4/2011 | Bedi et al. |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0118761 A1 | 5/2011 | Baxter, III et al. |
| 2011/0121051 A1 | 5/2011 | Shelton, IV et al. |
| 2011/0121052 A1 | 5/2011 | Shelton, IV et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139852 A1 | 6/2011 | Zingman |
| 2011/0144430 A1 | 6/2011 | Spivey et al. |

(56) References Cited

U.S. PATENT DOCUMENTS

| | | |
|---|---|---|
| 2011/0147433 A1 | 6/2011 | Shelton, IV et al. |
| 2011/0147434 A1 | 6/2011 | Hueil et al. |
| 2011/0155780 A1 | 6/2011 | Boudreaux |
| 2011/0155781 A1 | 6/2011 | Swensgard et al. |
| 2011/0155785 A1 | 6/2011 | Laurent et al. |
| 2011/0155787 A1 | 6/2011 | Baxter, III et al. |
| 2011/0163147 A1 | 7/2011 | Laurent et al. |
| 2011/0174860 A1 | 7/2011 | Shelton, IV et al. |
| 2011/0174863 A1 | 7/2011 | Shelton, IV et al. |
| 2011/0192882 A1 | 8/2011 | Hess et al. |
| 2011/0226837 A1 | 9/2011 | Baxter, III et al. |
| 2011/0233258 A1 | 9/2011 | Boudreaux |
| 2011/0253766 A1 | 10/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0290857 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0024934 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0061448 A1 | 3/2012 | Zingman |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0138660 A1 | 6/2012 | Shelton, IV |
| 2012/0160721 A1 | 6/2012 | Shelton, IV et al. |
| 2012/0175399 A1 | 7/2012 | Shelton et al. |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |

FOREIGN PATENT DOCUMENTS

| | | |
|---|---|---|
| CA | 2514274 A1 | 1/2006 |
| CN | 1868411 A | 11/2006 |
| CN | 1915180 A | 2/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |
| EP | 0387980 B1 | 10/1985 |
| EP | 0033548 B1 | 5/1986 |
| EP | 0276104 A2 | 7/1988 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |

(56) References Cited

FOREIGN PATENT DOCUMENTS

| | | | |
|---|---|---|---|
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 81 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 81 | 12/2006 |
| EP | 1285633 B1 | 12/2006 |
| EP | 1728473 A1 | 12/2006 |
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1785097 A2 | 5/2007 |
| EP | 1790293 A2 | 5/2007 |
| EP | 1800610 A1 | 6/2007 |
| EP | 1300117 B1 | 8/2007 |
| EP | 1813199 A1 | 8/2007 |
| EP | 1813201 A1 | 8/2007 |
| EP | 1813203 A2 | 8/2007 |

(56) References Cited

FOREIGN PATENT DOCUMENTS

| | | |
|---|---|---|
| EP | 1813207 A1 | 8/2007 |
| EP | 1813209 A1 | 8/2007 |
| EP | 1487359 B1 | 10/2007 |
| EP | 1599146 B1 | 10/2007 |
| EP | 1839596 A1 | 10/2007 |
| EP | 1402821 B1 | 12/2007 |
| EP | 1872727 A1 | 1/2008 |
| EP | 1897502 A1 | 3/2008 |
| EP | 1330201 B1 | 6/2008 |
| EP | 1702568 B1 | 7/2008 |
| EP | 1943957 A2 | 7/2008 |
| EP | 1943976 A2 | 7/2008 |
| EP | 1593337 B1 | 8/2008 |
| EP | 1970014 A1 | 9/2008 |
| EP | 1980213 A2 | 10/2008 |
| EP | 1759645 B1 | 11/2008 |
| EP | 1990014 A2 | 11/2008 |
| EP | 1693008 B1 | 12/2008 |
| EP | 1759640 B1 | 12/2008 |
| EP | 2000102 A2 | 12/2008 |
| EP | 1736104 B1 | 3/2009 |
| EP | 1749486 B1 | 3/2009 |
| EP | 2039316 A2 | 3/2009 |
| EP | 1721576 B1 | 4/2009 |
| EP | 1733686 B1 | 4/2009 |
| EP | 2044890 A1 | 4/2009 |
| EP | 1550413 B1 | 6/2009 |
| EP | 1745748 B1 | 8/2009 |
| EP | 2090256 A2 | 8/2009 |
| EP | 1813208 B1 | 11/2009 |
| EP | 1607050 B1 | 12/2009 |
| EP | 1566150 B1 | 4/2010 |
| EP | 1813206 B1 | 4/2010 |
| EP | 1769754 B1 | 6/2010 |
| EP | 1535565 B1 | 10/2010 |
| EP | 1702570 B1 | 10/2010 |
| EP | 1785098 B1 | 10/2010 |
| EP | 2030578 B1 | 11/2010 |
| EP | 1627605 B1 | 12/2010 |
| EP | 1813205 B1 | 6/2011 |
| EP | 1785102 B1 | 1/2012 |
| FR | 999646 A | 2/1952 |
| FR | 1112936 A | 3/1956 |
| FR | 2765794 A | 1/1999 |
| GB | 939929 A | 10/1963 |
| GB | 1210522 A | 10/1970 |
| GB | 1217159 A | 12/1970 |
| GB | 1339394 A | 12/1973 |
| GB | 2109241 A | 6/1983 |
| GB | 2272159 A | 5/1994 |
| GB | 2284242 A | 5/1995 |
| GB | 2336214 A | 10/1999 |
| GB | 2425903 A | 11/2006 |
| JP | S 58500053 A | 1/1983 |
| JP | 61-98249 A | 5/1986 |
| JP | 63-203149 | 8/1988 |
| JP | 3-12126 A | 1/1991 |
| JP | 5-212039 A | 8/1993 |
| JP | 6007357 A | 1/1994 |
| JP | 7051273 A | 2/1995 |
| JP | 8033641 A | 2/1996 |
| JP | 8229050 A | 9/1996 |
| JP | 2000033071 A | 2/2000 |
| JP | 2000171730 A | 6/2000 |
| JP | 2000287987 A | 10/2000 |
| JP | 2000325303 A | 11/2000 |
| JP | 2001-514541 A | 9/2001 |
| JP | 2001286477 A | 10/2001 |
| JP | 2002143078 A | 5/2002 |
| JP | 2002369820 A | 12/2002 |
| JP | 2004-344663 | 12/2004 |
| JP | 2005-028149 A | 2/2005 |
| JP | 2005505322 T | 2/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005152416 A | 6/2005 |
| JP | 2005-523105 A | 8/2005 |
| JP | 2005524474 A | 8/2005 |
| JP | 2006-281405 A | 10/2006 |
| RU | 2008830 C1 | 3/1994 |
| RU | 2187249 C2 | 8/2002 |
| RU | 2225170 C2 | 3/2004 |
| SU | 189517 A | 1/1967 |
| SU | 328636 A | 9/1972 |
| SU | 886900 A1 | 12/1981 |
| SU | 1009439 A | 4/1983 |
| SU | 1333319 A2 | 8/1987 |
| SU | 1377053 A1 | 2/1988 |
| SU | 1561964 A1 | 5/1990 |
| SU | 1722476 A1 | 3/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |

(56) References Cited

FOREIGN PATENT DOCUMENTS

| | | |
|---|---|---|
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A1 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039270 A1 | 4/2008 |
| WO | WO 2008/045383 A2 | 4/2008 |
| WO | WO 2008/089404 A2 | 7/2008 |

(56) References Cited

FOREIGN PATENT DOCUMENTS

| WO | WO 2008/109125 A1 | 9/2008 |
|---|---|---|
| WO | WO 2008/124748 A1 | 10/2008 |
| WO | WO 2010/063795 A1 | 6/2010 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

U.S. Appl. No. 12/846,952, filed Jul. 30, 2010.
U.S. Appl. No. 12/846,956, filed Jul. 30, 2010.
U.S. Appl. No. 12/846,968, filed Jul. 30, 2010.
U.S. Appl. No. 12/846,978, filed Jul. 30, 2010.

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

International Search Report for PCT/US2011/045530, dated Nov. 24, 2011 (4 pages).

\* cited by examiner

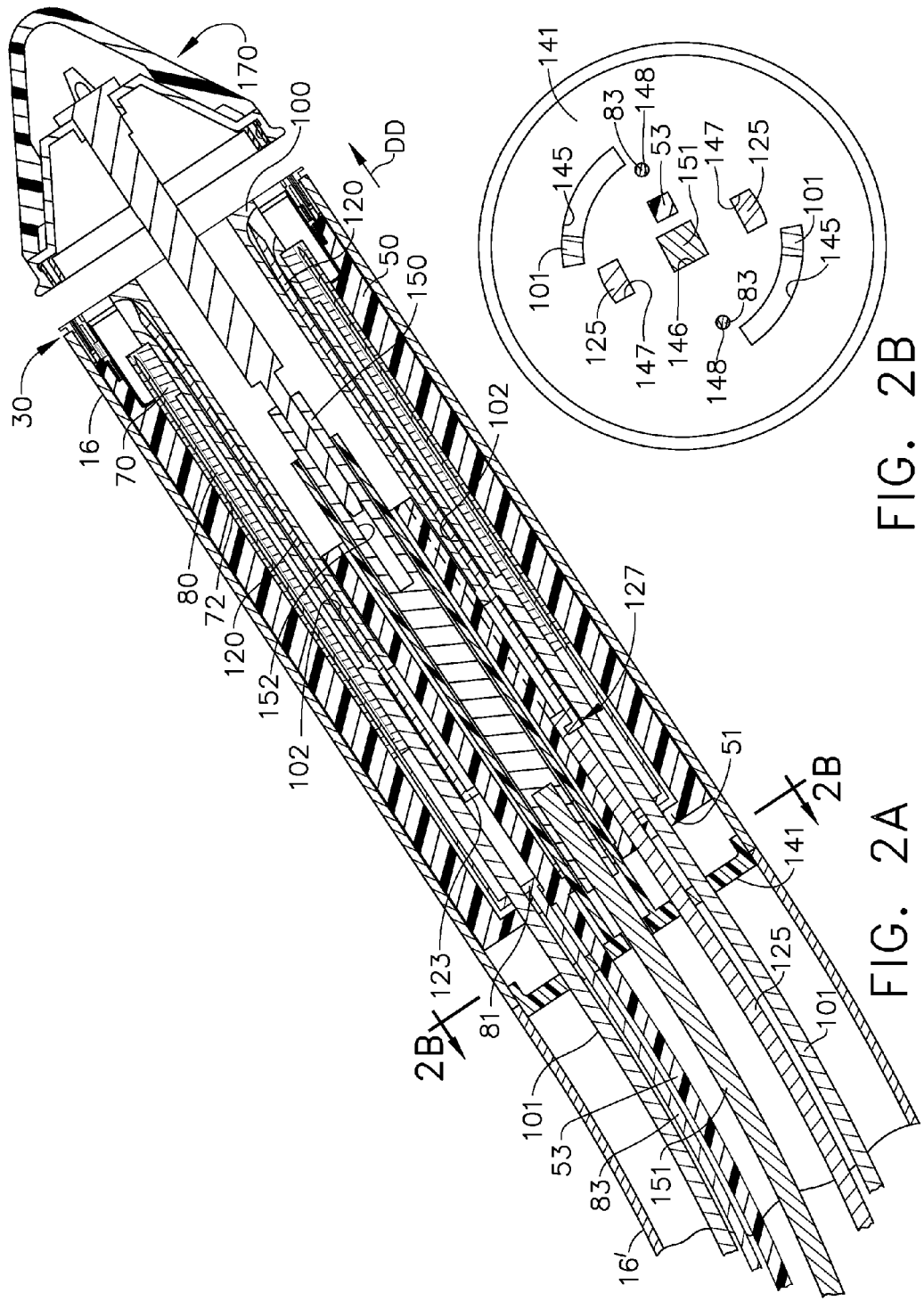

TISSUE ACQUISITION ARRANGEMENTS AND METHODS FOR SURGICAL STAPLING DEVICES

FIELD OF THE INVENTION

The present invention generally relates to surgical staplers, and more particularly, to devices and methods for holding and/or protecting tissue adjacent to the stapler head of a circular stapler.

BACKGROUND

In certain types of surgical procedures, the use of surgical staples has become the preferred method of joining tissue and, as such, specially configured surgical staplers have been developed for these applications. For example, intra-luminal or circular staplers have been developed for use in surgical procedures involving the lower colon wherein sections of the lower colon are joined together after a diseased portion has been excised. Circular staplers useful for performing such procedures are disclosed, for example, in U.S. Pat. Nos. 5,104,025; 5,205,459; 5,285,945; and 5,309,927 which are each herein incorporated by reference in their respective entireties.

In general, a conventional circular stapler typically consists of an elongated shaft that has a proximal actuating mechanism and a distal stapler head mounted to the elongated shaft. The distal stapler head commonly consists of a fixed stapling cartridge that contains a plurality of staples configured in a concentric circular array. A round cutting knife is concentrically mounted in the cartridge interior to the staples for axial travel therein. Extending axially from the center of the cartridge is a movable trocar shaft that is adapted to have a staple anvil removably coupled thereto. The anvil is configured to form the ends of the staples as they are driven into it. The distance between a distal face of the staple cartridge and the staple anvil is commonly controlled by an adjustment mechanism that is mounted to the proximal end of the stapler shaft for controlling the axial movement of the trocar. Tissue that is clamped between the staple cartridge and the staple anvil is simultaneously stapled and cut when the actuating mechanism is activated by the surgeon.

When performing a lower colon procedure using a circular stapler, a portion of the intestine may be laproscopically stapled using a conventional surgical stapler that is inserted through a trocar. The conventional surgical stapler serves to place multiple rows of staples on either side of the diseased portion of colon to be removed. The target or diseased section is simultaneously cut as the adjoining end of the colon is stapled. After removing the diseased portion, the surgeon typically inserts the anvil of the circular stapling instrument into the distal end of the lumen, distal of the staple line. This may be done by inserting the anvil head into an entry port cut into the distal lumen by the surgeon. The lower staple line is utilized to hold the tissue of the colon over the circular cartridge. This method seals both ends of the colon only to have the sealed portions cut through and removed. These intermediate step staple lines are only temporary and facilitate the next step in the procedure.

On occasion, the anvil can be placed transanally, by placing the anvil head on the distal end of the stapler and inserting the instrument through the rectum. Once the anvil has been installed in the distal portion of the intestine, the intestine is secured around the anvil shaft by what is known as a "purse string" suture. The proximal portion of intestine is similarly secured around the stapler head by a purse string suture.

Once the ends of the intestine have been secured around their respective components, the surgeon, through an appropriate trocar sleeve, may employ a grasping device to grasp the anvil shaft and attach it to the portion of the trocar protruding within the stapler head. The surgeon then closes the gap between the anvil and cartridge, thereby clamping the proximal and distal ends of the intestine in the gap. The surgeon next actuates the stapler causing several rows of staples to be driven through both ends of the intestine and formed, thereby joining the ends and forming a tubular pathway. Simultaneously, as the staples are driven and formed, the concentric annular knife blade is driven through the intestinal tissue ends, cutting the ends adjacent to the inner row of staples. The surgeon then withdraws the stapler from the intestine and the procedure is complete.

Such procedures and devices require the surgeon to install two purse string sutures which lengthens the time required to complete the surgical procedure. In addition, such procedures may at times cause tissue "bunching" during the tissue cutting/stapling process.

Various attempts have been made to retain colon and other tissues around the stapling device. For example, U.S. Pat. Nos. 5,309,927; 6,117,148; and 7,094,247 disclose various arrangements that, in general, employ fasteners, ligation members, rings, springs, etc. that are apart from the stapling device itself in an effort to retain the tissue in position. U.S. Pat. No. 5,669,918 discloses a mechanism that employs a grasper like arm to frictionally pin the tissue against the trocar shank. While such device is essentially self contained, the grasper arms may ultimately be unable to effectively retain the tissue in position in practice.

Thus, the need exists for devices and methods for reducing the time required to complete the surgical procedure as well as addressing other shortcomings and challenges associated with retaining tissue in position when employing circular stapler arrangements.

The foregoing discussion is intended only to illustrate some of the shortcomings present in the field of the invention at the time, and should not be taken as a disavowal of claim scope.

SUMMARY

In connection with a general aspect of various embodiments of the present invention, there is provided a surgical instrument that comprises an elongated shaft that defines a central axis and has a distal end portion that is configured to operably support a circular staple cartridge therein. A tissue acquisition shaft is rotatably supported within the elongated shaft and has a distal portion that protrudes distally beyond the distal end portion of the elongated shaft. At least one tissue acquisition member is pivotally attached to the distal end portion of the tissue acquisition shaft such that the at least one tissue acquisition member is selectively pivotable about a corresponding acquisition axis that is substantially parallel to the central axis from a retracted position to deployed positions upon application of a deployment motion thereto.

In connection with another general aspect of various embodiments of the invention, there is provided a surgical instrument that comprises an elongated shaft that defines a central axis and terminates in a stapler head. In various embodiments, the stapler head comprises a circular staple cartridge that has a fastener face. The stapler head also comprises an axially movable cutting member. The surgical instrument further comprises a firing member that is operably supported in the elongated shaft and oriented to apply a firing motion to the circular staple cartridge. An anvil shaft assembly is operably supported within the elongated shaft and is configured to receive actuation motions from the handle assembly to cause the anvil shaft assembly to move axially within the elongated shaft such that a distal connection portion thereof moves axially relative to the fastener face. An anvil is removably attachable to the distal connection portion of the anvil shaft assembly. A tissue acquisition shaft is rotatably supported within the elongated shaft. A plurality of tissue acquisition members is pivotally attached to a distal end portion of the tissue acquisition shaft. The plurality of tissue acquisition members is selectively pivotable between a retracted position to deployed positions upon application of a deployment motion thereto. The surgical instrument further comprises at least one tissue acquisition pin that corresponds to each one of the at least one tissue acquisition members. Each tissue acquisition pin radially protrudes outward from the distal end of the tissue acquisition shaft to impale tissue drawn in towards the tissue acquisition shaft by the tissue acquisition members when the tissue acquisition members are moved from the deployed to the retracted position.

In connection with yet another general aspect of various embodiments of the present invention, there is provided a surgical procedure for performing a circular anastomosis of a tubular organ. In various embodiments, the surgical procedure comprises inserting a stapler head of a surgical instrument into the tubular organ adjacent a targeted portion thereof. The stapler head operably supports a staple cartridge therein that has a fastener face. The procedure further includes acquiring a proximal portion of the tubular organ that is adjacent to the targeted portion with a plurality of tissue acquisition members of the surgical instrument. The procedure further comprises severing the proximal portion of the tubular organ from the targeted portion with the plurality of tissue acquisition members and retaining the proximal portion of the tubular organ adjacent to the fastener face of the staple cartridge. In various embodiments, the surgical procedure further involves severing the targeted portion of the tubular organ from a distal portion of the tubular organ and inserting an anvil into the distal portion of the tubular organ such that a connection portion of the anvil protrudes proximally out of an open end of the distal portion of the tubular organ. The procedure further comprises securing the distal portion of the tubular organ to the anvil and coupling the connection portion of the anvil to the surgical instrument. Thereafter, the procedure comprises drawing the anvil proximally toward the stapler head such that a proximal end of the distal portion of the tubular organ and the retained proximal portion of the tubular organ are adjacent to each other and captured between the anvil and the fastener face and thereafter stapling the proximal end of the distal portion and the retained proximal portion together to form a repaired tubular organ. The procedure further includes cutting through the proximal end of the distal portion and retained proximal portion adjacent to the staples.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 2A is a partial cross-sectional view of the distal end of the elongated shaft with an anvil coupled thereto;

FIG. 2B is a partial cross-sectional view of the distal end of the elongated shaft taken along line 2B-2B in FIG. 2A;

DETAILED DESCRIPTION

Figure 1:
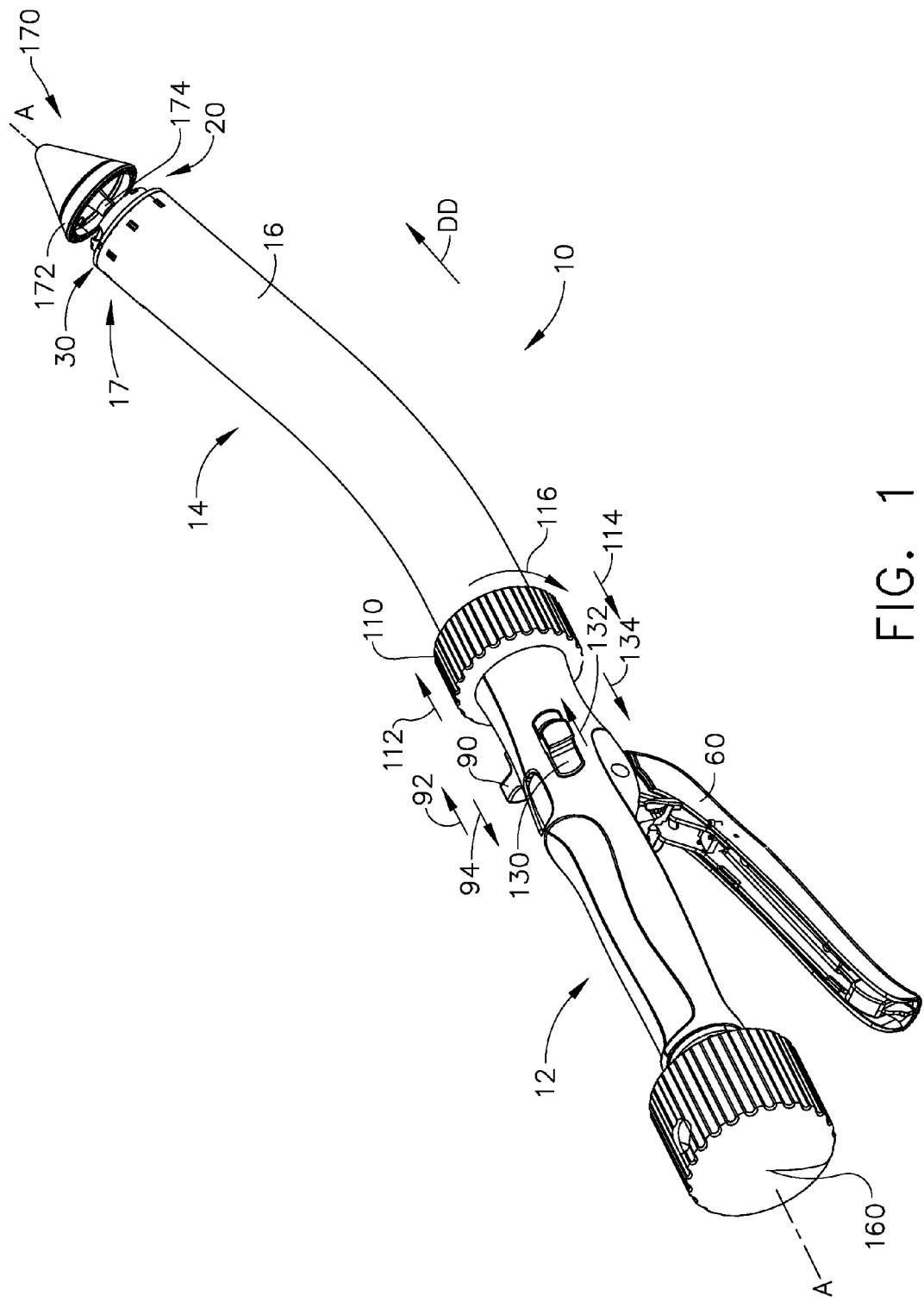
FIG. 1 is a perspective view of a surgical circular stapling instrument of various non-limiting embodiments of the present invention.

The Applicant of the present application also owns the U.S. Patent Applications identified below which were filed on even date herewith and which are each herein incorporated by reference in their respective entirety:

U.S. patent application Ser. No. 12/846,978, entitled "Surgical Circular Stapler With Tissue Retention Arrangements";

U.S. patent application Ser. No. 12/846,956, entitled "Transwall Visualization Arrangements and Methods For Surgical Circular Staplers";

U.S. patent application Ser. No. 12/846,968, entitled "Circular Stapling Instruments With Secondary Cutting Arrangements and Methods of Using Same"; and U.S. patent application Ser. No. 12/846,952, entitled "Apparatus and Methods For Protecting Adjacent Structures During the Insertion of a Surgical Instrument Into a Tubular Organ".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

FIG. 1 illustrates a circular stapler 10 according to various non-limiting embodiments of the invention. In various embodiments, the circular stapler 10 includes a handle assembly 12 that has an elongated shaft assembly 14 protruding therefrom that defines a central axis A-A. The elongate shaft assembly 14 includes a rigid outer sheath 16 that has a distal end portion 17 that forms a stapler head 20. In various non-limiting embodiments, the stapler head 20 is configured to operably support a circular staple cartridge 30 therein. Such circular staple cartridges 30 are known in the art and may generally support one, two, or more circumferentially spaced and staggered rows of staples 36 therein. See FIGS. 2 and 3. The embodiment depicted in FIG. 3, for example, has two rows 32, 34, of staples 36. A conventional annular knife 40 is coaxially and movably supported within the stapler head 20.

In certain implementations, the circular stapler 10 further includes a firing shaft assembly 50 that is supported within the outer sheath 16 for selective axial travel therein. See FIG. 2. A distal end portion 52 of the firing shaft assembly 50 has an outer staple driver portion 54 thereon for engagement with each of the staples 36 in the outer row 32 of staples 36 in the staple cartridge 30. In addition, the distal end portion 52 of the firing shaft assembly 50 has an inner staple driver portion 56 that is configured for engagement with each of the staples 36 in the inner row 34 of staples 36 within the staple cartridge 30. As can also be seen in FIG. 2, for example, the distal end portion 52 of the firing shaft assembly 50 further has a ledge 58 that is configured to engage the annular knife 40. Thus, as will be discussed in further detail below, axial advancement of the firing shaft assembly 50 in a distal direction "DD", will cause the staples 36 to be driven out of the staple cartridge 30 as well as the annular knife 40 to be advanced distally. As can be seen in FIG. 2A, the firing shaft assembly 50 has a base portion 51 that is coupled to a firing rod 53.

Figures 1A, 2C:
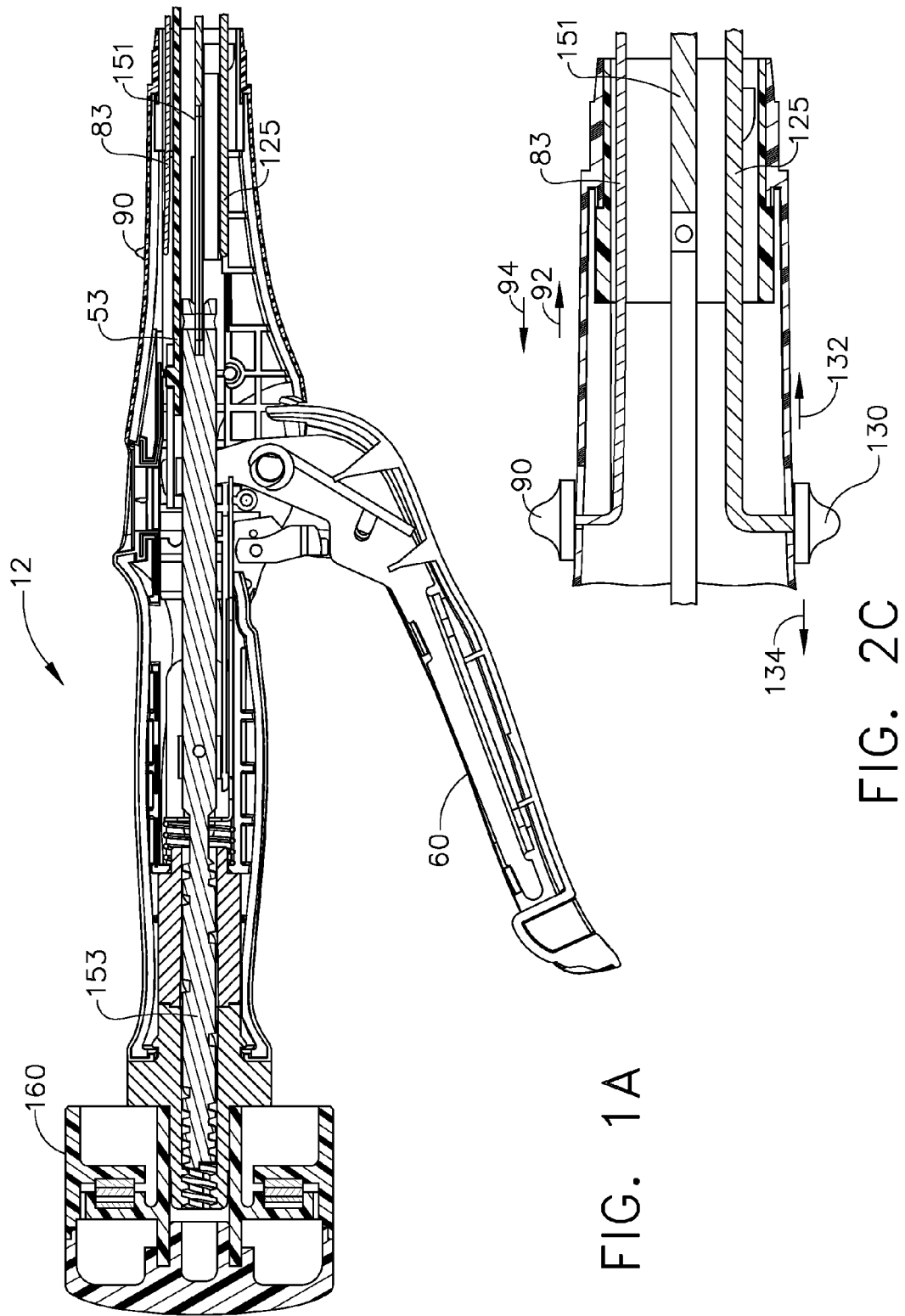
FIG. 1A is a cross-sectional view of the handle portion of various embodiments of the surgical stapling instrument of the present invention.
FIG. 2C is a cross-sectional view of a portion of the handle assembly of an embodiment of the present invention.

In various non-limiting embodiments, the firing rod 53 operably interfaces with a firing trigger 60 that is operably coupled to the handle assembly 12. See FIGS. 1 and 1A. As can be seen in FIGS. 1 and 1A, the firing trigger 60 is pivotally coupled to the handle assembly 12 such that when the firing trigger 60 is pivoted toward the handle assembly 12, the firing shaft assembly 50 is moved in the distal direction DD. Such firing trigger arrangements are known in the art and therefore will not be discussed in detail herein. For example, an exemplary firing trigger arrangement is disclosed in U.S. Patent Application Publication No. US 2008/0078806 A1, entitled "Surgical Stapling Instrument With Mechanical Indicator to Show Levels of Tissue Compression", the disclosure of which is herein incorporated by reference in its entirety.

Figure 2:
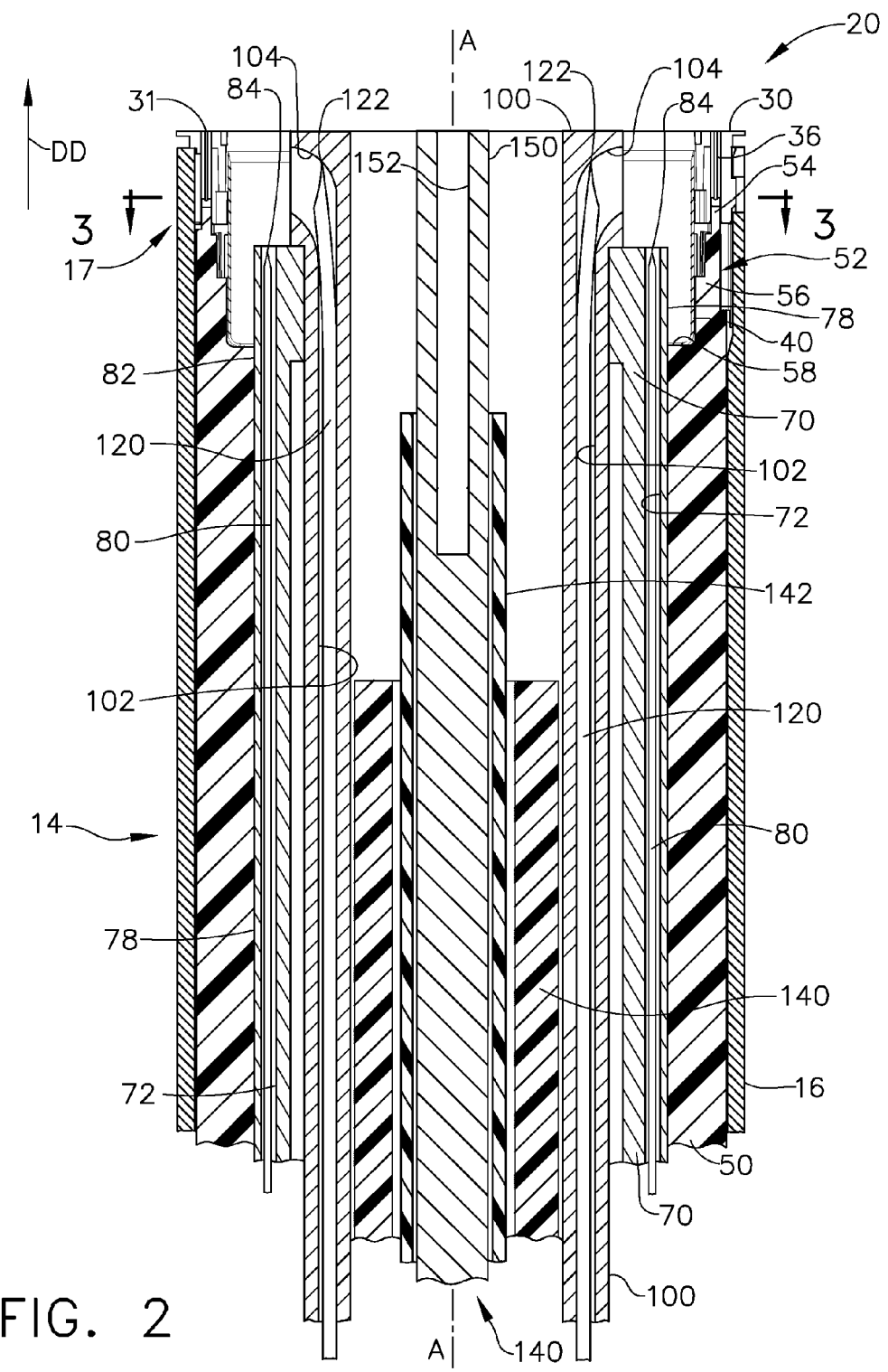
FIG. 2 is a cross-sectional view of a distal end portion of the elongated shaft of the circular stapling instrument of FIG. 1.
Figure 2D:
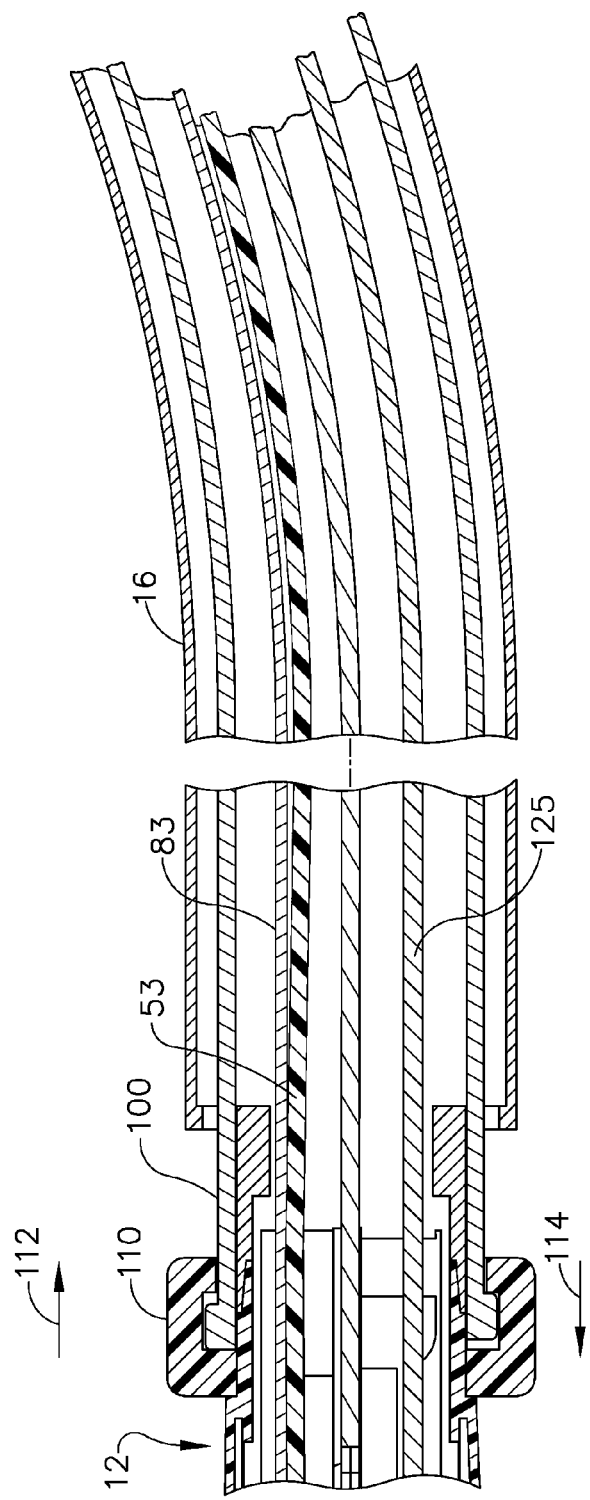
FIG. 2D is a cross-sectional view of another portion of the elongated shaft of various embodiments of the present invention.
Figure 3:
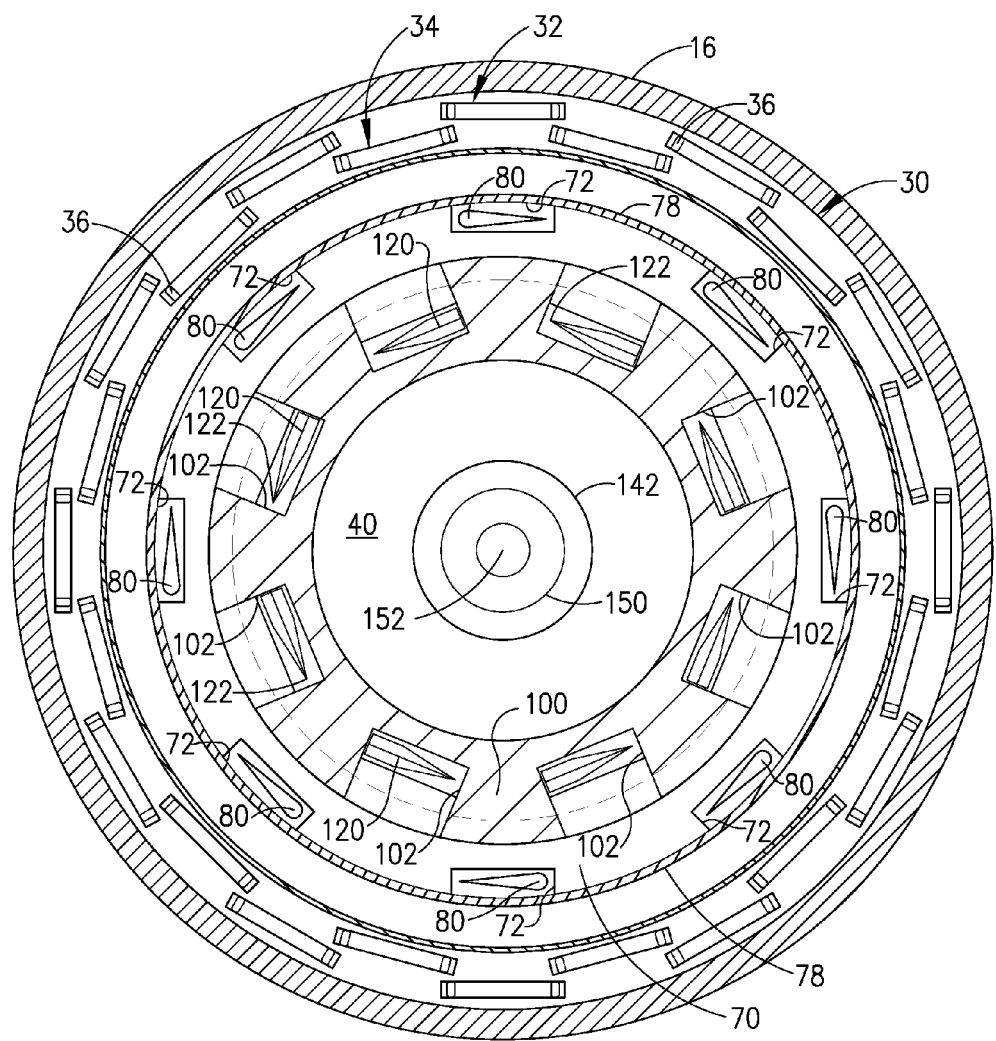
FIG. 3 is an end view of the elongated shaft of FIG. 2.

As shown in FIGS. 2 and 2A, various non-limiting embodiments include an acquisition housing 70 that is coaxially supported within the firing shaft assembly 50 and is axially movable relative thereto. The acquisition housing 70 has a plurality of acquisition lumens 72 therein that each movably support an acquisition or hook member 80. As can be seen in FIG. 3, for example, the plurality of three-sided acquisition lumens 72 may be equally spaced around the circumference of the acquisition housing 70. In the non-limiting embodiment depicted in FIG. 3, a total of eight (8) acquisition lumens 72 are equally spaced around the circumference of the acquisition housing 70.

Figure 4:
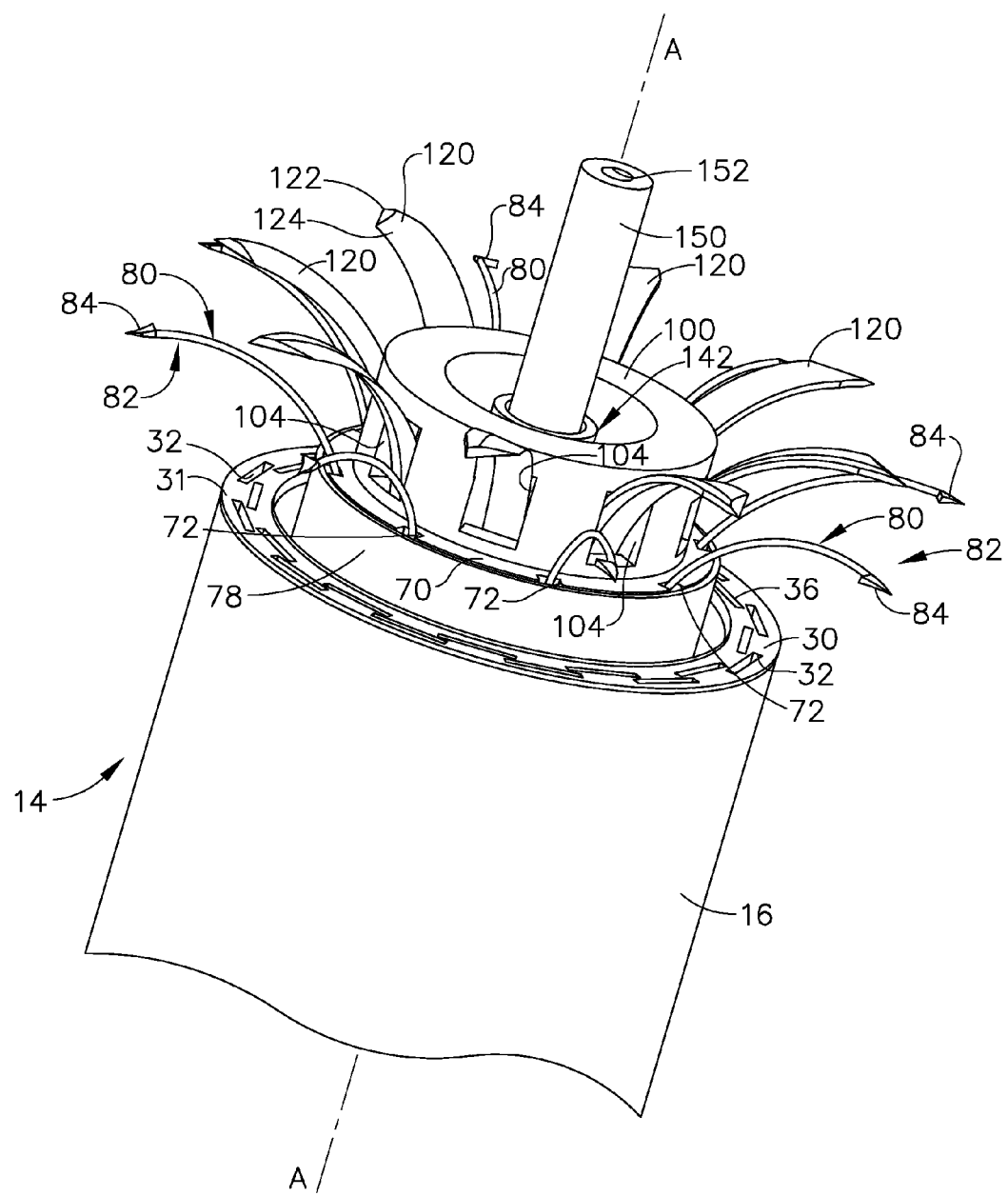
FIG. 4 is a partial perspective view of the distal end portion of the elongated shaft of FIGS. 2 and 3 with the tissue acquisition members and the knife members thereof in their radially deployed positions.

Each acquisition or hook member 80 may be fabricated from, for example, Nitinol, 300 or 400 series stainless steel (fully or three-fourths hardened) and have a distal end portion 82 that, when advanced out of its respective acquisition lumen 72, bends radially outward as shown in FIG. 4. As can also be seen in FIG. 4, each hook member 80 has a tissue barb 84 formed on the distal end portion 82 thereof. As can be seen in FIGS. 2 and 3, in various non-limiting embodiments, a sleeve 78 is employed to facilitate installation of the hook members 80 into their respective lumens 72.

As can be seen in FIG. 2A, each of the hook members 80 are coupled to or protrude from an acquisition ring 81 that has a pair of acquisition rods 83 attached thereto. The acquisition rods 83 are attached to a hook switch 90 that is operably supported on the handle assembly 12. See FIGS. 1 and 2C. As the surgeon moves the hook switch 90 in a distal direction (arrow 92 in FIGS. 1 and 2C), the acquisition housing 70 moves distally. Such movement of the acquisition housing 70 causes the distal end portion 84 of each hook member 80 to be advanced distally out of its respective acquisition lumen 72. As the distal end portion 84 of each hook member 80 is advanced out of the acquisition lumen 72, the natural bending action of the hook member 80 causes the end portion 84 to bend radially away from the central axis A-A as illustrated in FIG. 4. The surgeon may retract the acquisition housing 70 and the hook members 80 into their starting positions (FIG. 2), by moving the hook switch 90 in a proximal direction (arrow 94 in FIGS. 1 and 2C).

As can be further seen in FIGS. 2, 2A, 2D, 3 and 4, in various non-limiting embodiments, a cutter housing 100 is coaxially supported within the acquisition housing 70. The cutter housing 100 is supported for selective axial travel relative to the acquisition housing 70 and for selective axial travel along central axis A-A. In various embodiments, a pair of housing actuation rods 101 protrude from the cutter housing 100 to interface with a knife knob 110 that is movably supported on the handle assembly 12. See FIGS. 1 and 2D. In various non-limiting embodiments, the knife knob 110 is supported on the handle assembly 12 such that it can move axially (represented by arrows 112, 114 in FIGS. 1 and 2D) and also be rotated relative to the handle assembly 12 (represented by arrow 116 in FIG. 1). The housing actuator rods 101 are attached to the knife knob 110 such that movement of the knife knob 110 in an axial direction moves the cutter housing 100 axially within the acquisition housing 70 and rotation of the knife knob 110 also rotates the cutter housing 100 about the central axis A-A as will be discussed in further detail below.

In various non-limiting embodiments, the cutter housing 100 includes at least one, and preferably a plurality of, knife lumens 102 that extend axially through the wall of the cutter housing 100. As can be seen in FIG. 3, for example, the plurality of knife lumens 102 may be spaced equally around the circumference of the cutter housing 100. In the non-limiting embodiment depicted in FIG. 3, a total of eight (8) knife lumens 102 are equally spaced around the circumference of the cutter housing 100. As can be seen in FIGS. 2 and 4, each knife lumen 102 has a curved distal end portion 104 that opens radially outward.

In various non-limiting embodiments, a flexible knife member 120 is slidably received within each knife lumen 102. Each flexible knife member 120 has a sharpened distal end 122 and is attached to or protrudes from a knife ring 123. A pair of knife actuator rods 125 are attached to the knife ring 123 by a slip joint arrangement 127 that permits the knife ring 123 to rotate relative to the actuator rods 125. See FIG. 2A. As can be seen in FIG. 2C, the knife actuator rods 125 (only one knife actuator rod 125 is shown in that view) are attached to a knife switch 130 that is operably mounted to the handle 12. The distal end 122 of each knife member 120 is substantially pointed to enable it to pierce through tissue and it may have at least one cutting edge 124 formed thereon. When the knife switch 130 is moved in the distal direction (arrow 132), the knife members 120 are moved distally within the knife lumens 102 such that the sharpened distal end 122 "naturally" flexes or bends radially out of the curved distal end portion 104 of the lumen 102 as shown in FIG. 4. As used in this context, the term "naturally" means that the material may be prestressed or otherwise formed such that the distal end thereof flexes or bends as it exits the lumen. Likewise, movement of the knife switch 130 in the proximal direction (represented by arrow 134 in FIGS. 1 and 2C) causes each knife member 120 to be retracted back into its knife lumen 102. In various non-limiting embodiments, the knife members 120 may be fabricated from, for example, Nitinol, 300 or 400 series stainless steel (fully or three-fourths hardened).

As can also be seen in FIG. 2A, the firing shaft assembly 50 has a distal end post 140 that protrudes from the base portion 51 and coaxially extends within the cutter housing 100 for selective axial travel therein. Various embodiments also include a bulkhead member 141 that is mounted within the outer sheath 116. To facilitate easy assembly, the outer sheath 16 may comprise a distal outer sheath segment 16 and a proximal outer sheath segment 16' as shown in FIG. 2A. In addition, a distal end post 142 extends from the bulkhead 51 and supports a distal anvil connector 150. The distal anvil connector 150 is coupled to a distal band assembly 151. The distal band assembly 151 is coupled to a control rod assembly 153 that interfaces with an adjustment knob 160 that is rotatably supported on the handle assembly 12. Such anvil shaft assemblies and control knob arrangements are generally known. For example, the control rod assembly and control knob may be configured as disclosed in published U.S. Patent Application No. US 2008/0078806 A1, entitled "Surgical Stapling Instrument With Mechanical Indicator To Show Levels of Tissue Compression, which has been herein incorporated by reference.

As can be seen in FIG. 2B, each of the housing actuator rods 101 protrude through a corresponding arcuate slot 145 in the bulkhead 141. The slots 145 may be sized to define/limit the amount that the cutter housing 100 may be rotated relative to the central axis A-A. For example, in one embodiment wherein a total of eight (8) knife members 120 are employed, the slots 145 may be sized to facilitate at least approximately 45°-50° of arcuate or rotational travel of the cutter housing 100 about the central axis A-A. The bulkhead 141 may further have an aperture 146 for permitting the distal band assembly 151 to protrude therethrough. In addition, each of the knife actuator rods 125 extends through a corresponding opening 147 in the bulkhead 141. Similarly, each of the acquisition rods 83 extend through a corresponding aperture 148 in the bulkhead 141. See FIG. 2B.

Figure 5:
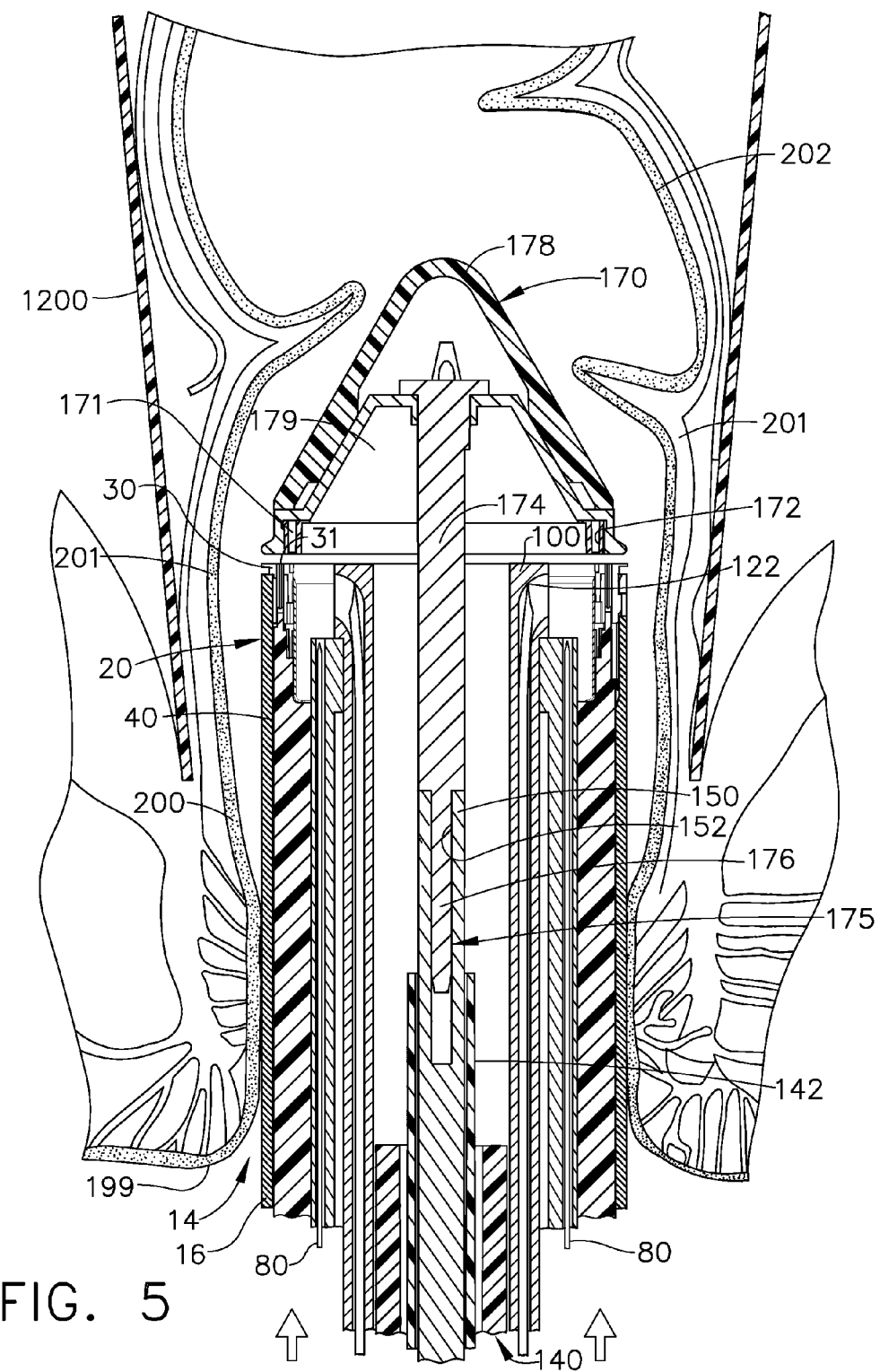
FIG. 5 is a partial cross-sectional view of the distal end of the elongated shaft with an anvil coupled thereto and inserted into a portion of a patient's tubular organ such as a colon.
Figure 6:
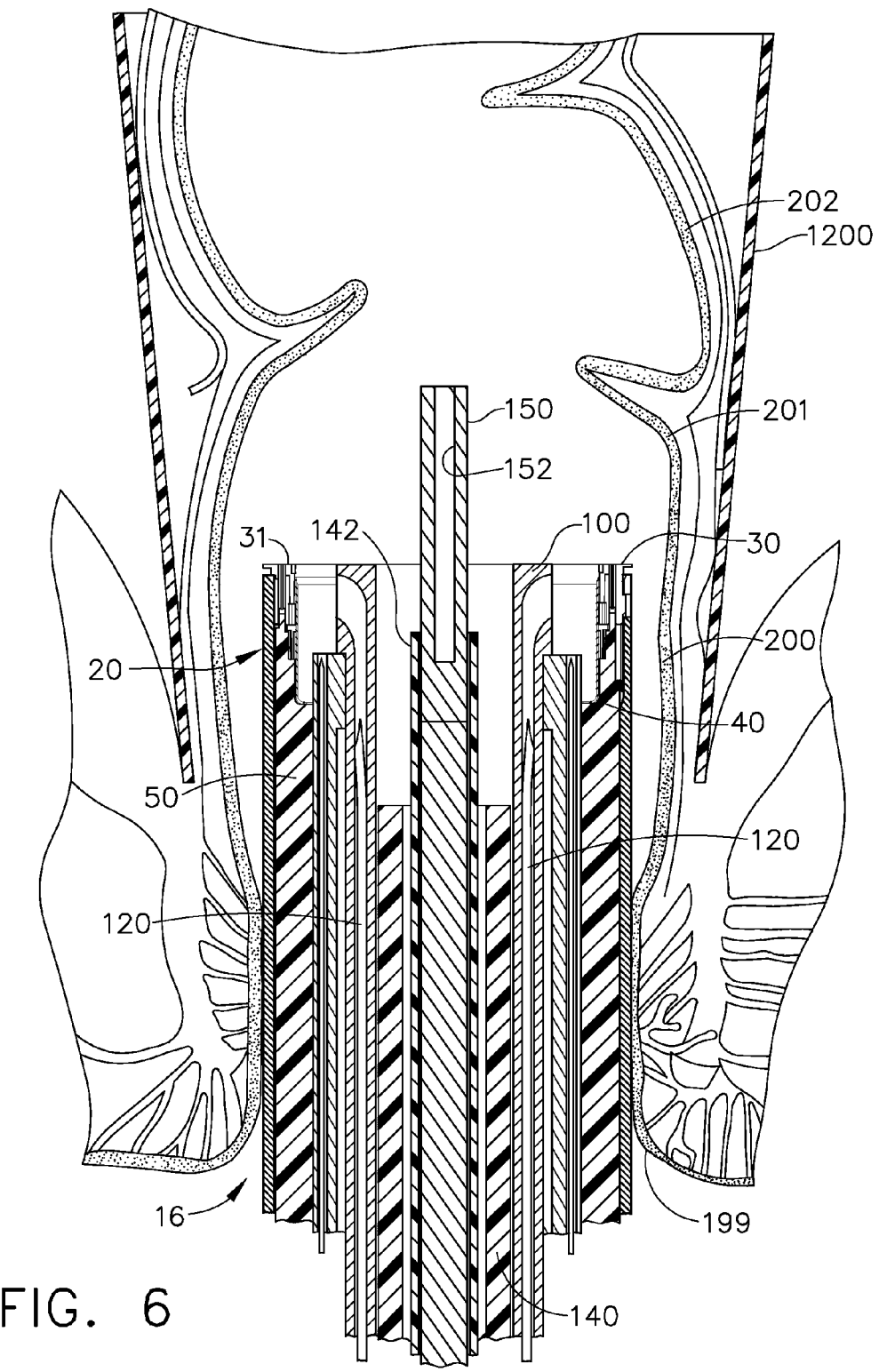
FIG. 6 is another cross-sectional view of the distal end of the elongated shaft of FIG. 5 with the anvil removed therefrom.
Figure 13:
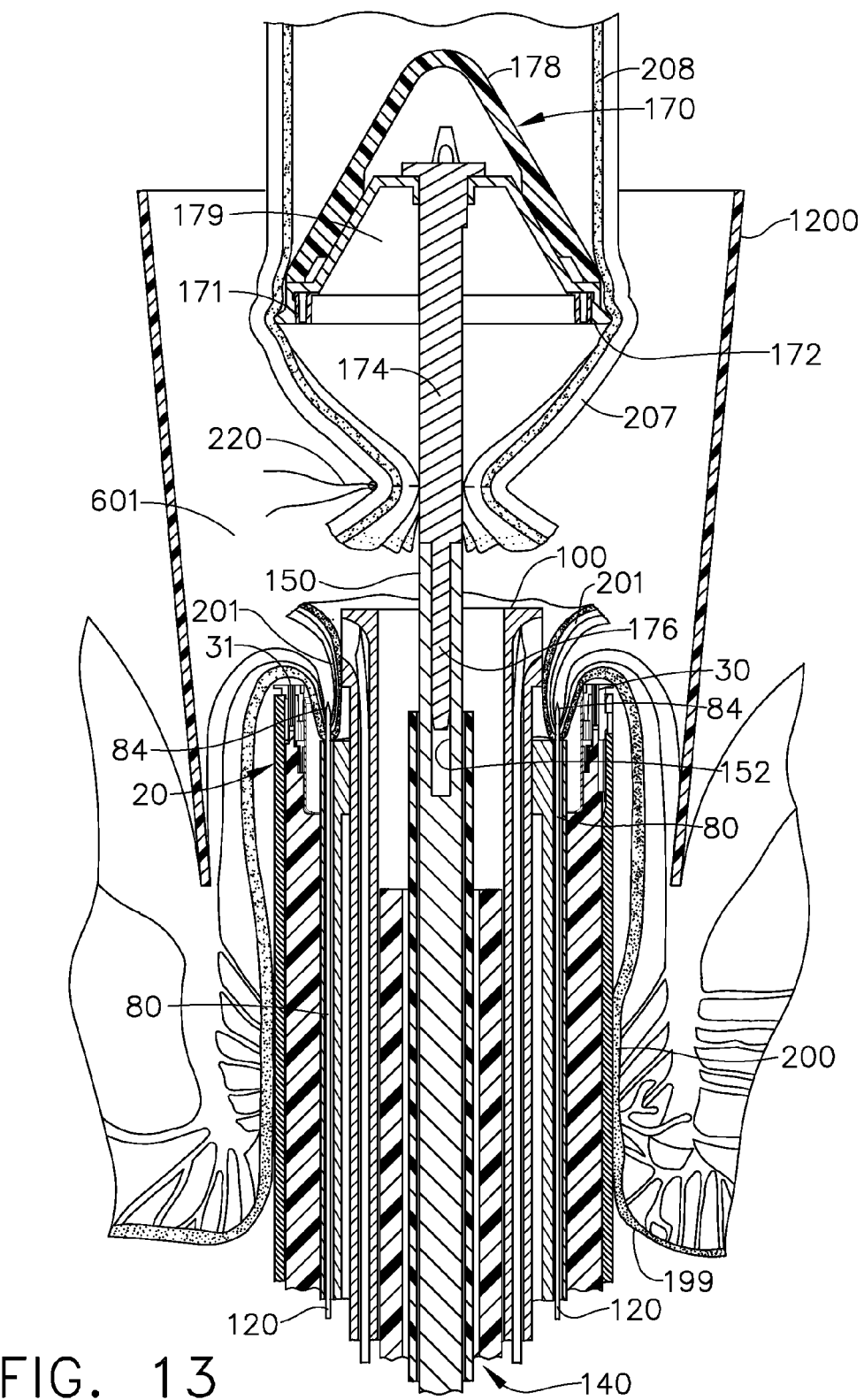
FIG. 13 is another cross-sectional view of the distal end of the elongated shaft of FIG. 12 after an anvil has been secured to a distal portion of the colon and the anvil stem thereof has been coupled to the anvil assembly portion of the circular stapling instrument.

The circular stapler 10 further includes an anvil 170 as shown in FIG. 5. In various non-limiting embodiments, the anvil 170 includes an anvil base 171 that has a series of staple forming pockets 172 therein and an anvil shaft 174 that is removably attachable to the distal anvil connector 150. In particular, a coupling stem 176 protrudes from the proximal end 175 of the anvil shaft 174 and is sized to be slidably received in a passage 152 in the distal anvil connector 150. The anvil 170 further has an anvil cap 178 thereon as illustrated in FIGS. 5 and 13 that defines a tissue cavity 179 therein.

One exemplary method of using the circular stapler 10 will be described with reference to FIGS. 5-16. The various embodiments of the circular stapler 10 are particularly well-suited for performing a circular anastomosis of a tubular organ such as, for example, the colon. Turning first to FIG. 5, the stapler head 20 is inserted into a proximal portion 201 of the colon 200 through the patient's anus 199. In applications wherein a diseased or targeted portion 202 of colon is to be removed, the stapler head 20 is positioned adjacent to the diseased portion 202. See FIG. 6.

Figure 7:
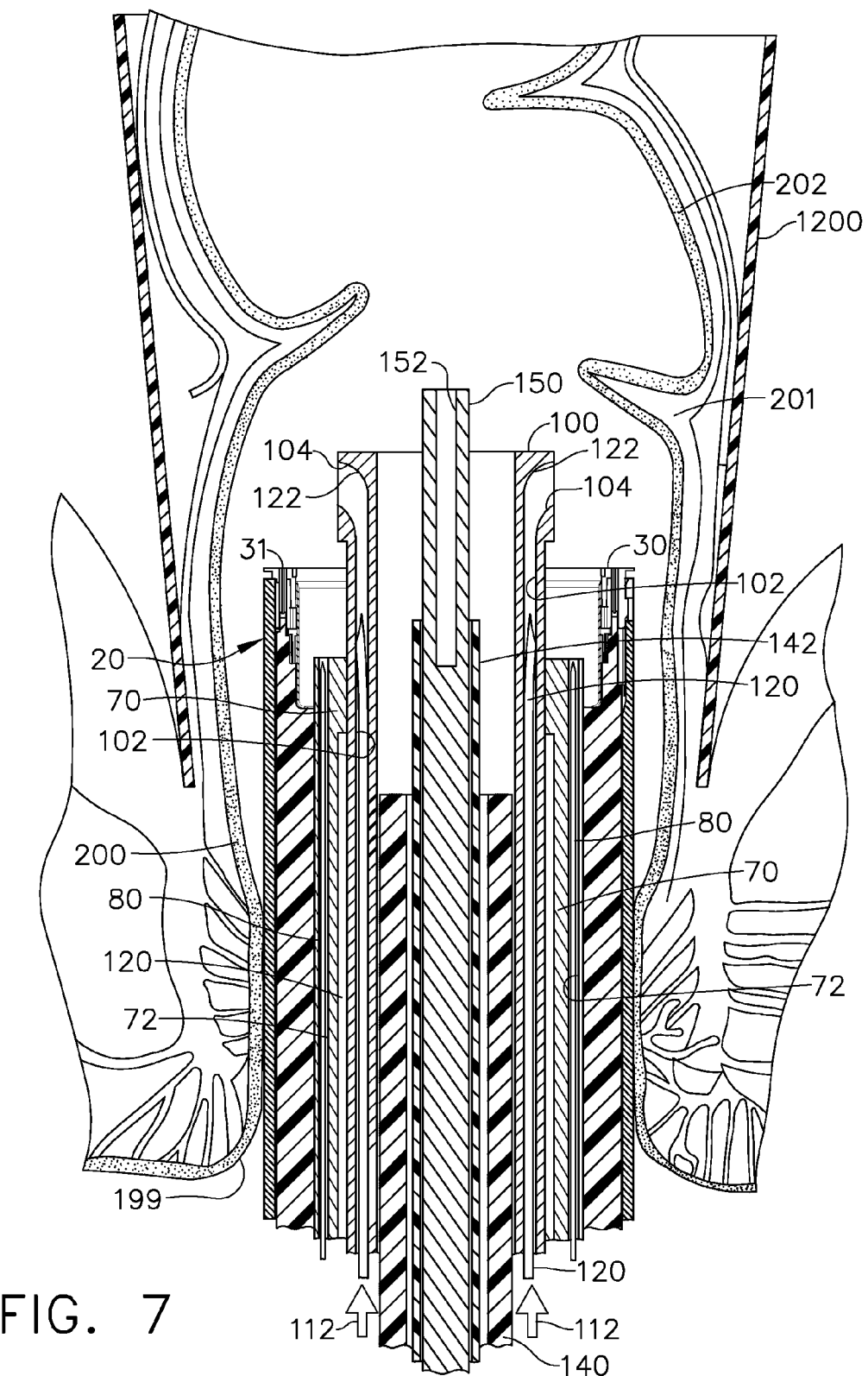
FIG. 7 is another cross-sectional view of the distal end of the elongated shaft of FIGS. 5 and 6 with the distal end portion of the cutter housing being axially advanced beyond the distal face of the staple cartridge supported in the distal end of the elongated shaft.
Figure 8:
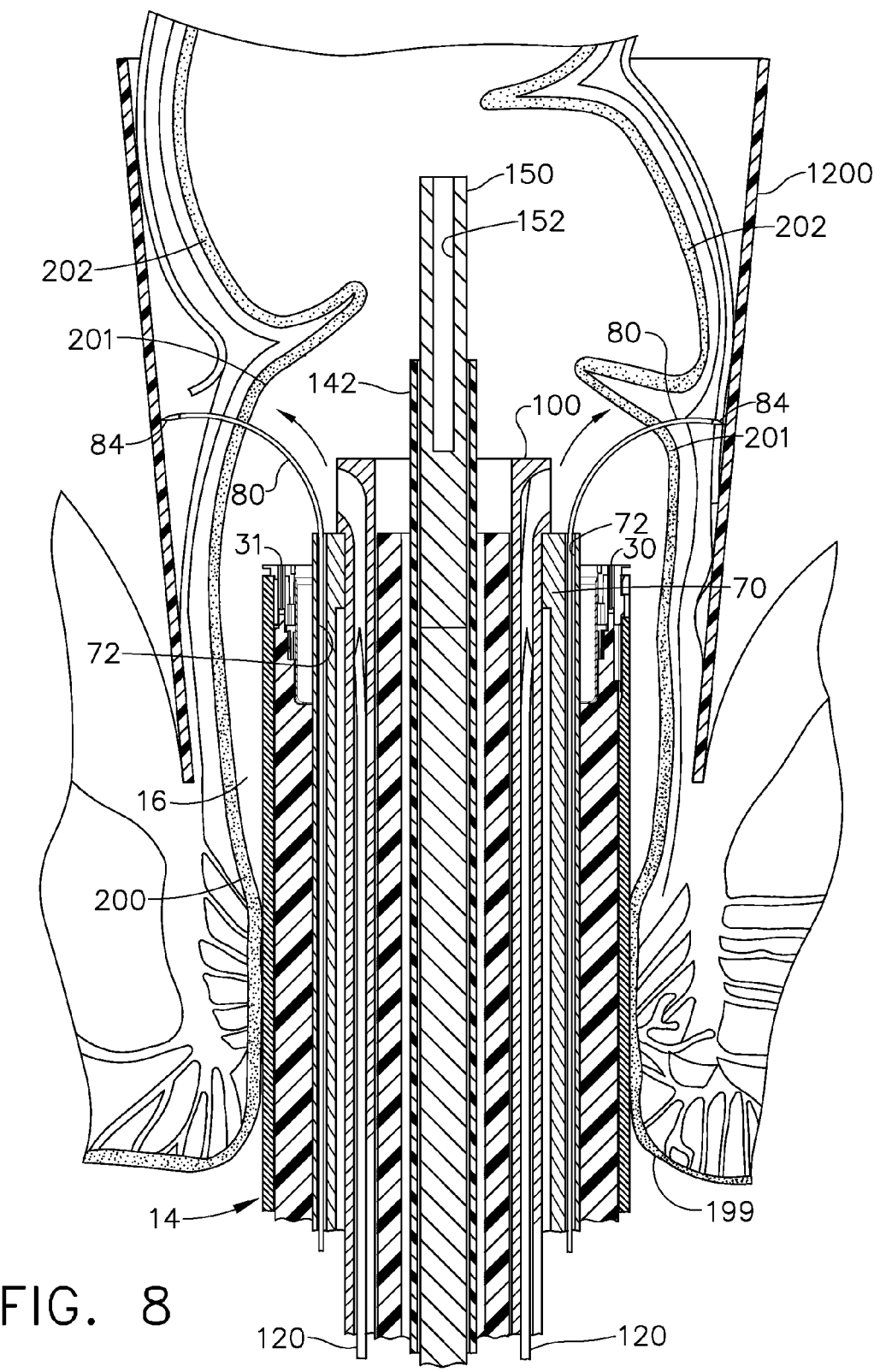
FIG. 8 is another cross-sectional view of the distal end of the elongated shaft of FIG. 7 with tissue acquisition members being radially deployed out of the tissue acquisition housing and piercing through a portion of the colon.

Once the stapler head 20 has been inserted to the appropriate position relative to the diseased portion 202, the cutter housing 100 is advanced distally by axially advancing the knife knob 110 in a distal direction (represented by arrows 112 in FIGS. 1 and 7). At this stage in the procedure, the knife members 120 have not been advanced out of their respective knife lumens 102. Thereafter, the surgeon advances the acquisition housing 70 distally by moving the hook switch 90 in the distal direction (arrow 92 in FIG. 1). Movement of the acquisition housing 70 in the distal direction causes the hook members 80 to move axially out of their respective acquisition lumens 72. As the distal ends of the hook members 80 exit their respective acquisition lumens 72, they naturally flex radially outward to engage and pierce through the proximal portion 201 of the colon 200. See FIG. 8. Once the hook members 80 have pierced and engaged the proximal portion 201 of the colon 200, the surgeon moves the hook switch 90 in the proximal direction (represented by arrow 94 in FIG. 1) to retract the hook members 80 into their respective acquisition lumens 72 as well as to retract the acquisition housing 100 back to its starting position. The barbs 84 on the distal ends of the hook members 80 draw the engaged the proximal portion 201 into the position illustrated in FIG. 9. Thus, the engaged proximal portion 201 of the colon 200 is drawn over a distal face 31 of the staple cartridge 30 and partially into the interior space 33 between the staple cartridge 30 and the cutter housing 100.

Figure 9:
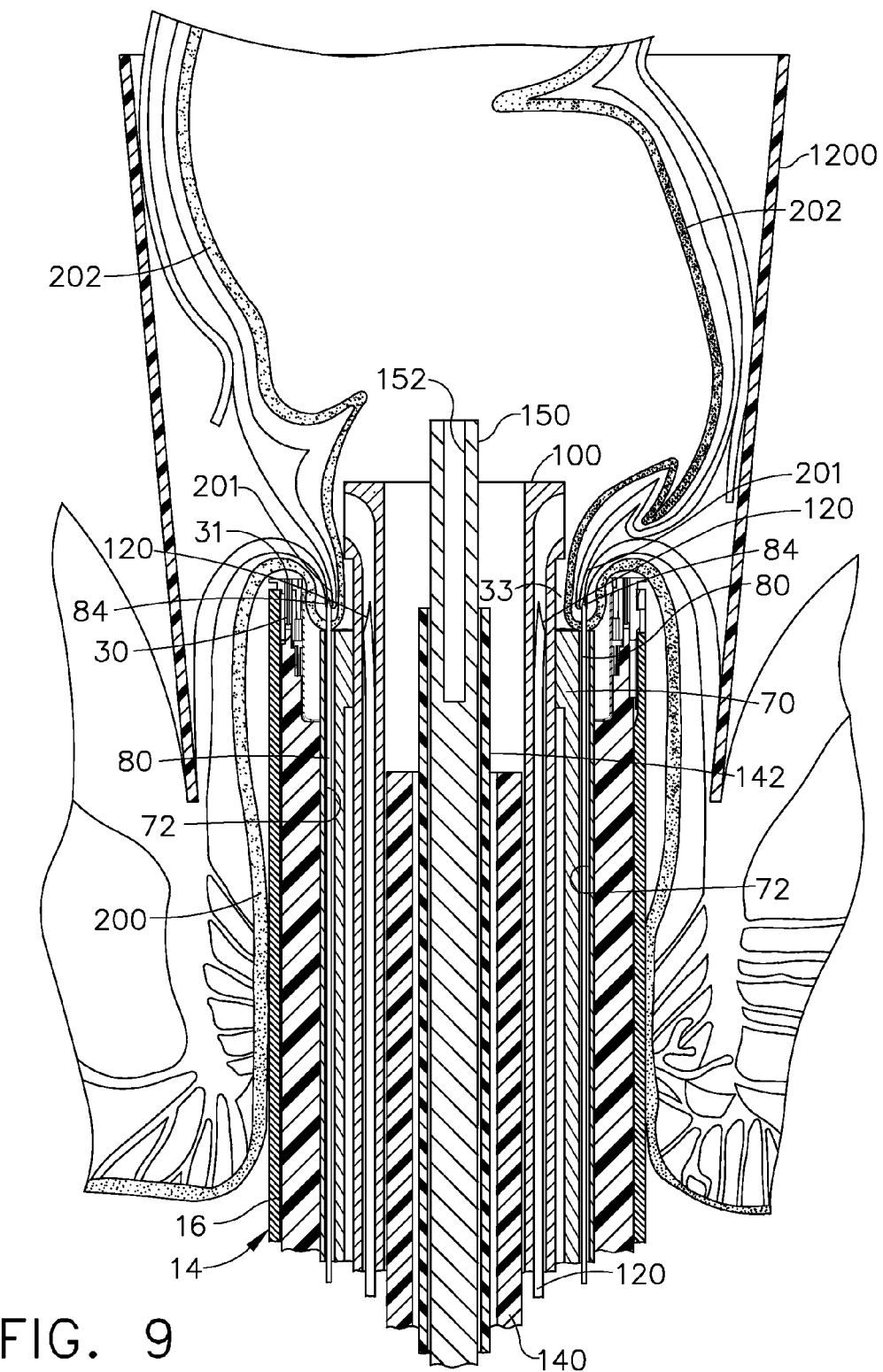
FIG. 9 is another cross-sectional view of the distal end of the elongated shaft of FIG. 8 with the tissue acquisition members thereof being withdrawn back into the tissue acquisition housing to position the punctured portion of the colon adjacent to the distal face of the staple cartridge.
Figure 10:
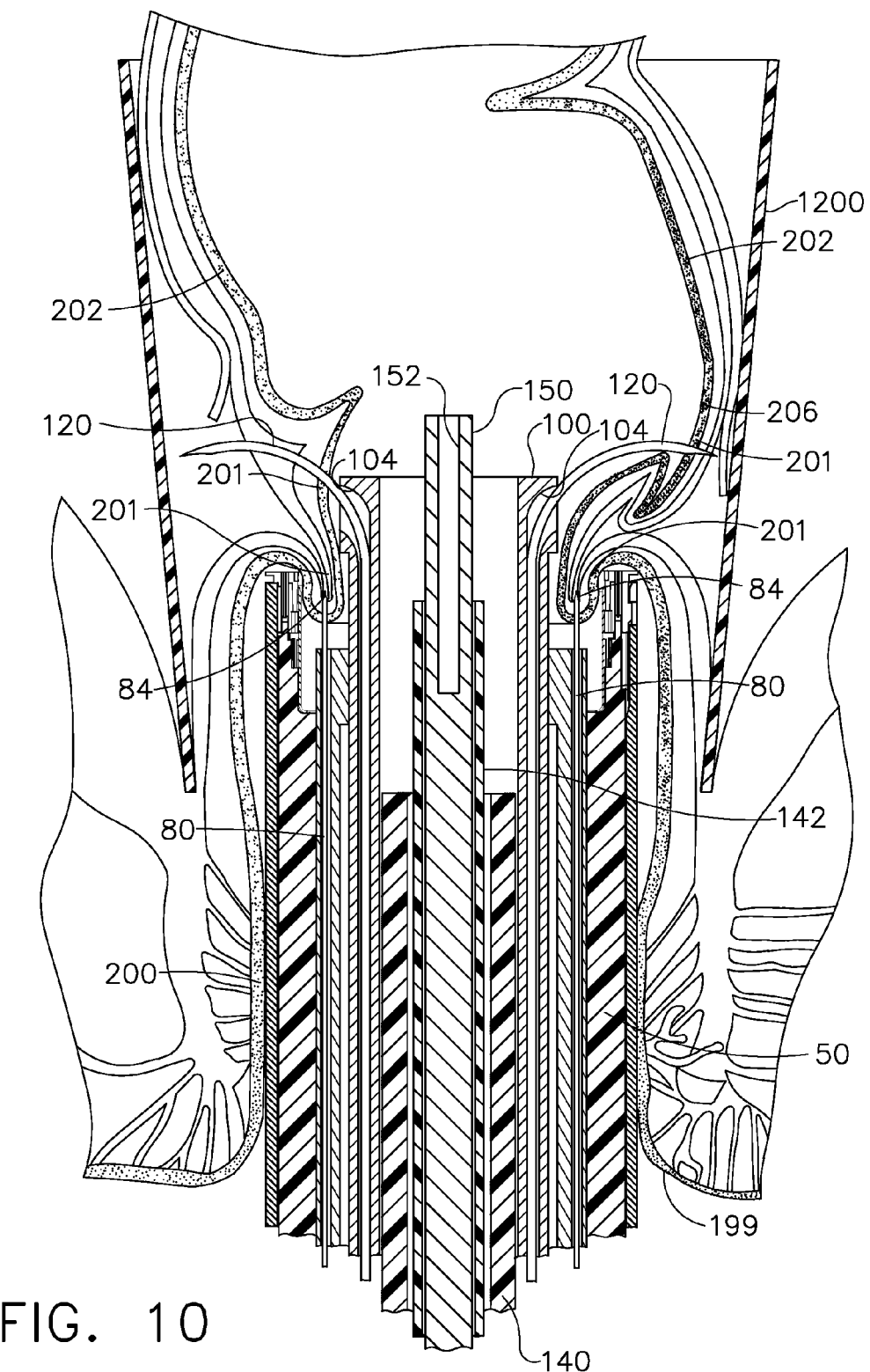
FIG. 10 is another cross-sectional view of the distal end of the elongated shaft of FIG. 9 with the knife members radially deployed out of the cutter housing and puncturing through another portion of the colon.
Figure 11:
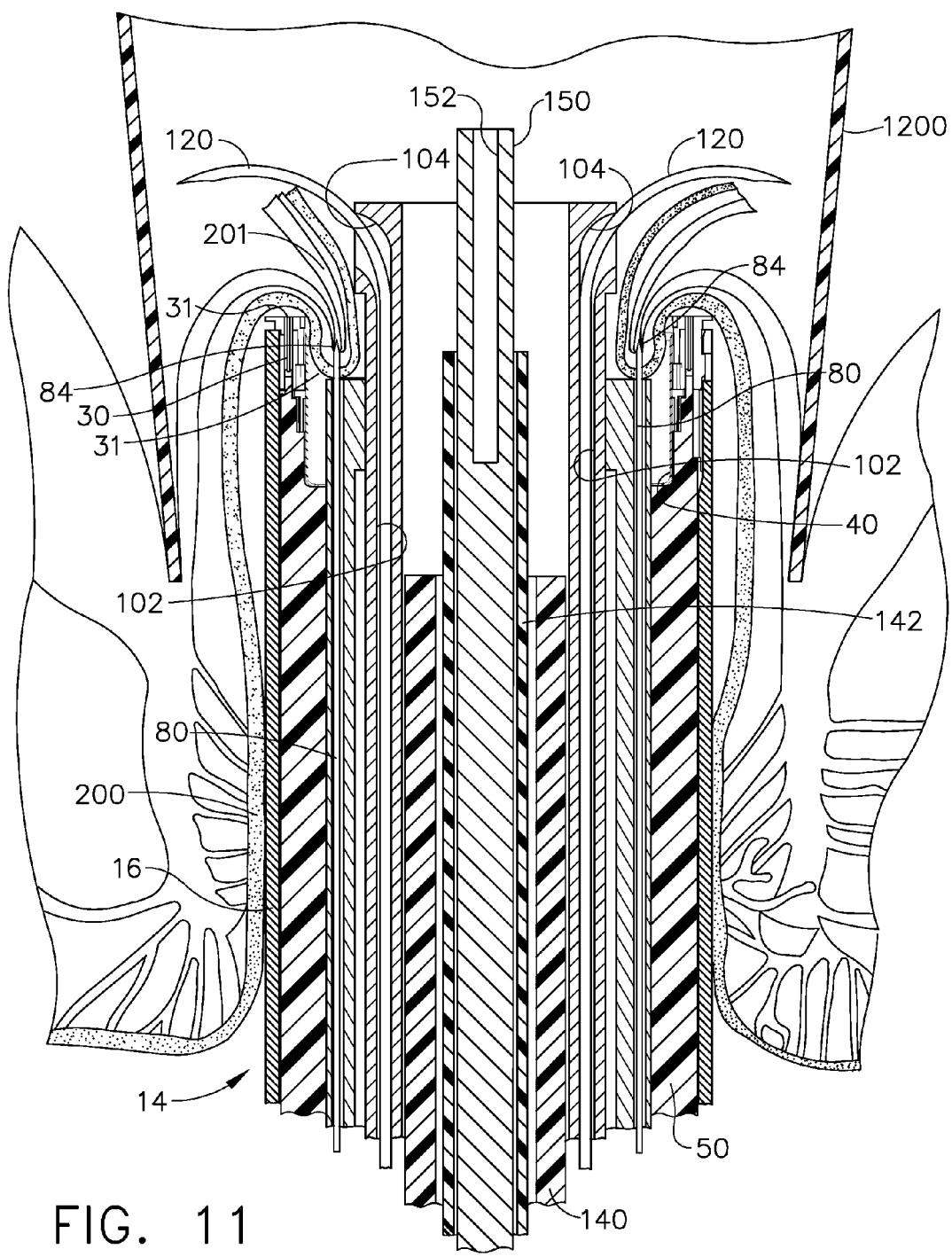
FIG. 11 is another cross-sectional view of the distal end of the elongated shaft of FIG. 10 after the knife members have been rotated to sever the retained punctured portion of colon from a diseased portion of the colon.
Figure 12:
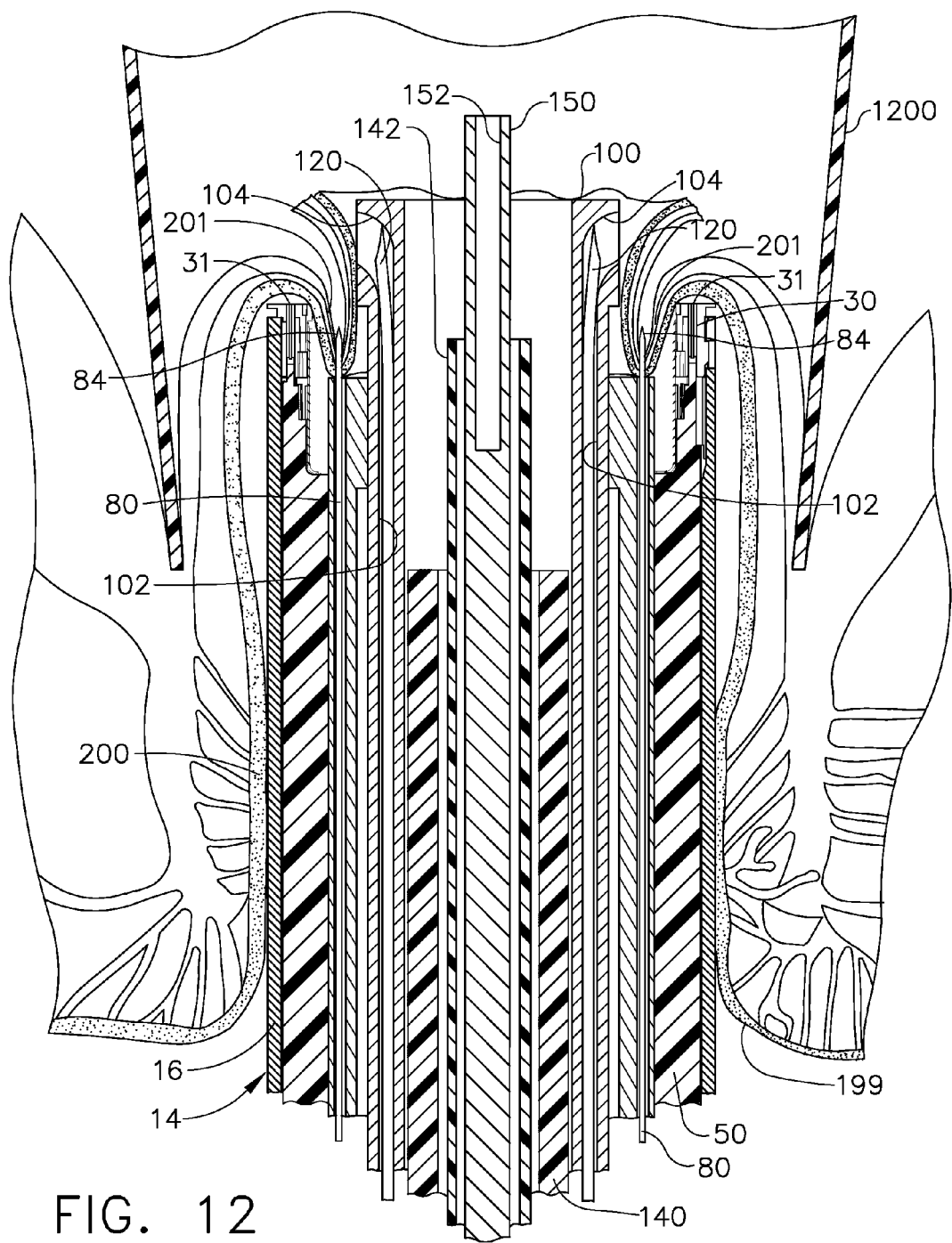
FIG. 12 is another cross-sectional view of the distal end of the elongated shaft of FIG. 11 with the knife members withdrawn back into their respective lumens in the cutter housing.

Once the engaged proximal portion 201 of the colon 200 has been drawn into the position illustrated in FIG. 9, the surgeon then extends the knife members 120 out of their respective knife lumens 102 by axially advancing the knife knob 110 on the handle assembly 12 in the distal direction (represented by arrow 112 in FIG. 1). By moving the knife knob 110 distally, the knife members 120 are advanced out of their knife lumens 102 and the curved portion 104 of each knife lumen 102 causes the knife member 120 therein to move radially outward as illustrated in FIG. 10. The knife members 120 protrude through the proximal portion 201 of the colon 200 that is proximal to the diseased colon portion 202. See FIG. 10. Thereafter, the diseased colon portion 202 may be severed from the proximal colon portion 201 by rotating the knife knob 110 on the handle assembly 12 (represented by arrow 116 in FIG. 1). Rotation/actuation of the knife knob 110 will cause the cutter housing 100 and the knife members 120 to rotate about the central axis A-A and cut through the colon tissue. After the diseased portion 202 has been cut away from the proximal colon portion 201 (FIG. 11), the surgeon may retract the knife members 120 back into their respective knife lumens 102 by moving the knife knob 110 in a proximal direction (represented by arrow 114 in FIG. 1). See FIG. 12.

The diseased portion 202 may be severed from the distal colon portion 208 (FIG. 13), by means of, for example, a conventional laparoscopic tissue severing device (not shown) that has been inserted through a trocar sleeve that extends into the abdominal cavity 601 that is adjacent to the diseased portion 202. The diseased colon portion 202 may then be removed through the trocar sleeve. The surgeon then orients the anvil 170 within the distal colon portion 206 such that the anvil shaft 174 protrudes out of the distal colon portion 206 as shown in FIG. 13. The surgeon then ties the end of the distal colon portion 206 around the anvil shaft 174 using what is known in the art as a "purse string suture" 220. Once the distal colon portion 206 has been sutured around the anvil shaft 174, the coupling stem 176 of the anvil shaft 174 is inserted into the passage 152 in the anvil shaft assembly 150. The coupling stem 176 may be sized relative to the passage 152 to establish a frictional fit therebetween to retain the coupling stem 176 therein, yet permit the coupling stem 176 to be removed therefrom at a later time.

Figure 14:
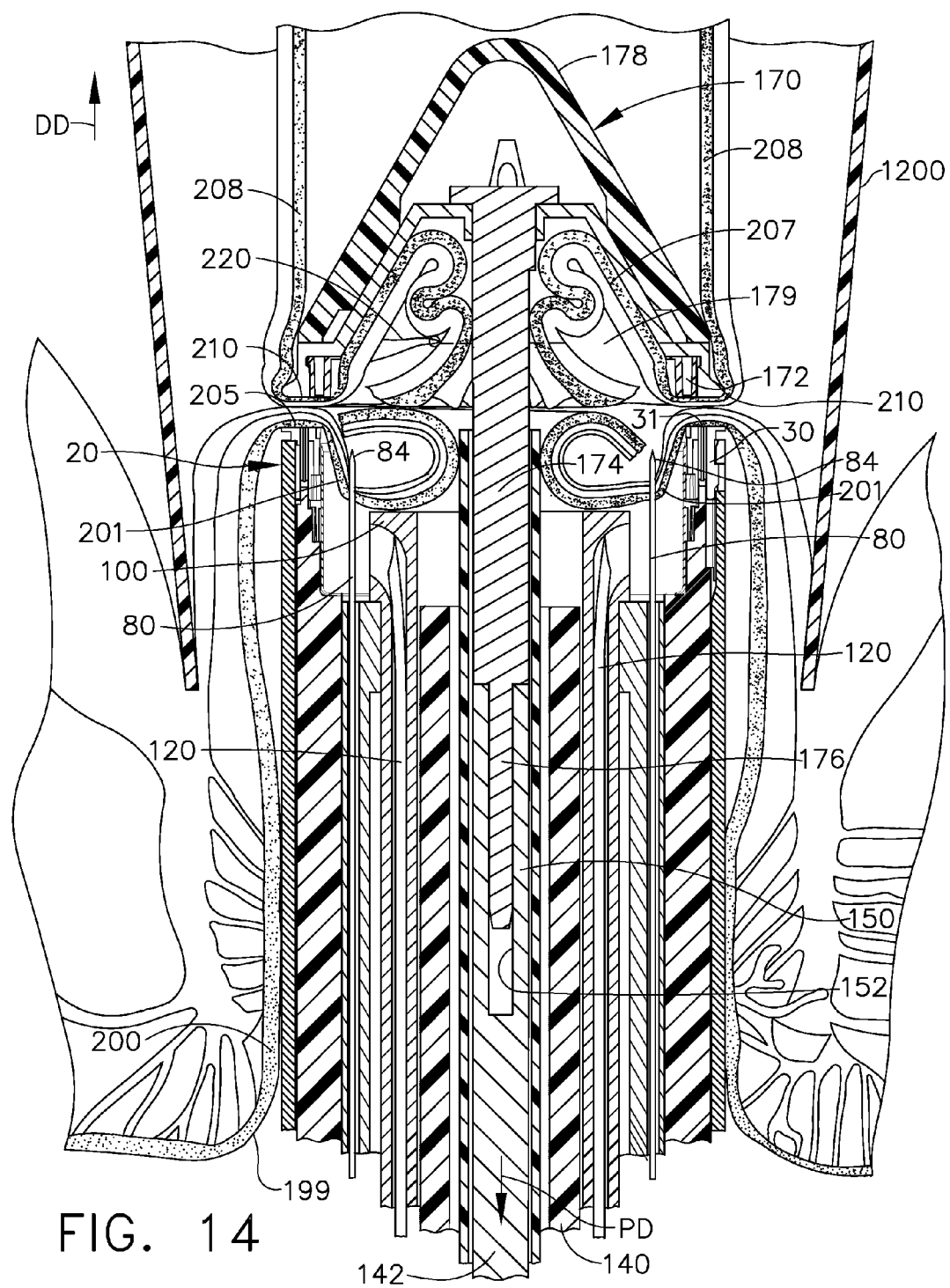
FIG. 14 is another cross-sectional view of the distal end of the elongated shaft of FIG. 13 after the anvil has been drawn adjacent to the distal face of the staple cartridge.
Figure 15:
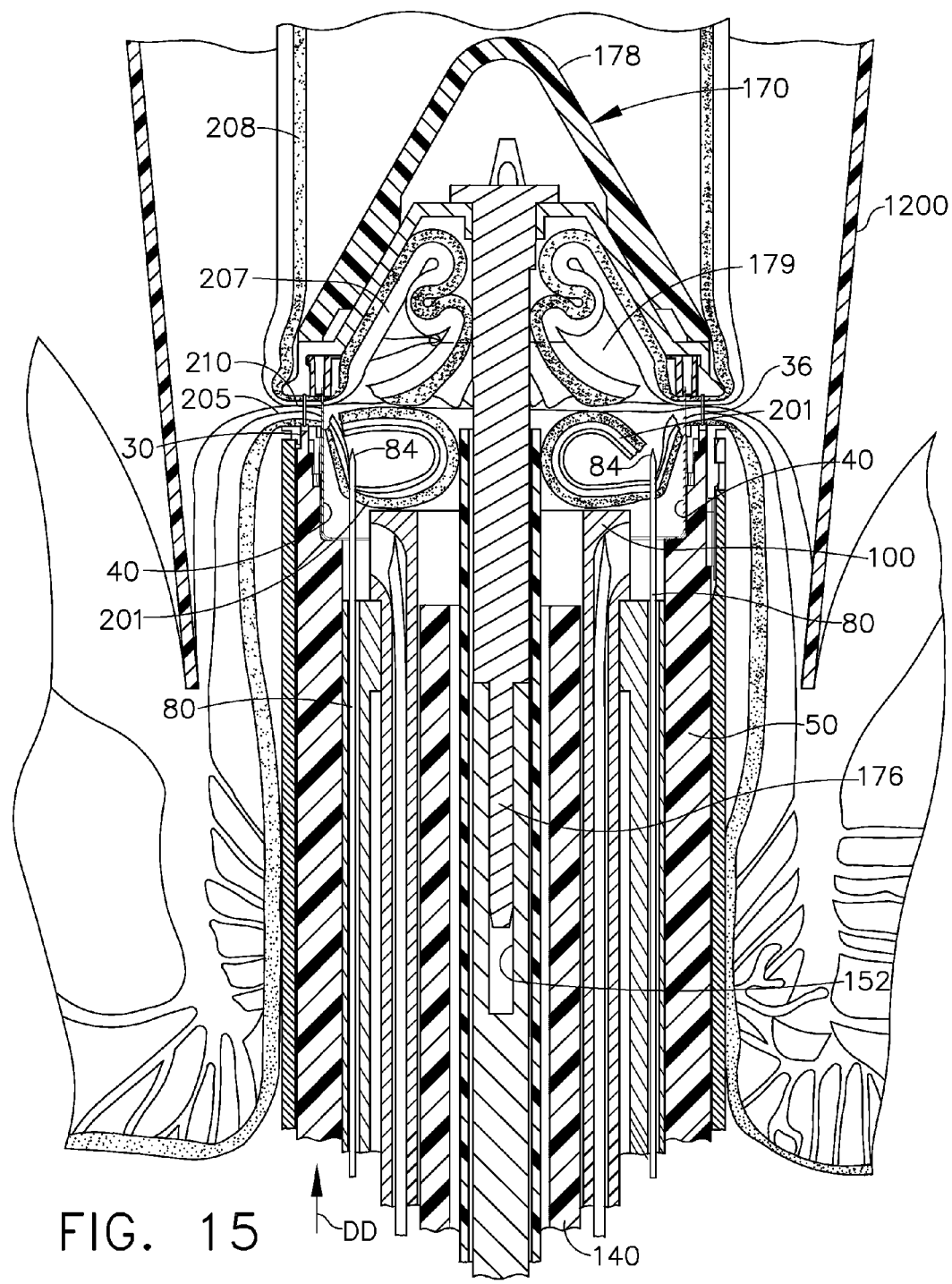
FIG. 15 is another cross-sectional view of the distal end of the elongated shaft of FIG. 14 after the staples have been deployed and annular knife has been axially advanced through the adjacent portions of colon.
Figure 16:
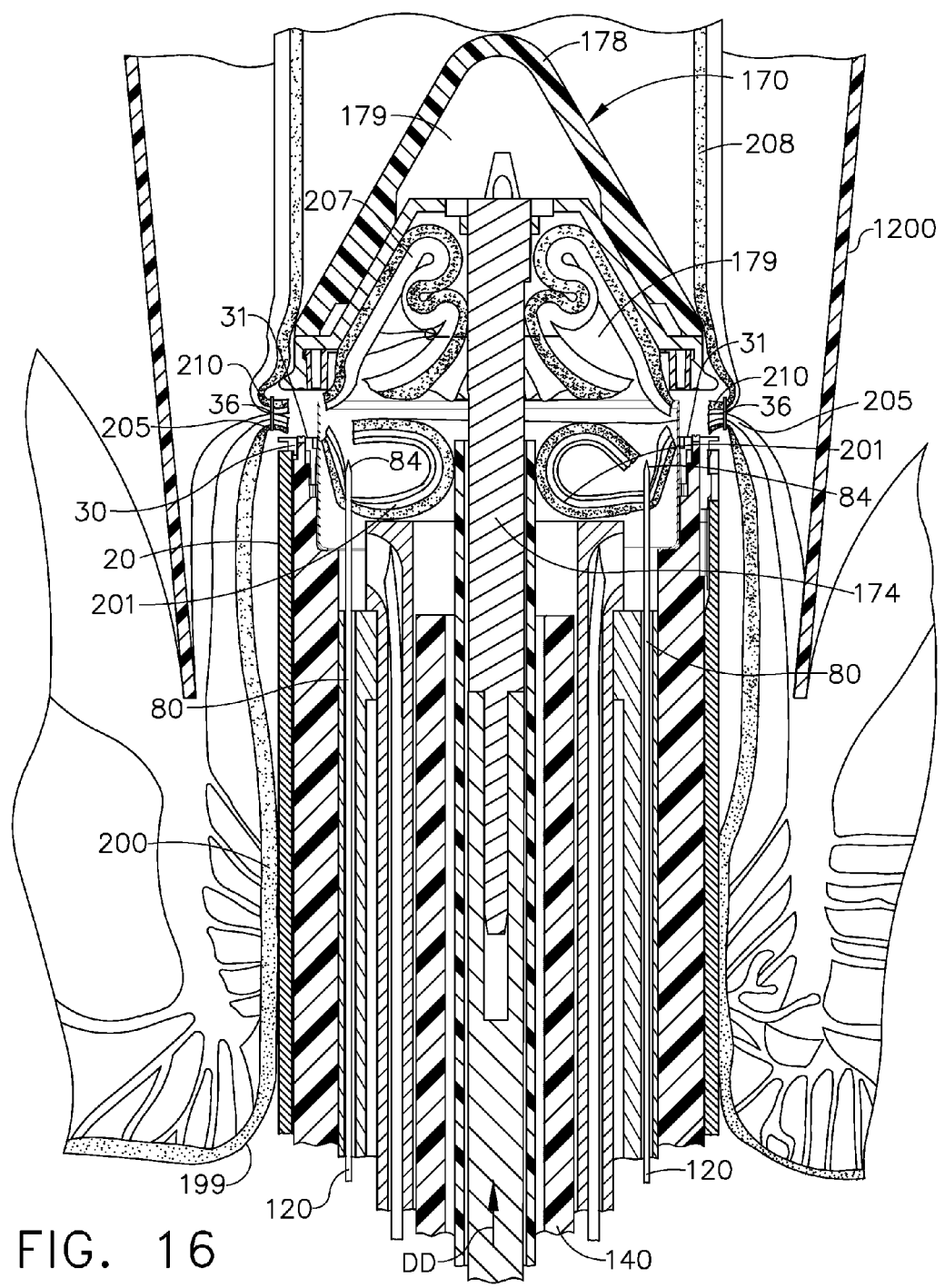
FIG. 16 is another cross-sectional view of the distal end of the elongated shaft of FIG. 15 after the colon sections have been stapled together, but prior to being withdrawn from the colon.

The surgeon then draws the anvil 170 toward the stapler head 20 (in the proximal direction "PD") by rotating the anvil control knob 160 in the appropriate direction until colon portions 205, 210 are clamped between the anvil 170 and the staple cartridge 30 as shown in FIG. 14. Thereafter, the surgeon actuates the firing trigger 60 to axially advance the firing shaft assembly 50 in the distal direction "DD". As firing shaft assembly 50 is advanced distally, the outer staple driver portion 54 and the inner staple driver portion 56 serve to drive the staples 36 located in the outer row 32 and inner row 34, respectively, through the colon portions 205, 210 into the anvil forming pockets 172 in the anvil base 171. The firing shaft assembly 50 also advances the annular knife 40 through the colon portion 205 to cut the portion 201 therefrom. See FIG. 15. Further advancement of the annular knife 40 severs colon portion 207 from colon portion 208. The surgeon then moves the anvil 170 in the distal direction "DD" to release the stapled colon portions 205, 210 from between the anvil base 171 and the face 31 of the staple cartridge 30. See FIG. 16. The instrument 10 may then be removed from the colon 200. The cut portion 201 remains in the stapler head 20 and the cut portion 207 remains in the tissue cavity 179 in the anvil 170 as the surgeon withdraws the instrument 10 out through the patient's anus 199. Thus, the cut portions 201, 207 of the colon 200 are removed from the repaired colon when the instrument is withdrawn therefrom.

Figure 17:
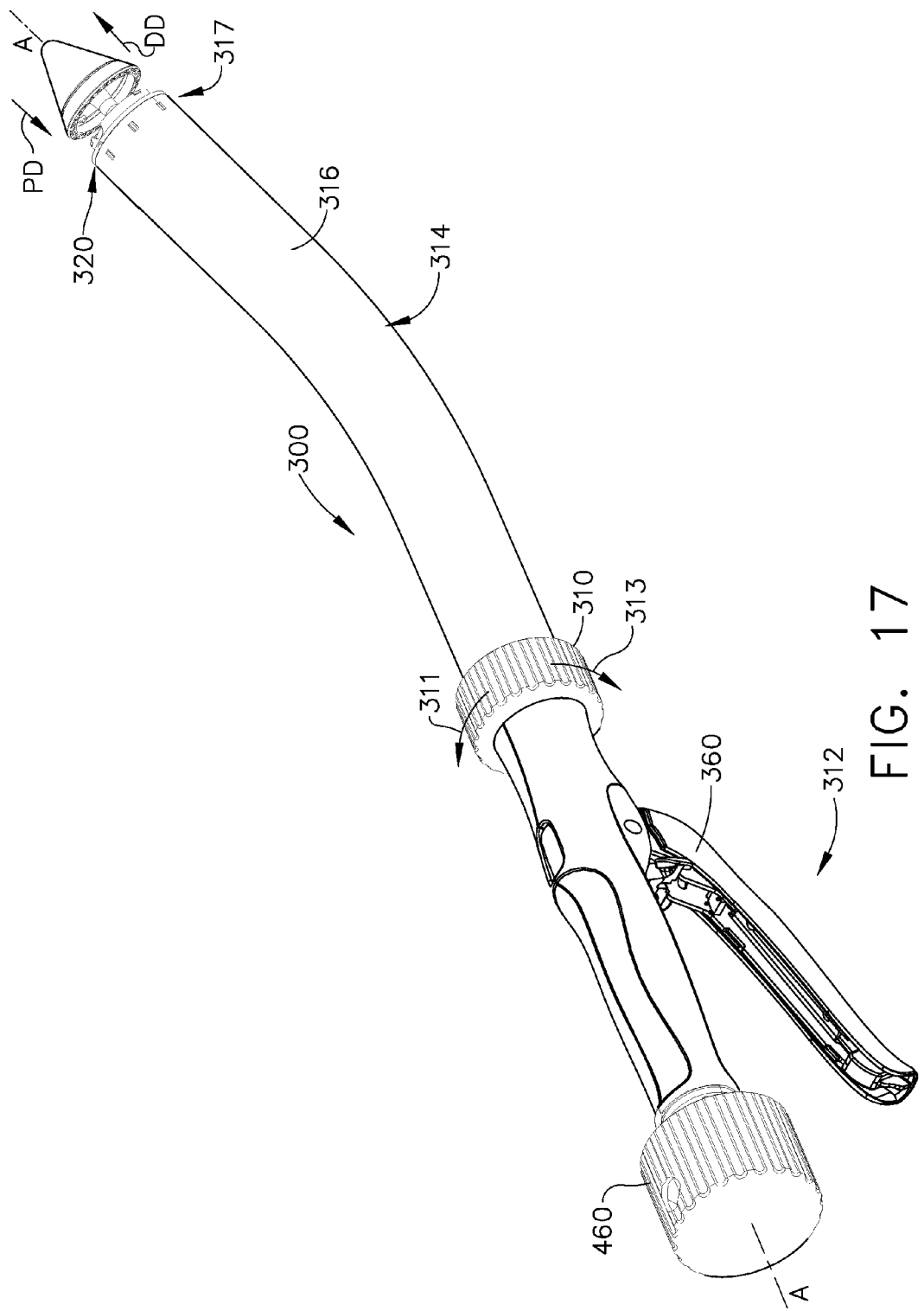
FIG. 17 is a perspective view of a surgical circular stapling instrument of various non-limiting embodiments of the present invention.

FIG. 17 illustrates another circular stapler 300 according to various non-limiting embodiments of the invention. The circular stapler 300 generally includes a handle assembly 312 that has an elongated shaft 314 protruding therefrom. The elongated shaft 314 may define a central axis A-A. As can be seen in FIG. 17, the elongate shaft 314 includes a rigid outer sheath 316 that supports a stapler head 320 thereon. In various non-limiting embodiments, the stapler head 320 is configured to support a circular staple cartridge 330 therein. Such circular staple cartridges 330 are known in the art and generally support one or two or more circumferentially spaced and staggered rows of staples 36 therein as was described hereinabove. A conventional annular knife 340 is coaxially and movably supported within the staple cartridge 330. See FIG. 18.

In certain implementations, the circular stapler 300 further includes a firing shaft 350 that is operably supported within the rigid outer sheath 316 for selective axial travel therein as was discussed above. See FIG. 18. A distal end portion 352 of the firing shaft 350 has an outer staple driver portion 354 thereon for engagement with each of the staples 36 in the outer row 32 of staples 36 in the staple cartridge 330. In addition, the distal end portion 352 of the firing shaft 350 has an inner staple driver portion 356 configured for engagement with each of the staples 36 in the inner row 34 of staples 36 within the staple cartridge 330. As can also be seen in FIG. 18, for example, the distal end portion 352 of the firing shaft 350 further has a flanged portion 358 that is configured to engage the annular knife 340. Thus, as will be discussed in further detail below, axial advancement of the firing shaft 350 in a distal direction "DD", will cause the staples 36 to be driven out of the staple cartridge 330 as well as the annular knife 340 to advanced distally.

In various non-limiting embodiments, the firing shaft 350 interfaces with a firing trigger 360 that is operably coupled to the handle assembly 312. As can be seen in FIG. 17, the firing trigger 360 is pivotally coupled to the handle assembly 312 such that when the firing trigger 360 is pivoted toward the handle assembly 312, the firing shaft 350 is moved in the distal direction DD. As was discussed above, such firing trigger arrangements are known in the art and therefore will not be discussed in detail herein.

Figure 18:
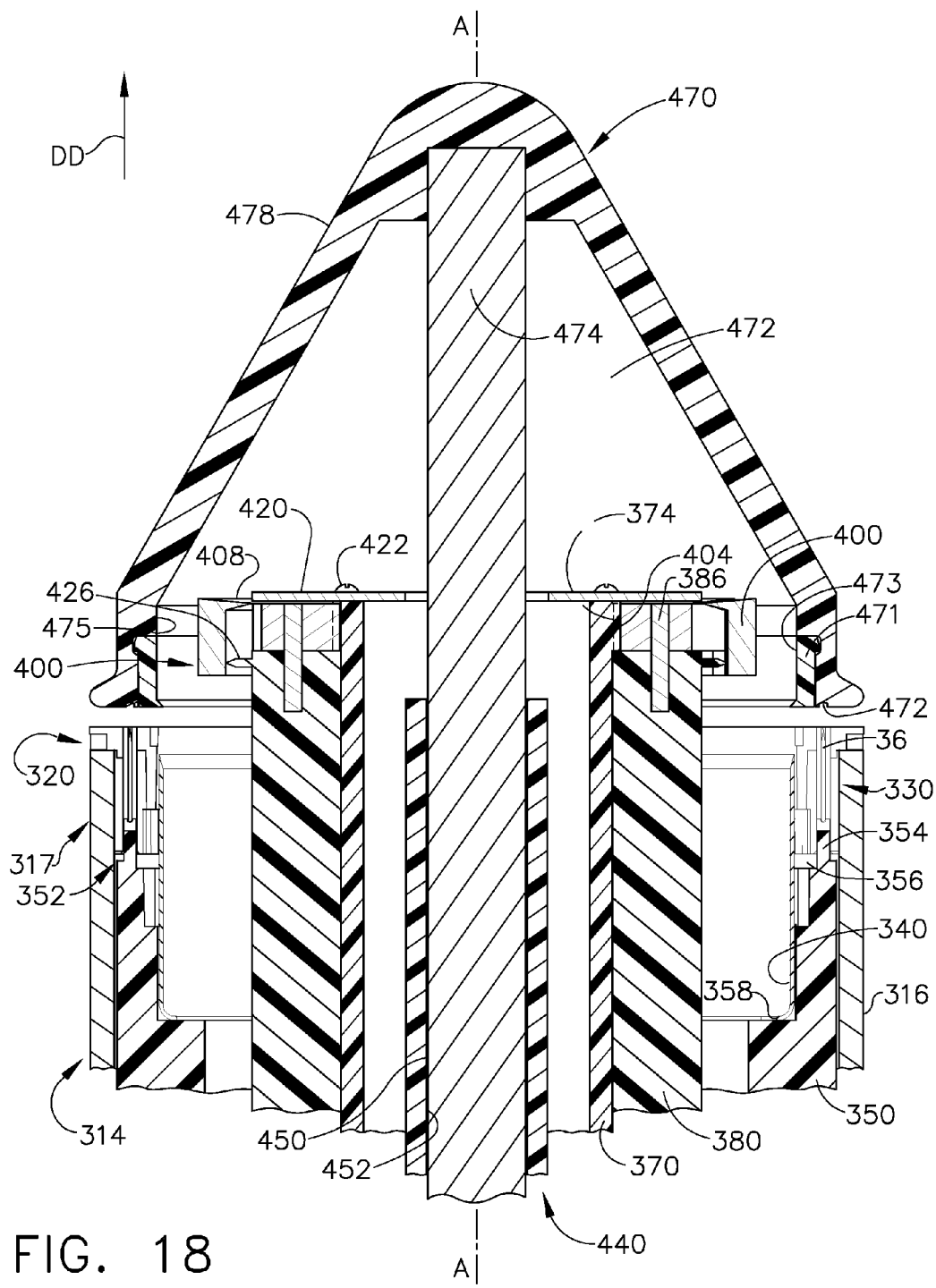
FIG. 18 is a cross-sectional view of a distal end portion of the elongated shaft of the circular stapling instrument of FIG. 17.
Figure 21:
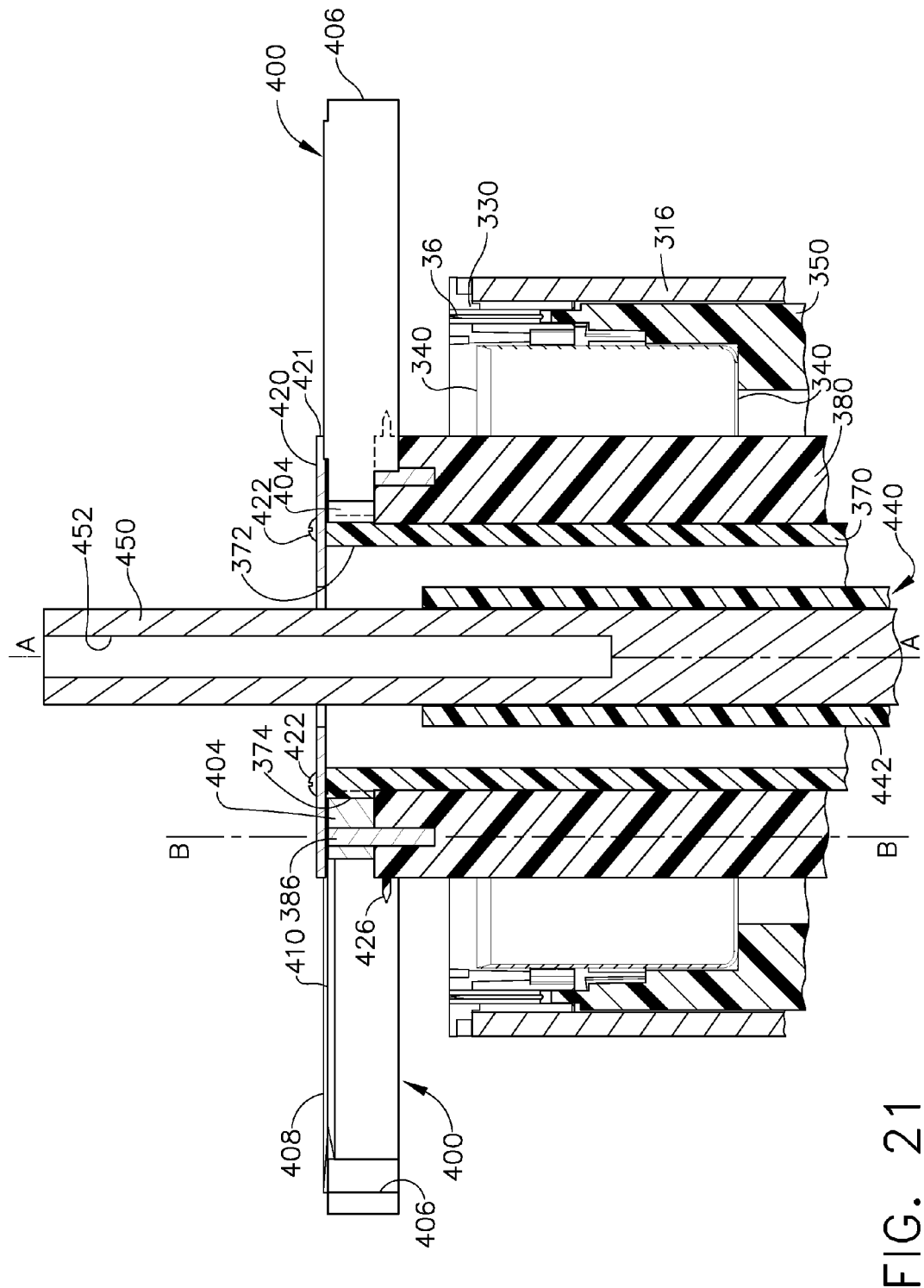
FIG. 21 is a partial cross-sectional view of the acquisition shaft of FIGS. 19 and 20, with the tissue arms thereof in a deployed position.

As shown in FIG. 18, various non-limiting embodiments also include a deployment shaft 370 that is coaxially and rotatably supported within a tissue acquisition shaft 380 that is non-rotatably supported within the elongated shaft 316. The proximal end of the deployment shaft 370 operably interfaces with a tissue acquisition knob 310 that is rotatably supported on the handle assembly 312. The deployment shaft 370 interfaces with the tissue acquisition knob 310 in the manner described above with respect to knife knob 110. Thus, rotation/actuation of the tissue acquisition knob 310 on the handle assembly 312 will result in the rotation of the deployment shaft 370 within the tissue acquisition shaft 380 about the central axis A-A. More specifically and with reference to FIG. 19, in various embodiments, a distal end 372 of the deployment shaft 370 protrudes through a hole 382 in the acquisition shaft 380 and has a drive gear 374 attached thereto. A distal end 384 of the acquisition shaft 380 is configured to operably support at least two tissue acquisition members or tissue arms 400 thereon. In the non-limiting embodiment depicted in FIG. 19, a total of four tissue arms 400 are pivotally pinned to the distal end 384 of the tissue acquisition shaft 380 by corresponding pins 386 such that each tissue arm 400 pivots about a corresponding "acquisition" axis B-B that is substantially parallel to the central axis A-A. See FIGS. 21 and 23.

Figure 19:
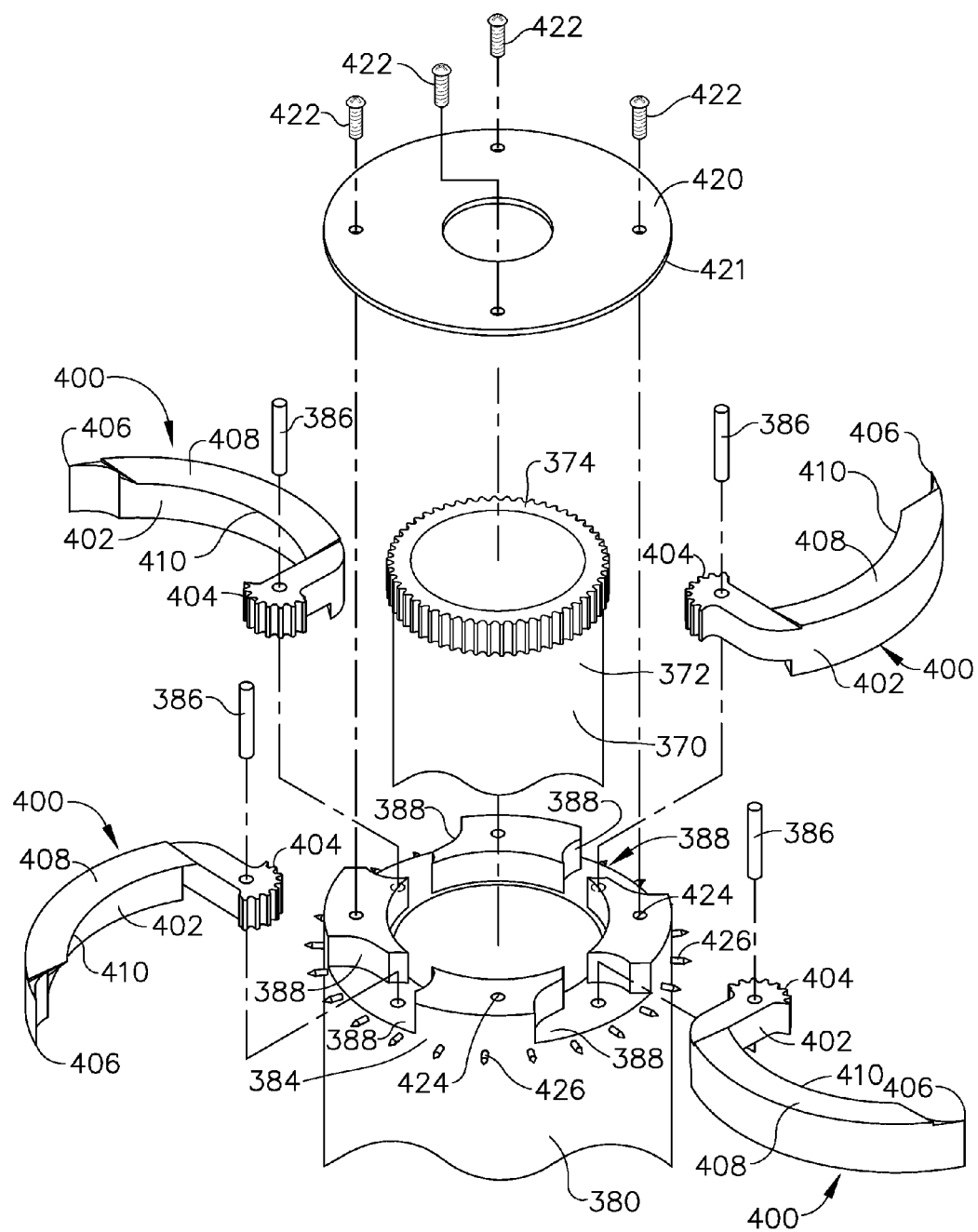
FIG. 19 is an exploded assembly view of the acquisition and deployment shafts of various non-limiting embodiments of the present invention.
Figure 20:
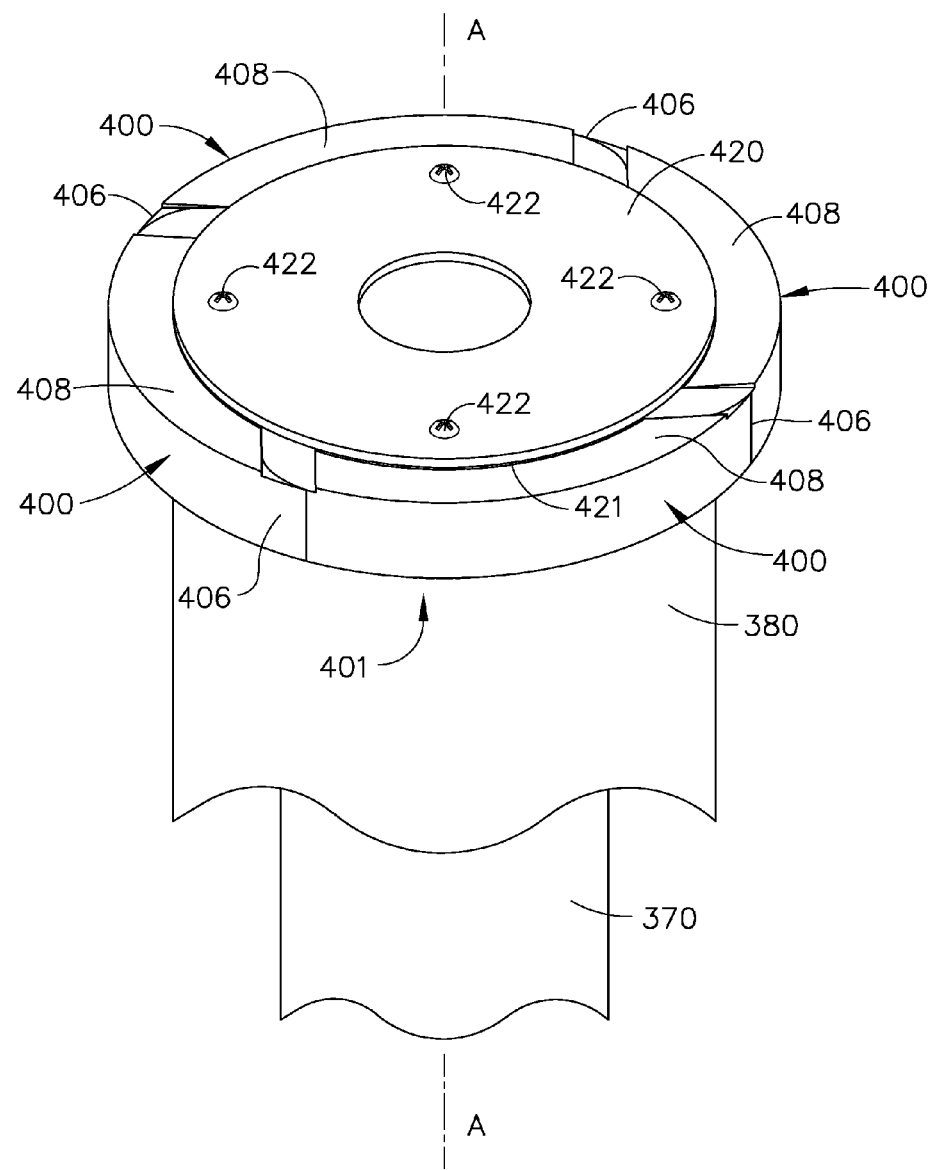
FIG. 20 is a partial perspective view of the acquisition shaft of FIG. 19 with the tissue arms thereof in a retracted position.
Figure 22:
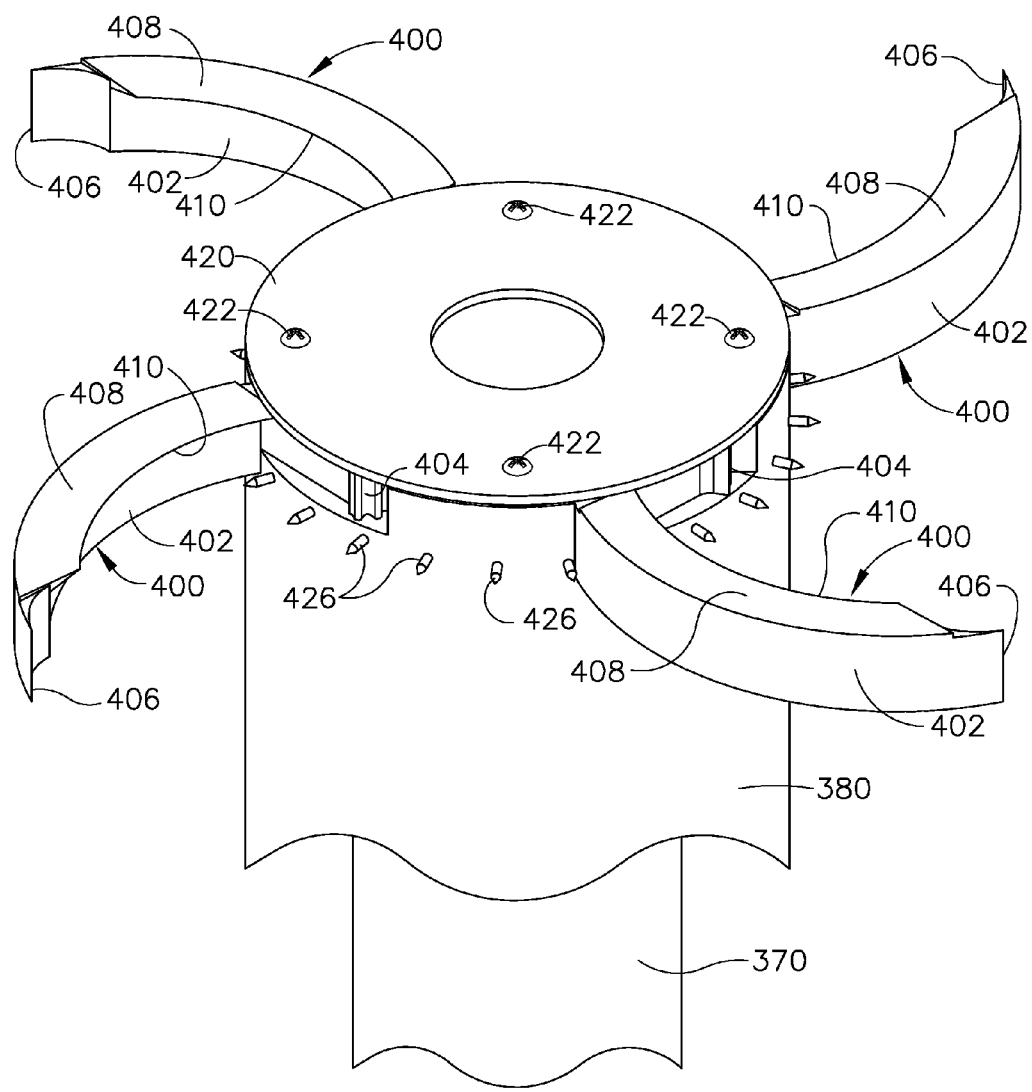
FIG. 22 is a perspective view of the acquisition shaft of FIG. 21.

As can be seen in FIGS. 19 and 22, each tissue arm 400 has a body portion 402 that may be fabricated from, for example, stainless steel (300 or 400 series), or titanium-steel composite or ceramic, etc. and have a driven gear 404 attached thereto or formed thereon. The driven gear 404 of each tissue arm 400 is movably supported within a corresponding arm cavity 388 formed in the distal end 384 of the tissue acquisition shaft 380. Each driven gear 404 is in meshing engagement with the drive gear 374 on the deployment shaft 370. Thus, rotation of the deployment shaft 370 will result in the pivotal deployment of the tissue arms 400 from the retracted position depicted in FIG. 20 to the deployed position depicted in FIG. 22. As can be seen in FIGS. 20 and 22, in various embodiments, each tissue arm 400 has an arcuate shape such that when the tissue arms 400 are in a retracted position as shown in FIG. 20, they cooperate to create a round disc-like assembly 401 at the distal end of the tissue acquisition shaft 380.

In various embodiments, the body portion 402 of each tissue arm 400 further has a tissue piercing tip 406 formed thereon or otherwise attached thereto. In addition, an arm knife 408 that has a cutting edge 410 formed thereon is attached to or is otherwise formed on the body portion 402 of each tissue arm 400. In various embodiments, the arm knife 408 may be fabricated from, for example, stainless steel (300 or 400 series), or titanium-steel composite or ceramic, etc. and be attached to the body portion 402 of the corresponding tissue arm 400 by, depending upon the material, welding or other suitable attachment method. In the preferred embodiments, if the arm knife 408 is fabricated from any of the metal materials identified above, it may be desirable for such material to be hardened. For example, a Rockwell hardness value of 38-52 may be desirable. In alternative embodiments, the arm may be fabricated with a thin feature that could be ground to a sharp edge. As will be appreciated as the present Detailed Description proceeds, the blade works more like a scissors rather than a knife as it cuts when closed such that it shears the tissue when 408 closes against 421. As can also be seen in FIG. 19, a shear plate 420 is attached to the distal end 382 of the arm shaft 380 by threaded fasteners 422 that extend into threaded fastener bores 424 in the arm shaft 380. Also in various embodiments, a plurality of tissue acquisition pins 426 are equally spaced around the circumference of the tissue acquisition shaft 380 and protrude radially therefrom. The outer edge 421 of the shear plate 420 cooperates with the cutting edges 410 on the tissue arms 400 to shear off tissue that is drawn between those edges 410, 421 as the tissue arms 400 are moved to their retracted position.

In certain implementations, a distal end post 442 protrudes from a portion of the firing shaft 350 that coaxially extends within the deployment shaft 370 for selective axial travel therein. The distal end post 442 supports a distal anvil connector 450 therein that is coupled to an adjustment knob 460 that is rotatably supported on the handle assembly 312 in the various manners discussed above.

Figure 23:
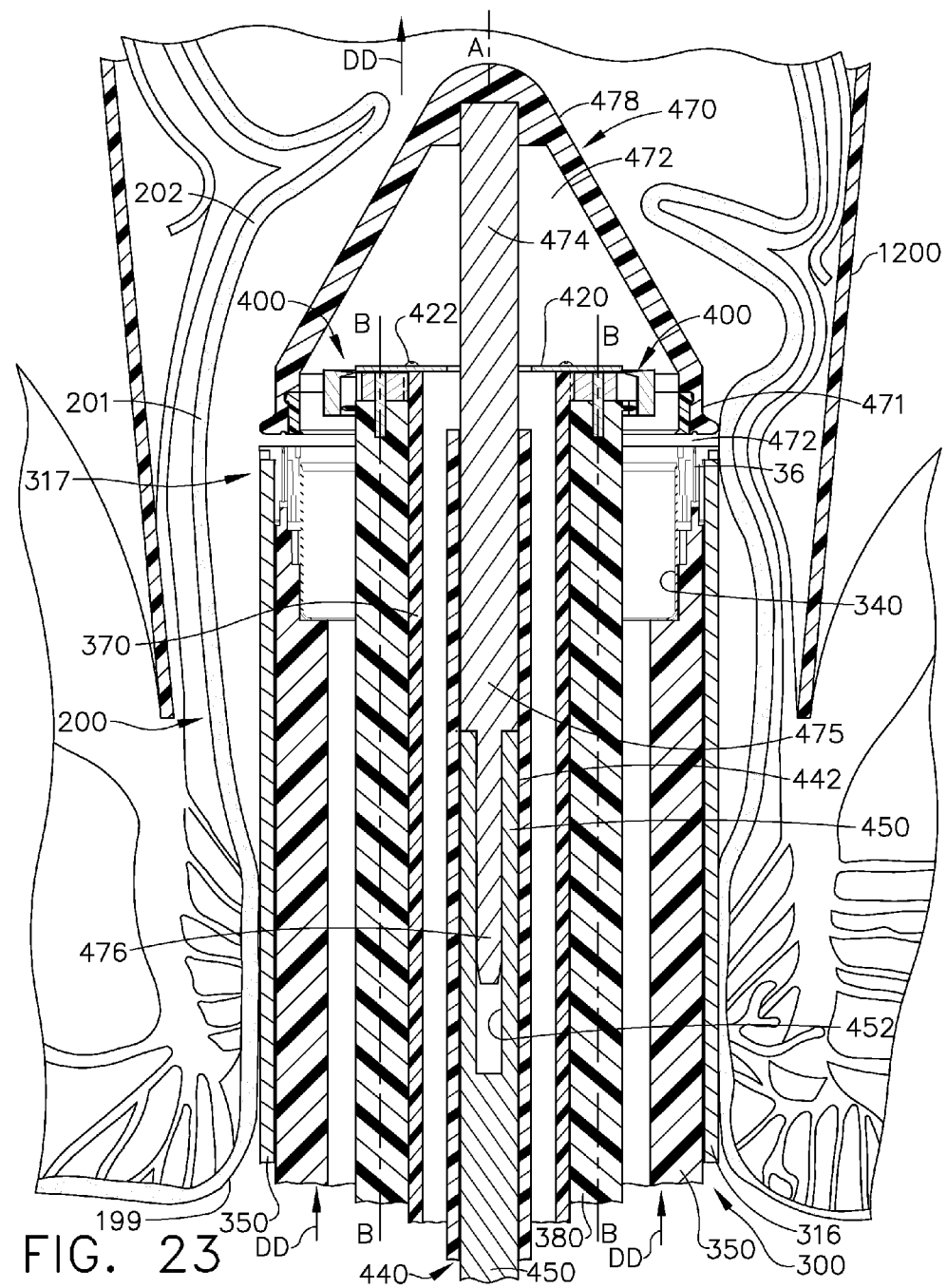
FIG. 23 is a cross-sectional view of the elongated shaft of various non-limiting embodiments of the present invention, with an anvil attached thereto and inserted into a portion of a patient's colon.
Figure 24:
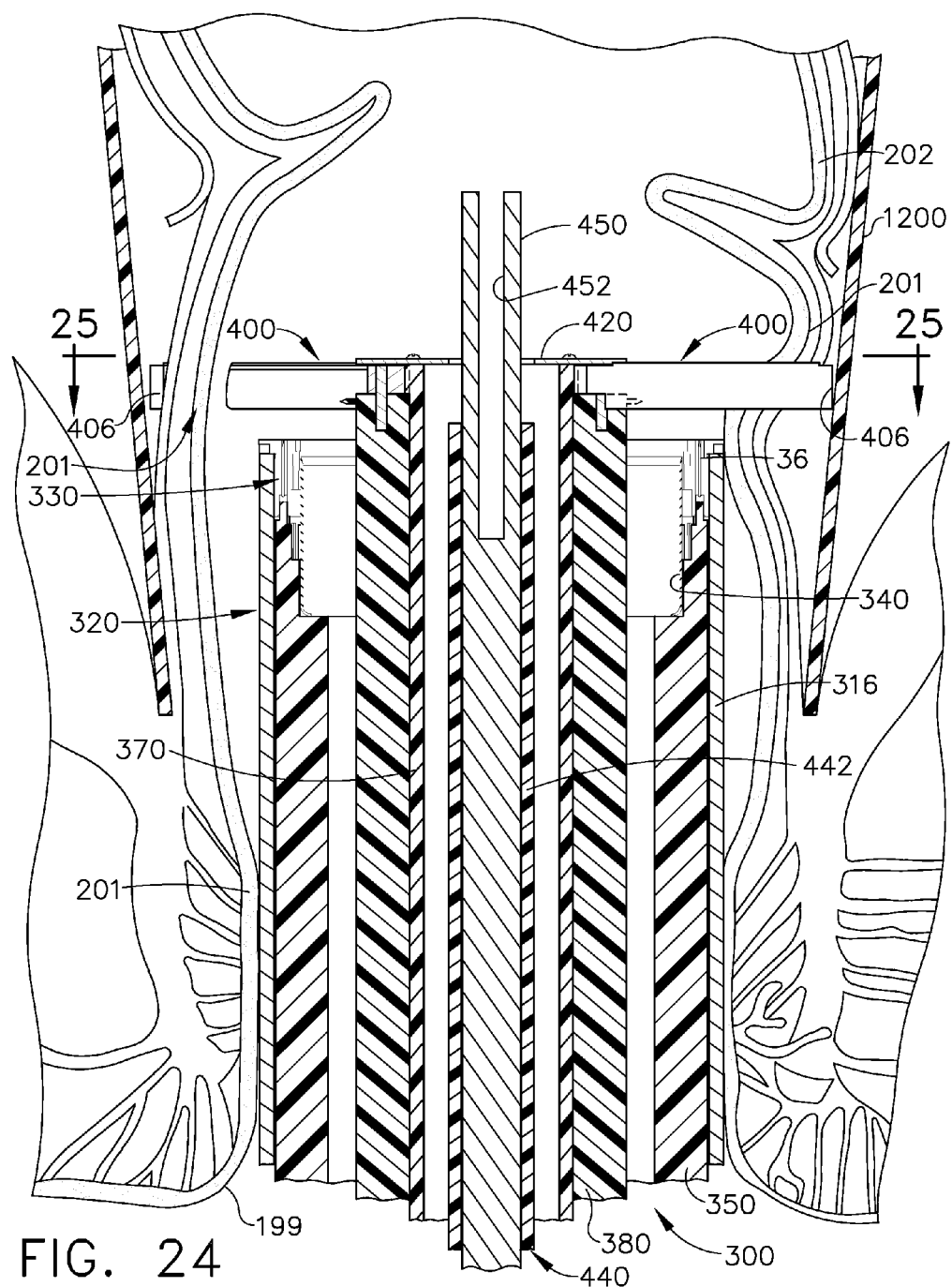
FIG. 24 is another cross-sectional view of the elongated shaft of FIG. 23, with the anvil removed and the acquisition arms deployed through a proximal portion of the colon that is adjacent to a target or diseased portion of the colon.
Figure 25:
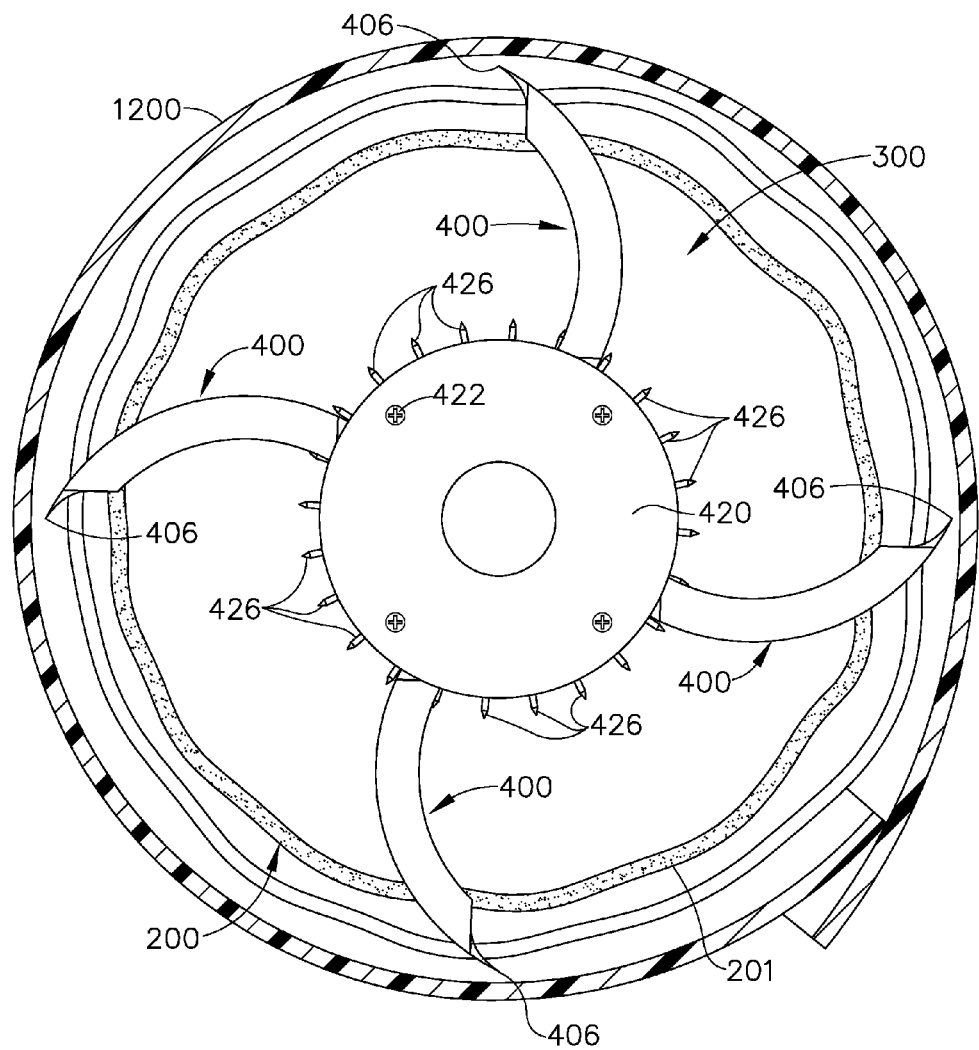
FIG. 25 is a top cross-sectional view of the elongated shaft of FIG. 24 taken along line 25-25 in FIG. 24 with the tissue acquisition arms extended through the proximal portion of the colon.

The circular stapler 300 further includes an anvil 470 as shown in FIG. 18. In various non-limiting embodiments, the anvil 470 includes an anvil base 471 that has a series of staple forming pockets 472 therein. The anvil base 471 may further define a shear edge 473 for facilitating the shearing of tissue by the annular knife 340. The anvil 470 further includes an anvil shaft 474 that is removably attachable to the distal anvil connector 450. In particular, a coupling stem 476 protrudes from the proximal end 475 of the anvil shaft 474 and is sized to be slidably received in a passage 452 in the anvil shaft assembly 450. See FIG. 23. The anvil assembly 470 further has an anvil cap 478 thereon that serves to define a tissue cavity 479 therein as illustrated in FIGS. 18 and 23. As can also be seen in FIG. 18, the disc-like assembly 401 is sized to extend into an opening 475 in the anvil base 471.

One exemplary method of using the circular stapler 300 will be described with reference to FIGS. 23-31. The various embodiments of the circular stapler 300 are particularly well-suited for performing a circular anastomosis of a tubular organ such as, for example, a colon 200. Turning first to FIG. 23, the stapler head 320 is inserted through the patient's anus 199 into a proximal portion 201 of the colon 200. When a diseased or otherwise targeted portion 202 of colon 200 is to be removed, the stapler head 320 is positioned in an area wherein the diseased portion 202 is to be severed from the proximal portion 201.

Figure 26:
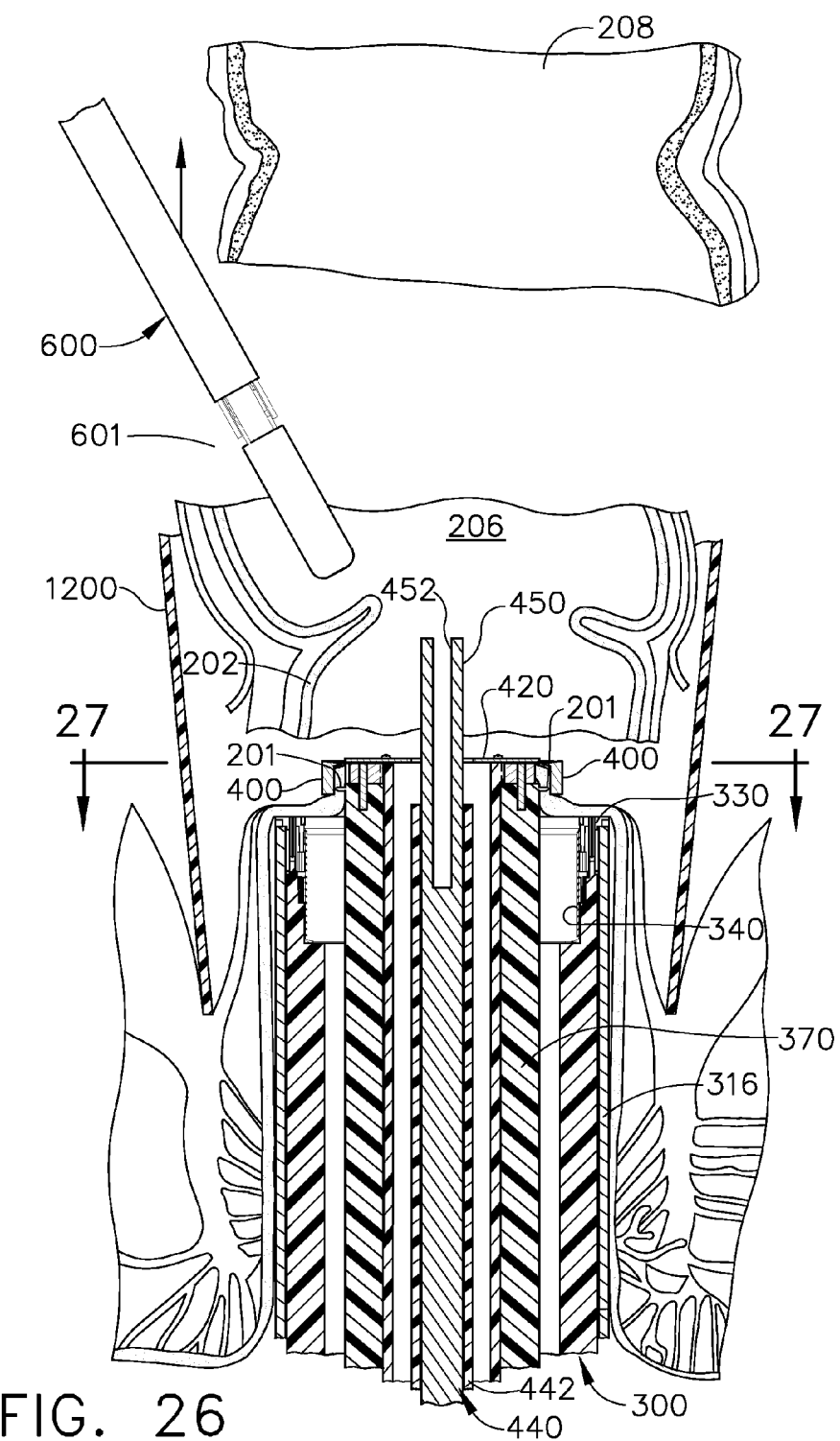
FIG. 26 is a partial cross-sectional view of the elongated shaft of FIGS. 24 and 25 with the targeted or diseased portion of the colon being removed with a grasping instrument.
Figure 27:
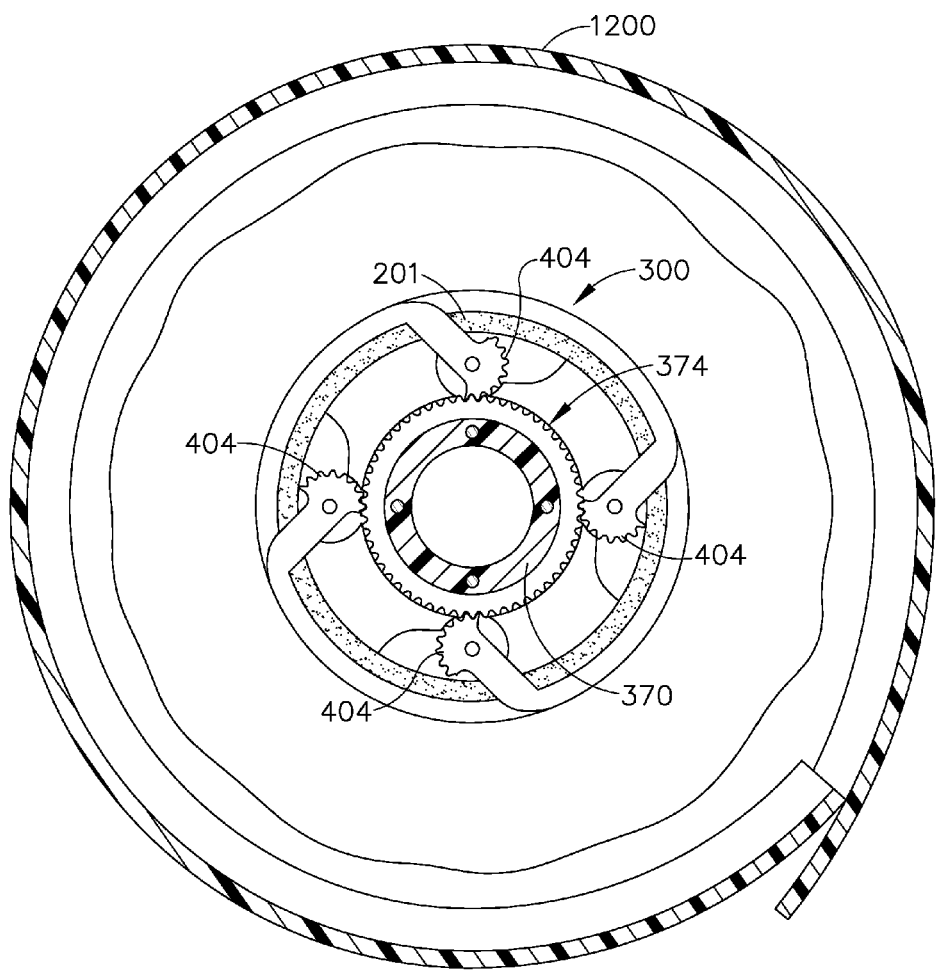
FIG. 27 is a top cross-sectional view of the elongated shaft of FIG. 26 taken along line 27-27 in FIG. 26.

Once the stapler head 320 has been properly positioned within the colon, the tissue arms 400 may be radially deployed by rotating the tissue acquisition knob 310 in a first direction (represented by arrow 311 in FIG. 17) which also rotates the deployment shaft 370. Rotation of the deployment shaft 370 in the first direction also rotates the drive gear 374 which is in meshing engagement with the driven gear portions 404 of each tissue arm 400. Thus, rotation of the drive gear 374 in the first direction causes the tissue arms 400 to be radially deployed. As the tissue arms 400 are radially deployed, the tissue-piercing tips 406 thereof pierce through the proximal portion 201 of colon 200. See FIGS. 24 and 25. Once the tissue arms 400 have been deployed such that the tissue-piercing tips 406 thereof have pierced through the proximal portion 201 of colon 200, the surgeon may then rotate the tissue acquisition knob 310 in a second direction (represented by arrow 313 in FIG. 17) to move the tissue arms 400 to the retracted position. As the tissue arms 400 are retracted, they gather the pierced proximal portion 201 of colon 200 and draw it inward toward the tissue acquisition shaft 380. As the gathered colon 201 is drawn between the shear plate 420 and the tissue arms, the portion 201 of the colon 200 that is captured between the outer edge 421 of the shear plate 420 and the cutting edges 410 on the tissue arms 400 is severed from the diseased portion 202 of the colon 200. Retraction of the tissue arms 400 causes the portion 201 of the colon 200 to be impaled onto the tissue retention pins 426 and retained thereon as shown in FIG. 26. Thereafter, the diseased portion 202 of the colon 200 may be transected from the distal colon portion 208 using a conventional laparoscopic tissue severing instrument (not shown) inserted through a trocar sleeve inserted into the abdominal cavity 601. After the diseased portion 202 has been cut away from the distal colon portion 208, the diseased portion 202 may be removed through the trocar sleeve (not shown) with a conventional grasping instrument 600. See FIG. 26.

Figure 28:
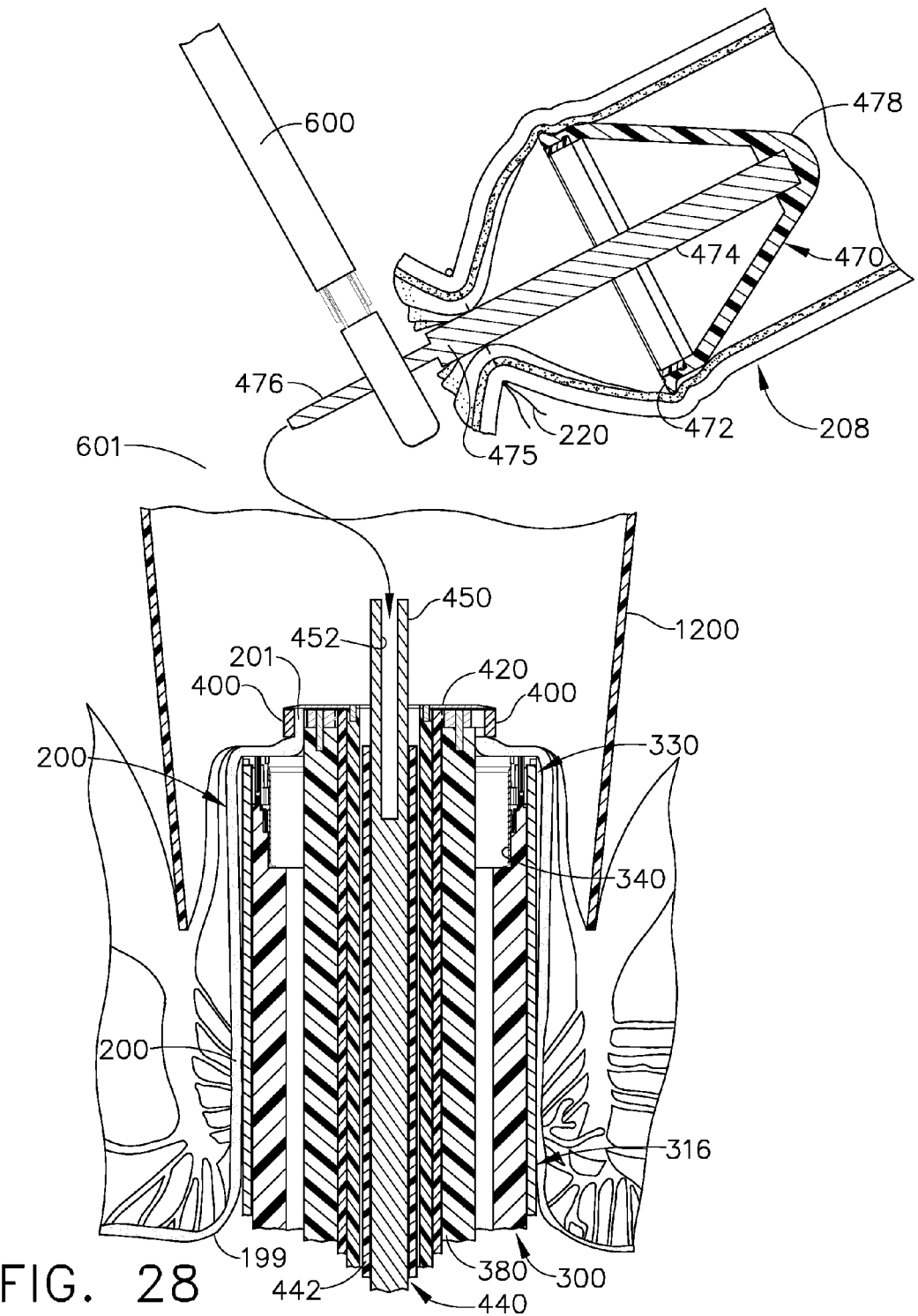
FIG. 28 is a partial cross-sectional view of the elongated shaft after the anvil has been inserted into a distal portion of the colon and secured thereto by a purse-string suture arrangement.

The surgeon then orients the anvil 170 within the distal portion 208 of the colon 200 such that the anvil shaft coupling stem 476 of the anvil shaft 474 protrudes out of the distal portion 208 of the colon 200 as shown in FIG. 28. The surgeon then ties the end of the distal colon portion 208 around the anvil shaft 474 using what is known in the art as a "purse string suture" 220. Once the distal colon portion 208 has been sutured around the anvil shaft 474, the coupling stem 476 of the anvil shaft 474 is inserted into the passage 452 in the anvil shaft assembly 450. The coupling stem 476 is sized relative to the passage 152 to establish a frictional fit therebetween to retain the coupling stem 176 therein, yet permit the coupling stem 176 to be removed therefrom at a later time. See FIG. 28.

Figure 29:
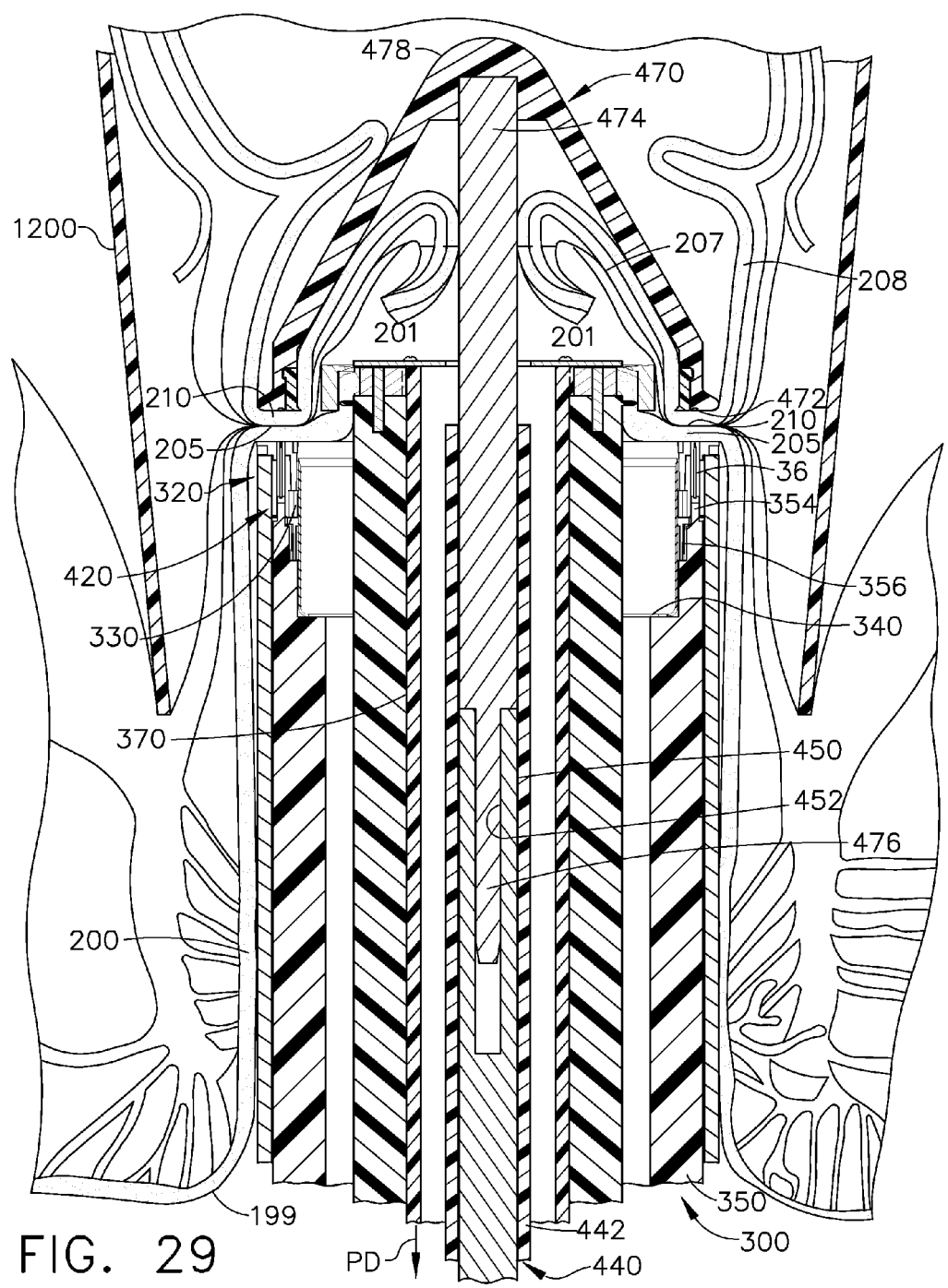
FIG. 29 is a cross-sectional view of the elongated shaft of FIG. 28 after the anvil has been coupled to the anvil assembly thereof and drawn into confronting relationship with the stapling cartridge therein.
Figure 30:
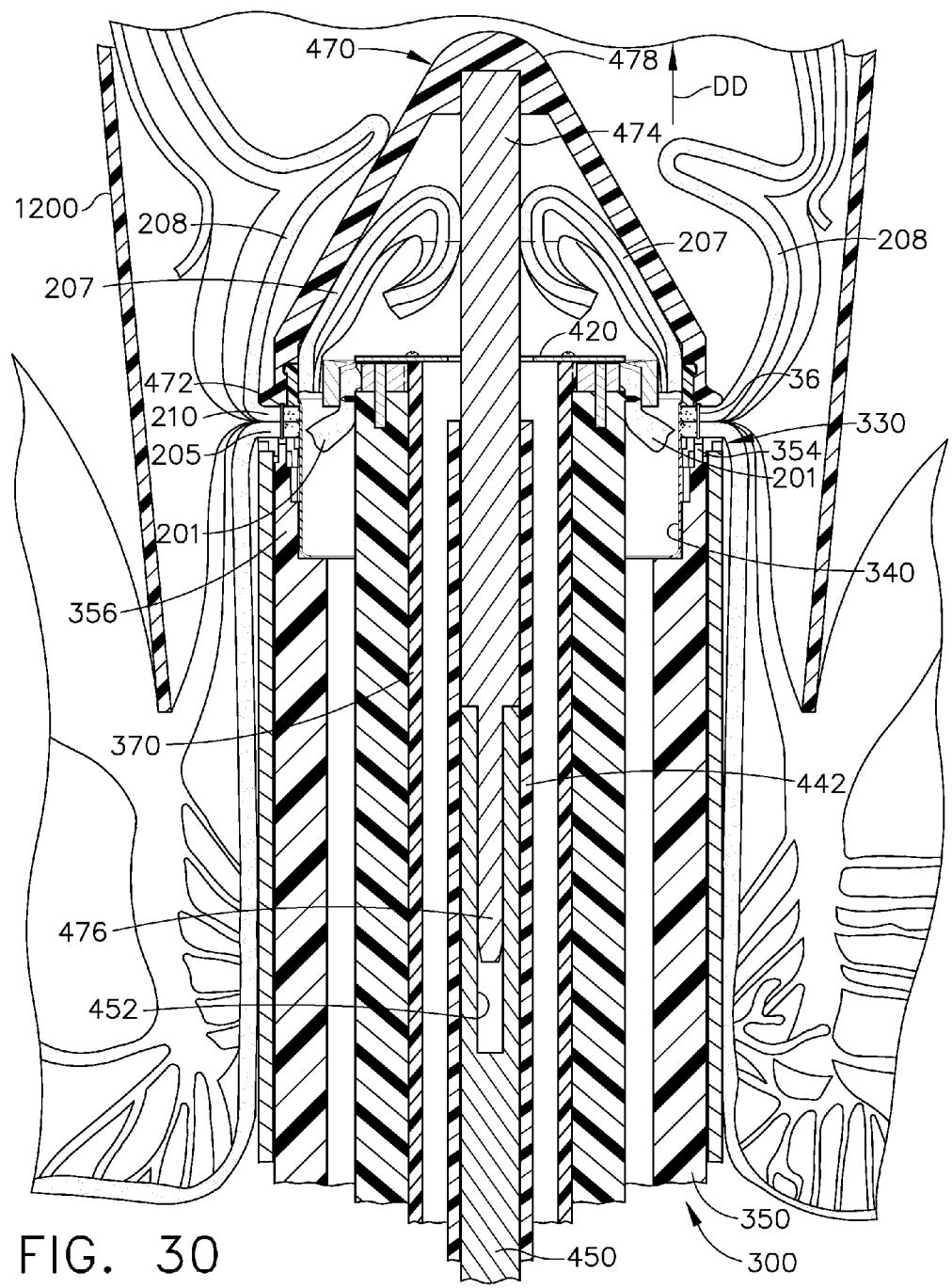
FIG. 30 is a cross-sectional view of the elongated shaft of FIG. 29 after the staple cartridge had been fired and the annular cutting member advanced through the stapled tissue portions.
Figure 31:
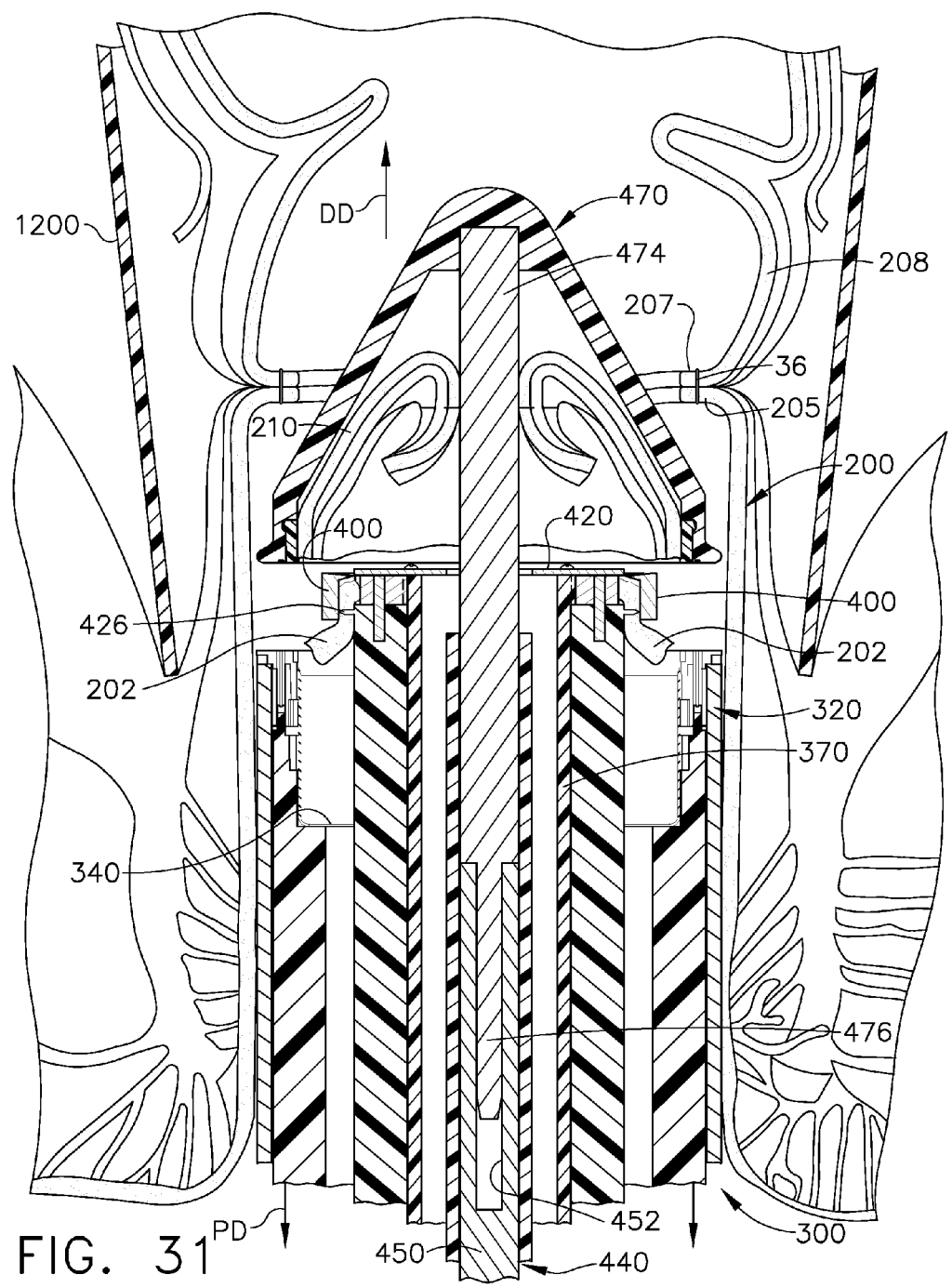
FIG. 31 is a cross-sectional view of the elongated shaft of FIG. 30 being withdrawn from the colon after completion of the stapling procedure.

The surgeon then draws the anvil 470 toward the stapler head 420 (in the proximal direction "PD") by rotating the anvil control knob 460 in the appropriate direction until portions 205, 210 of the colon 200 are clamped between the anvil 470 and the staple cartridge 330 as shown in FIG. 29. Thereafter, the surgeon actuates the firing trigger 360 to axially advance the firing shaft 350 in the distal direction "DD". As firing shaft 350 is advanced distally, the staple driver portions 354, 356 serve to drive the staples 36 through the portions 205, 210 of colon 200 into the anvil forming pockets 472 in the anvil 470. The firing shaft 350 also advances the annular knife 340 through the colon portions 205, 210 to sever portions 201, 207, respectively therefrom. The surgeon may then move the anvil 470 in the distal direction "DD" to release the stapled colon portions 205, 210 from between the anvil 470 and the stapler head 320. The instrument 300 may then be removed from the colon 200. See FIG. 31. The severed portions 201, 207 of the colon 200 remain in the stapler head 320 and the anvil 470, respectively as the surgeon withdraws the instrument 300 out through the patient's anus. Thus, the severed portions 201, 207 of the colon 200 are removed from the repaired colon when the instrument 300 is withdrawn therefrom.

Figure 32:
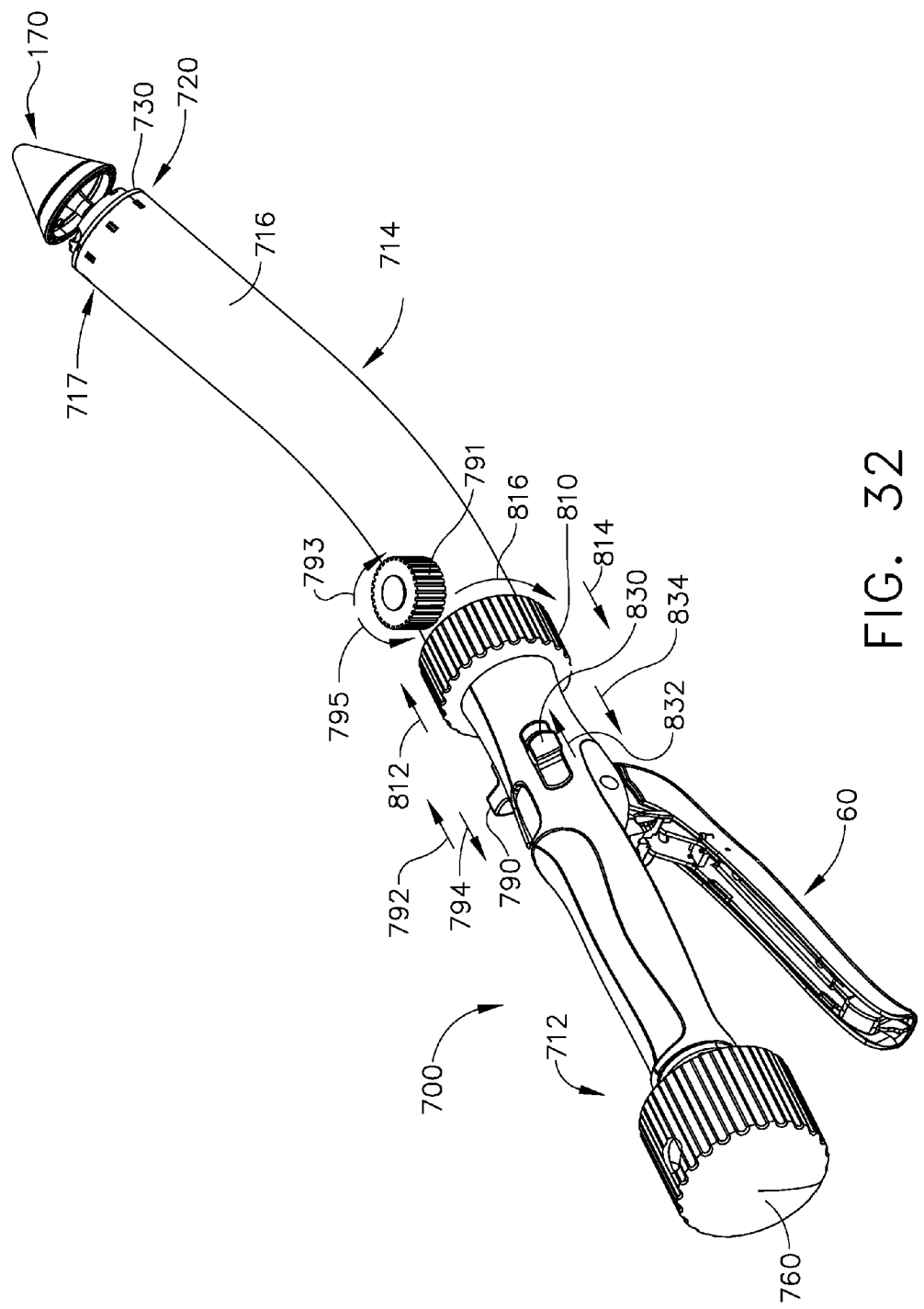
FIG. 32 is a perspective view of another a surgical circular stapling instrument of various non-limiting embodiments of the present invention.

Circular stapling instruments are generally introduced through the anus and not from the abdomen side of the pelvis. Such method of entry complicates the ability of the surgeon to visualize the tumor, the tumor's necessary margins and those margin edges with respect to the distal transection location to ensure that the stapler head has been properly positioned in the colon before commencing the transection. FIGS. 32-37 illustrate a circular stapler 700 according to various non-limiting embodiments of the invention that may provide feedback to the surgeon during the insertion process. The circular stapler 700 generally includes a handle assembly 712 that has an elongated shaft assembly 714 protruding therefrom. The elongated shaft assembly 714 may define a central axis A-A. As can be seen in FIG. 32, the elongate shaft assembly 714 includes a rigid outer sheath 716 that has a distal end portion that supports a stapler head 720 thereon. In various non-limiting embodiments, the stapler head 720 is configured to operably support a circular staple cartridge 730 therein. Such circular staple cartridges 730 are known in the art and generally may support one, two or more than two circumferentially spaced and staggered rows of staples therein. In the non-limiting embodiment depicted in FIG. 33, the staple cartridge 730 supports two rows 732, 734 of staples 36 therein. A conventional annular knife 740 is coaxially and movably supported within the stapler head 720.

The circular stapler 700 further includes a firing shaft 750 that is operably supported within the rigid outer sheath 716 for selective axial travel therein. See FIG. 33. A distal end portion 752 of the firing shaft 750 has an outer staple driver portion 754 thereon for engagement with each of the staples 36 in the outer row 732 of staples 36 in the staple cartridge 730. In addition, the distal end portion 752 of the firing shaft assembly 750 has an inner staple driver portion 756 that is configured for engagement with each of the staples 36 in the inner row 734 of staples 36 within the staple cartridge 730. As can also be seen in FIG. 33, for example, the distal end portion 752 of the firing shaft 750 further has a flanged portion 758 that is configured to engage the annular knife 740. Thus, as will be discussed in further detail below, axial advancement of the firing shaft 750 in a distal direction "DD", will cause the staples 36 to be driven out of the staple cartridge 730 as well as the annular knife 740 to advanced distally.

In various non-limiting embodiments, the firing shaft 750 interfaces with a firing trigger 60 that is operably coupled to the handle assembly 712. As can be seen in FIG. 32, the firing trigger 60 is pivotally coupled to the handle assembly 712 such that when the firing trigger 60 is pivoted toward the handle assembly 712, the firing shaft 750 is moved in the distal direction DD as was discussed above.

Figure 33:
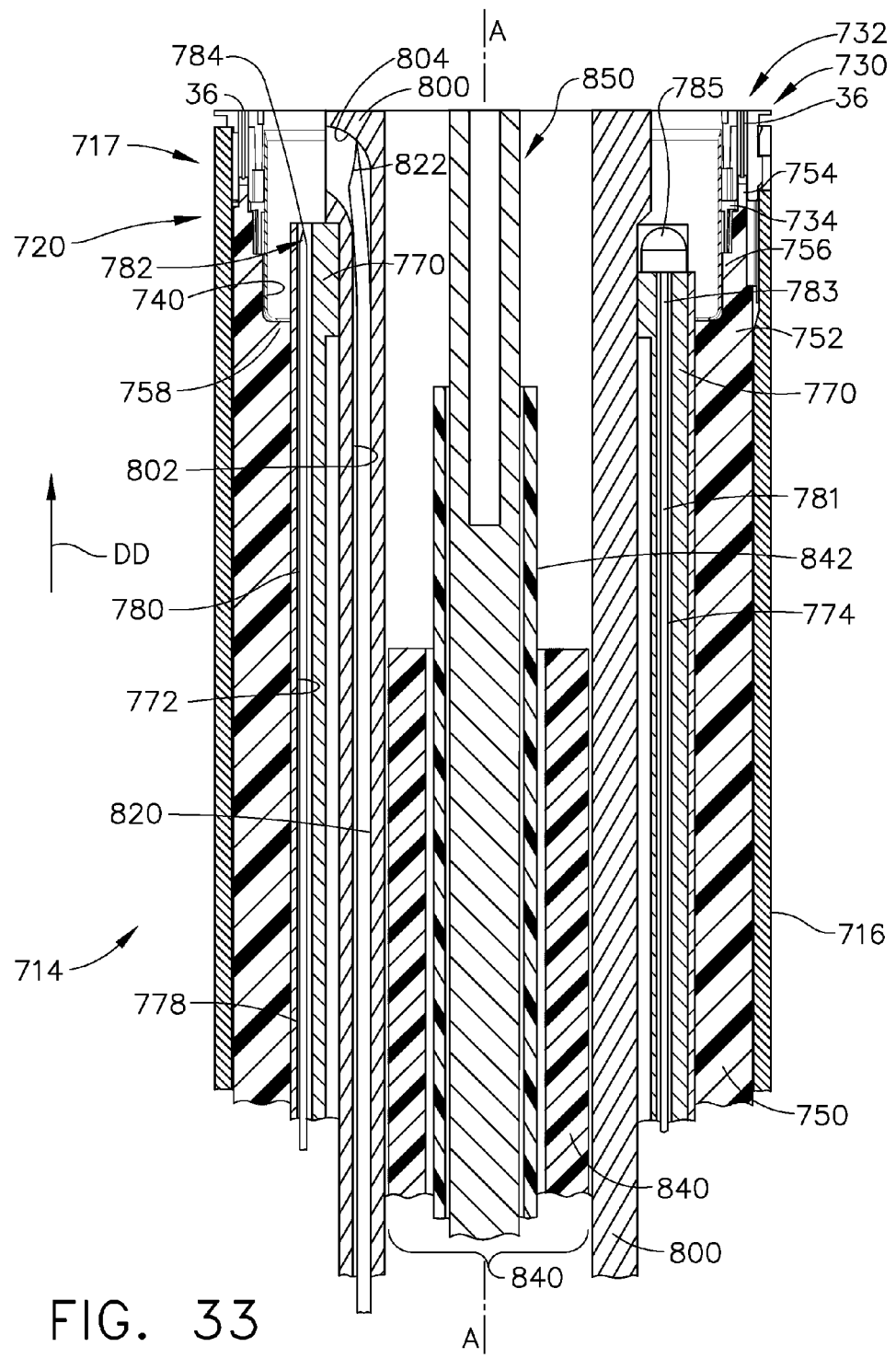
FIG. 33 is a cross-sectional view of a distal end portion of the elongated shaft of the circular stapling instrument of FIG. 32.
Figure 34:
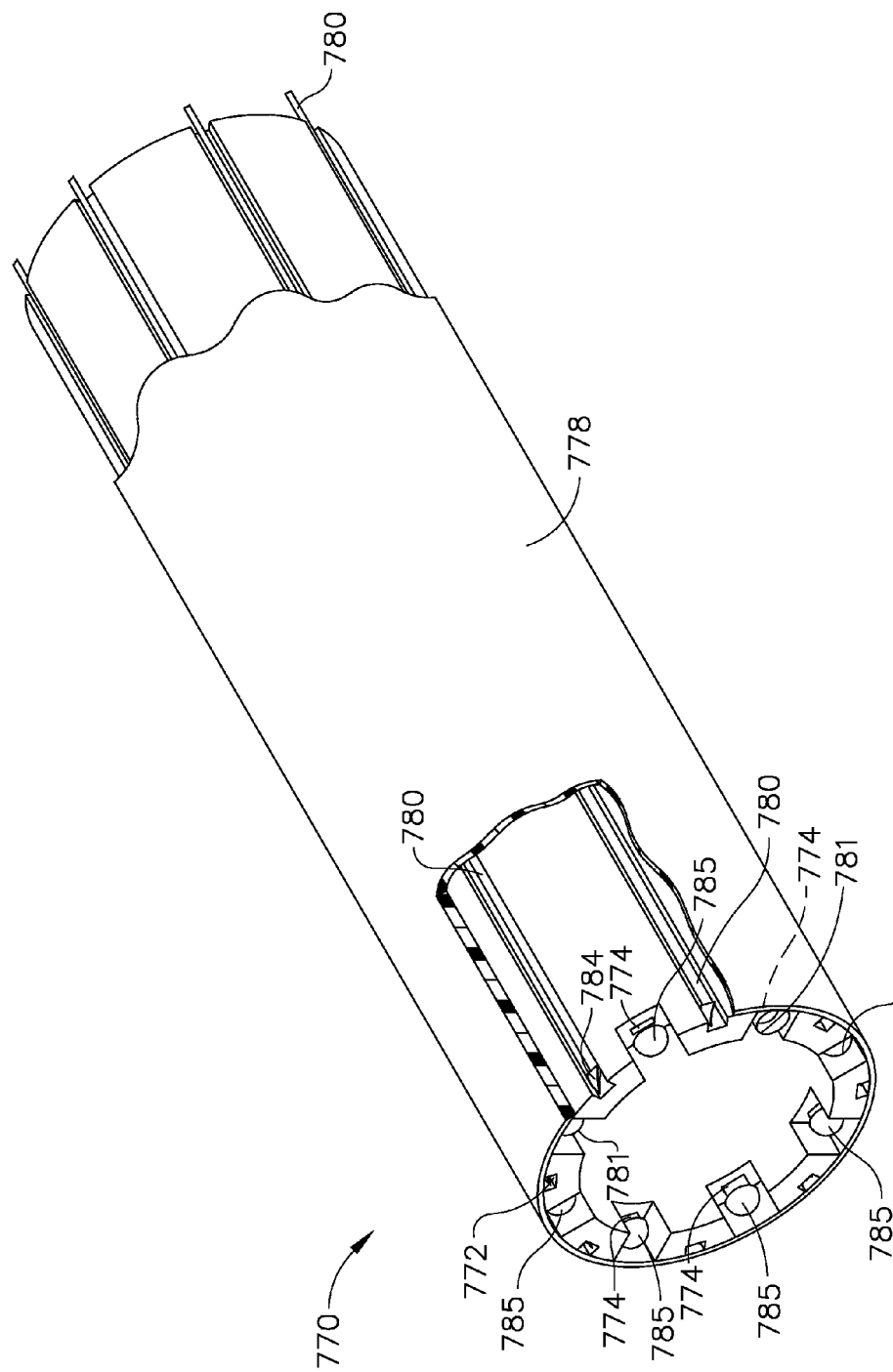
FIG. 34 is a partial perspective view of a hook and detection housing portion of the elongated shaft of FIG. 33 with the detection members thereof in a retracted position.

As shown in FIG. 33, various non-limiting embodiments include a hook and detection housing 770 that is coaxially supported within the firing shaft 750 and axially movable therein. The hook and detection housing 770 has a plurality of hook lumens 772 therein that each movably supports an acquisition hook member 780 therein. As can be seen in FIG. 34, for example, the plurality of three-sided hook lumens 772 may be equally spaced around the circumference of the hook and detection housing 770. For example, in the non-limiting embodiment depicted in FIG. 34, a total of eight (8) hook lumens 772 are equally spaced around the circumference of the hook and detection housing 770. Each hook member 780 may be fabricated from, for example, Nitinol, 300 or 400 series stainless steel (fully or three-fourths hardened), etc. and have a distal end portion 782 that, when advanced out of its respective hook lumen 772, naturally flexes or bends radially outward in the manners described above. As with other embodiments, each acquisition hook member 780 may have a tissue barb 784 formed on the distal end portion 782 thereof. As can be seen in FIGS. 33 and 34, in various non-limiting embodiments, the hook and detection housing 770 includes a hook sleeve 778 that facilitates installation of the acquisition hook members 780 into their respective lumens 772.

In various non-limiting embodiments, a proximal end portion of the hook and detection housing 770 may operably interface with a hook switch 790 that is operably supported on the handle 712. See FIG. 32. As the surgeon moves the hook switch 790 in a distal direction (arrow 792 in FIG. 32), the hook and detection housing 770 moves distally. In addition, each acquisition hook member 780 is advanced distally out of its respective hook lumen 772 as was described above. The surgeon may retract the hook members 780 into their starting positions by moving the hook switch 790 in a proximal direction (arrow 794 in FIG. 32).

Figure 35:
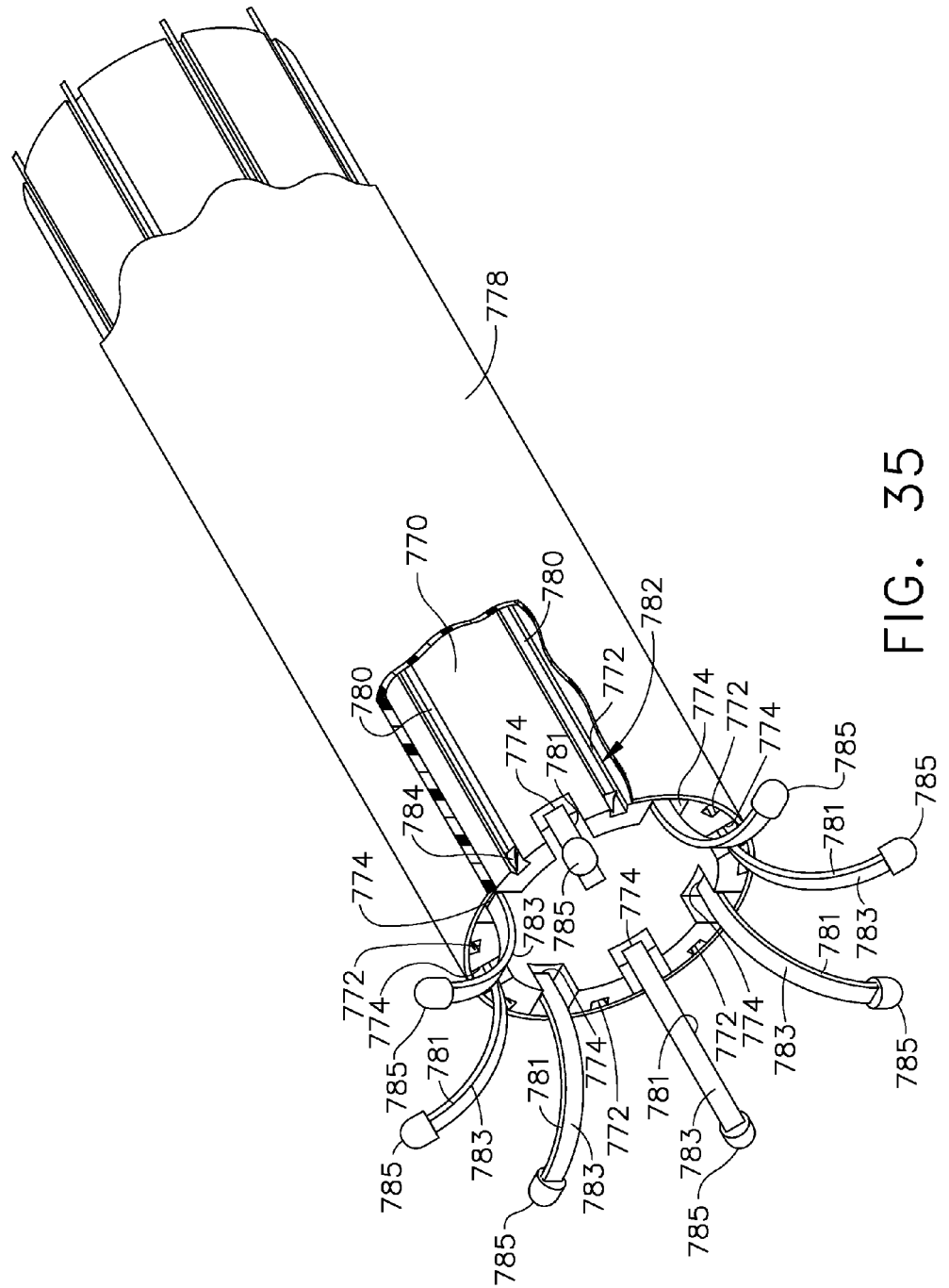
FIG. 35 is another partial perspective view of the hook and detection housing of FIG. 34 with the detection members thereof in a deployed orientation.

Also supported within the hook and detection housing 770 are a plurality of flexible detection members 781. In particular, a plurality detection lumens 774 are also provided in the hook and detection housing 770. For example, in the non-limiting embodiment depicted in FIG. 34, a total of eight (8) detection lumens 774 are equally spaced around the circumference of the hook and detection housing 770. In one non-limiting embodiment, each detection member 781 may be fabricated from, for example, polyethylene, Nylon, Nitinol, titanium etc. and have a distal end portion 783 that, when deployed out of its respective detection lumen 774, naturally flexes or bends radially outward as illustrated in FIG. 35. In addition, a substantially blunt or rounded bumper 785 may be provided on the distal end of each detection member 781. In one embodiment, the bumper may be fabricated from, for example, Sanoprene, Isoprene, natural rubber, polypropylene, polyethylene, Nylon, etc. In other embodiments, the bumper 785 may comprise a light or light emitting diode (LED). In those embodiments, a conductor may extend from a battery in the handle assembly 712 or other energy source through a lumen in the detection member 781 to the light 785.

Figure 36:
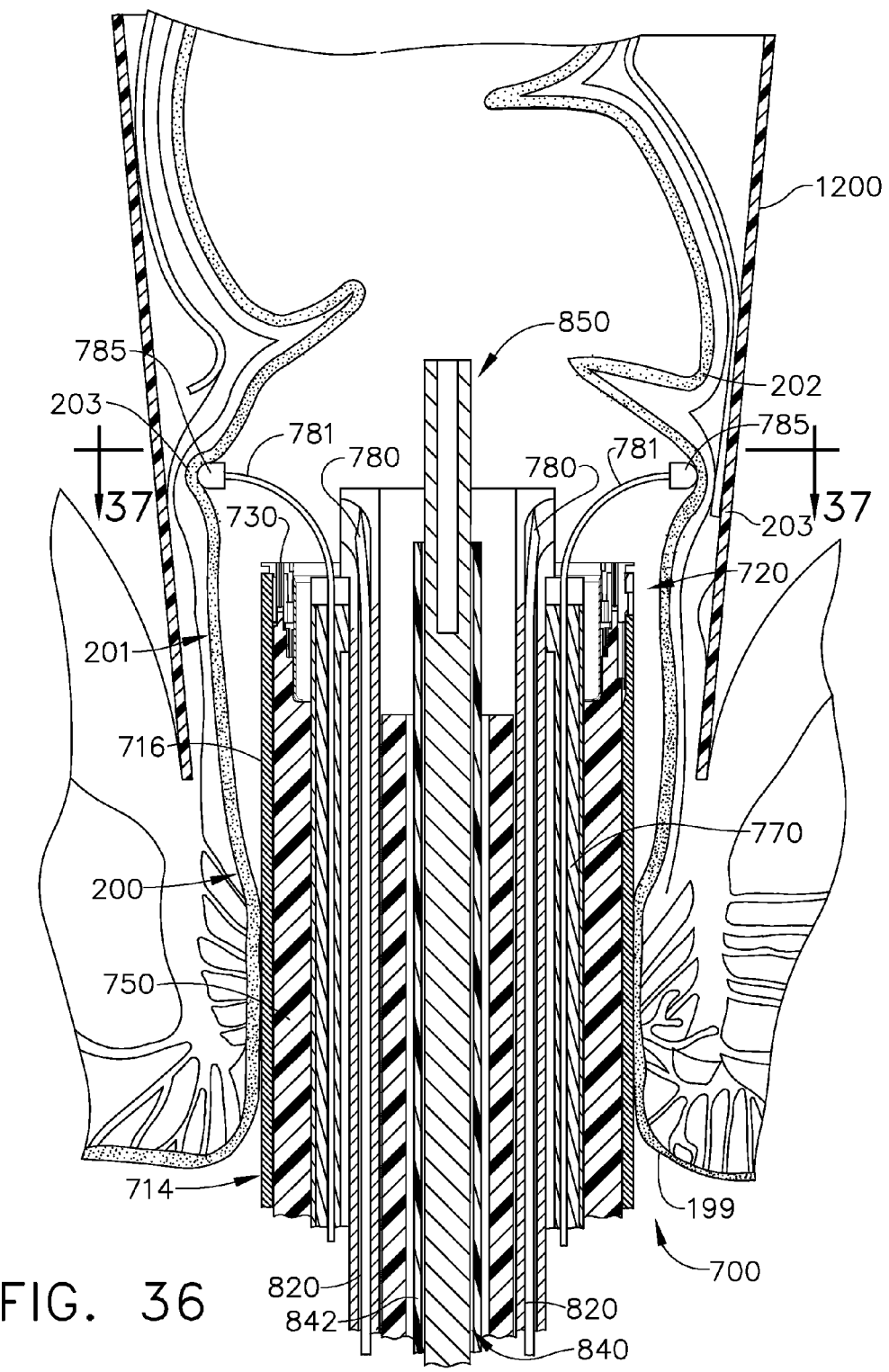
FIG. 36 is a partial cross-sectional view of the distal end of the elongated shaft with the detection members thereof in a deployed orientation within a colon.

In various non-limiting embodiments, a proximal end portion of each detection member 770 may interface with a detection knob 791 that is operably supported on the handle assembly 712. See FIG. 32. As the surgeon rotates the detection knob 791 in a first direction (arrow 793 in FIG. 32), the detection members 781 deploy distally out of their respective lumens in a radial direction away from central axis A-A to deployed positions (FIG. 36). In various embodiments, for example, all of the detection members 781 may be attached to a round sleeve (not shown) that is slidably supported within the outer sheath 716. The round sleeve may further have a gear rack attached thereto that is received in meshing engagement with a gear (not shown) on the underside of the detection knob 791. Rotation of the detection knob 791 in one direction moves the sleeve distally and therefore extends all of the detection members 781. When the surgeon rotates the detection knob 791 in a second direction (arrow 795 in FIG. 32), the detection members 781 are drawn back into their respective detection lumens 774 to the retracted position. See FIG. 34. Other switches and drive arrangements could also be employed to selectively extend and retract the detection members without departing from the spirit and scope of the present invention.

As can be further seen in FIG. 33, in various non-limiting embodiments, a cutter housing 800 is coaxially supported within the hook and detection housing 770. The cutter housing 800 is supported for selective axial travel relative to the hook and detection housing 770 and for selective axial travel along central axis A-A. The cutter housing 800 interfaces with a knife knob 810 that is movably supported on the handle assembly 712. See FIG. 32. In various non-limited embodiments, the knife knob 810 is supported on the handle assembly 712 such that it can move axially (represented by arrows 812, 814 in FIG. 32) and also be rotated relative to the handle assembly 712 (represented by arrow 816 in FIG. 32). The cutter housing 800 may be attached to the knife knob 810 in the various manners described above such that movement of the knife knob 810 in an axial direction moves the cutter housing 800 axially within the hook and detection housing 770 and rotation of the knife knob 810 also rotates the cutter housing 800 about the central axis A-A.

In various non-limiting embodiments, the cutter housing 800 includes a plurality of knife lumens 802 that extend axially through the wall of the cutter housing 800. As was discussed above with respect to other embodiments, the plurality of knife lumens 802 may be spaced equally around the circumference of the cutter housing 800. For example, in a non-limiting embodiment, a total of eight (8) knife lumens 802 may be equally spaced around the circumference of the cutter housing 800. As can be seen in FIG. 33, each knife lumen 802 has a curved distal end portion 804 that opens radially outward.

In various non-limiting embodiments, a flexible knife member 820 is slidably received within each knife lumen 802. Each flexible knife member 820 has a sharpened distal end 822 and a proximal end (not shown) that interfaces with a knife switch 830 that is operably mounted to the handle 712 in the various manners described above. See FIG. 32. The distal end 822 may be substantially pointed to enable it to pierce through tissue and it may have at least one cutting edge formed thereon. When the knife switch 830 is moved in the distal direction (arrow 832), the knife members 820 are moved distally within the knife lumens 802 such that the sharpened distal end 822 naturally flexes or bends radially out of the curved distal end portion 804 of the lumen 802 as was described above. Likewise, movement of the knife switch 830 in the proximal direction (represented by arrow 834 in FIG. 32), causes the knife members 820 to be retracted back into their respective knife lumen 802. In various non-limiting embodiments, the knife members 820 may be fabricated from, for example, Nitinol, 300 or 400 series stainless steel (fully of three-fourths hardened).

As can also be seen in FIG. 33, various non-limiting embodiments may further include an anvil shaft assembly 840 that is coaxially supported within the cutter housing 800 for selective axial travel therein. The anvil shaft assembly 840 may comprise a distal end post 842 that protrudes from a portion of the firing shaft firing shaft 750. The distal end post 842 supports a distal anvil connector 850 therein that that protrudes distally from the distal end post 842. The anvil shaft assembly 840 has a proximal end portion that interfaces with an adjustment knob 760 that is rotatably supported on the handle assembly 712 as was discussed above with respect to other non-limiting embodiments. The circular stapler 700 further includes an anvil 170 as shown in FIG. 32.

Figure 37:
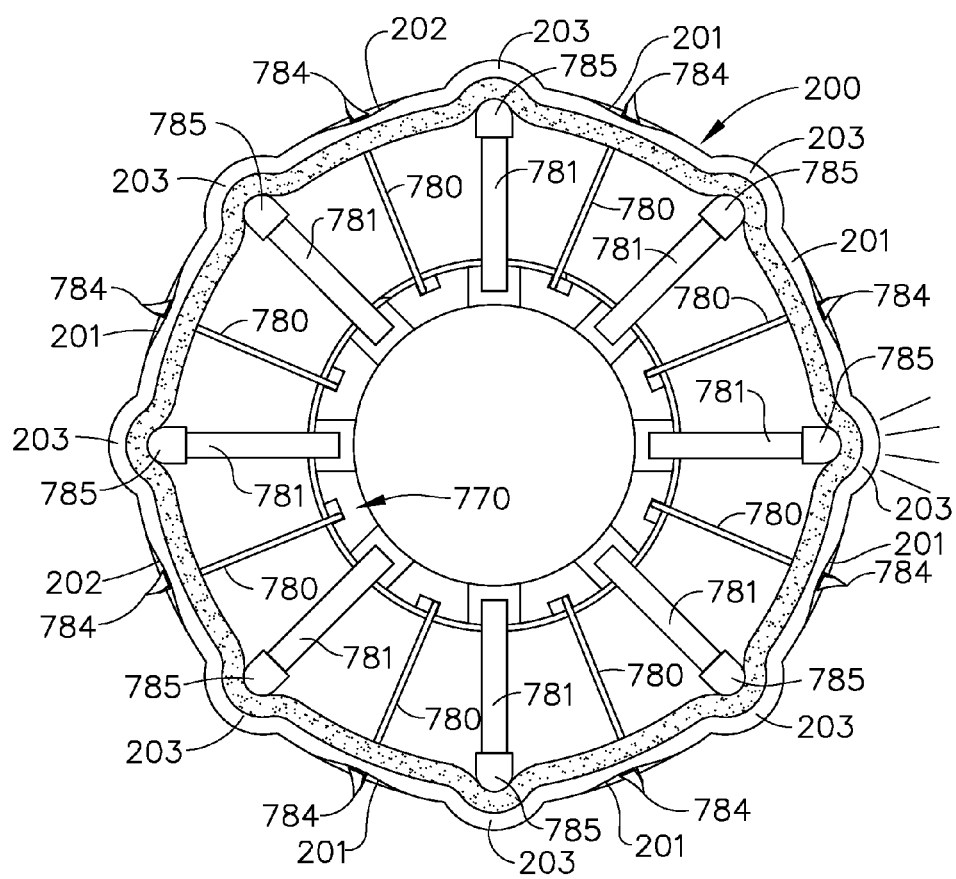
FIG. 37 is a top cross-sectional view of the elongated shaft and colon of FIG. 36 taken along line 37-37 in FIG. 36.

One exemplary method of using the circular stapler 700 will now be described. To commence the procedure, the surgeon inserts the elongated shaft 714 through the patient's anus 199 into a proximal portion 201 of the colon 200. Thereafter, the surgeon may extend the detection members 781 as illustrated in FIGS. 36 and 37 to "fine tune" the positioning of the stapler head 720. This may be accomplished by rotating the detection knob 791 in the appropriate direction. As the bumpers 785 are forced radially into the wall of colon portion 201, they create identifiable bumps or deflections 203 or irregular areas that protrude outward and provide means for the surgeon to visually observe where the stapler head 720 is located. Such identifiable features are distinct from the actual anatomy of the colon wall. The substantially blunted or rounded bumpers do not penetrate or damage the colon wall. Such bumps 203 allow the surgeon to position the stapler head 720 relative to the tumor or diseased portion 202 of the colon. If one or more of the bumpers 785 comprise lights, the surgeon may view the lights through the colon wall as indicated in FIG. 37.

Once the surgeon has located the stapler head 720 in the desired location within the proximal portion 201 of the colon 200, the surgeon may then retract the detection members 781 into the hook and detection housing 770 by rotating the detection knob 791 in a direction that is opposite to the direction in which the detection members 781 were caused to be extended. The acquisition hook members 780 may then be extended to pierce through and acquire the adjacent portions of the proximal colon wall 201. In alternative embodiments, however, the surgeon may elect to maintain the detection members 781 in their extended positions as shown in FIG. 37.

In doing so, the detection members 781 may produce some "hoop stress" in the colon wall which may assist in the acquisition and piercing of the proximal colon wall 201 by the acquisition hook members 780.

To cause the acquisition hooks 780 to engage and penetrate the proximal colon portion 201, the surgeon advances the hook and detection housing 770 distally by moving the hook switch 790 in the distal direction (arrow 792 in FIG. 32). Movement of the hook and detection housing 770 in the distal direction causes the acquisition hook members 780 to move axially out of their respective hook lumens 772. As the distal ends of the acquisition hook members 780 exit their respective hook lumens 772, they move radially outward to engage and pierce through adjacent portions of the proximal colon wall 201. See FIG. 37. Once the hook members 780 have pierced and engaged the adjacent portions of the proximal colon wall 201, the surgeon moves the hook switch 790 in the proximal direction (represented by arrow 794 in FIG. 32) to retract the acquisition hook members 780 into their respective hook lumens 772 as well as retract the hook and detection housing 770 back to its starting position. The barbs 784 on the distal ends of the acquisition hook members 780 draw the engaged portions of the proximal colon wall 201 into a position similar to the position illustrated in FIG. 9. Once the portions of the proximal colon portion 201 have been drawn into the position illustrated in FIG. 9, the surgeon may then complete the procedure by performing the same actions described above with respect to the circular stapler 10.

Figure 38:
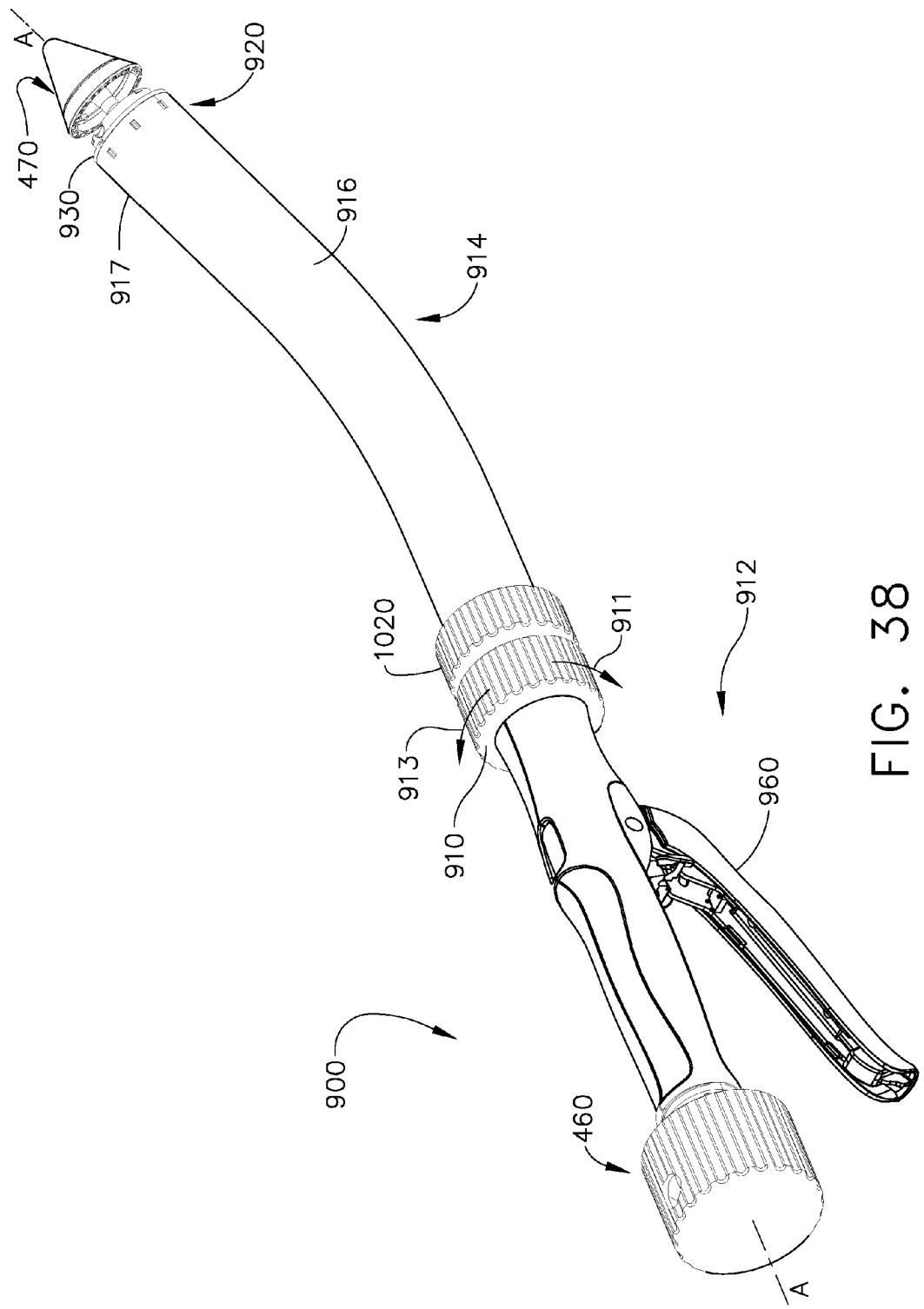
FIG. 38 is a perspective view of another circular stapling instrument of various non-limiting embodiments of the present invention.

FIG. 38 illustrates another circular stapler 900 according to various non-limiting embodiments of the invention. The circular stapler 900 generally includes a handle assembly 912 that has an elongated shaft 914 protruding therefrom. The elongated shaft 914 may define a central axis A-A. As can be seen in FIG. 38, the elongate shaft 914 includes a rigid outer sheath 916 that has a stapler head 920 located at the distal end 917 thereof. In various non-limiting embodiments, the stapler head 920 is configured to operably support a circular staple cartridge 930 therein. Such circular staple cartridges 930 are known in the art and may generally support one, two, or more than two circumferentially spaced and staggered rows of staples 36 therein as was described hereinabove. A conventional annular knife 940 is coaxially and movably supported within the stapler head 920. See FIG. 39.

The circular stapler 900 further includes a firing shaft 950 that is supported within the rigid outer sheath 916 for selective axial travel therein. See FIG. 39. A distal end portion 952 of the firing shaft 950 has an outer staple driver portion 954 thereon for engagement with each of the staples 36 in the outer row 32 of staples 36 in the staple cartridge 930. In addition, the distal end portion 952 of the firing shaft 950 has an inner staple driver portion 956 configured for engagement with each of the staples 36 in the inner row 34 of staples 36 within the staple cartridge 930. As can also be seen in FIG. 39, for example, the distal end portion 952 of the firing shaft assembly 950 further has a flanged portion 958 that is configured to engage the annular knife 940. Thus, as will be discussed in further detail below, axial advancement of the firing shaft 950 in a distal direction "DD", will cause the staples 36 to be driven out of the staple cartridge 930 as well as the annular knife 940 to advanced distally.

In various non-limiting embodiments, the firing shaft 950 may interface with a firing trigger 960 that is operably coupled to the handle assembly 912. See FIG. 38. As can be seen in FIG. 38, the firing trigger 960 may be pivotally coupled to the handle assembly 912 such that when the firing trigger 960 is pivoted toward the handle assembly 912, the firing shaft 950 is moved in the distal direction DD. As was discussed above, such firing trigger arrangements are known in the art and therefore will not be discussed in detail herein.

Figure 39:
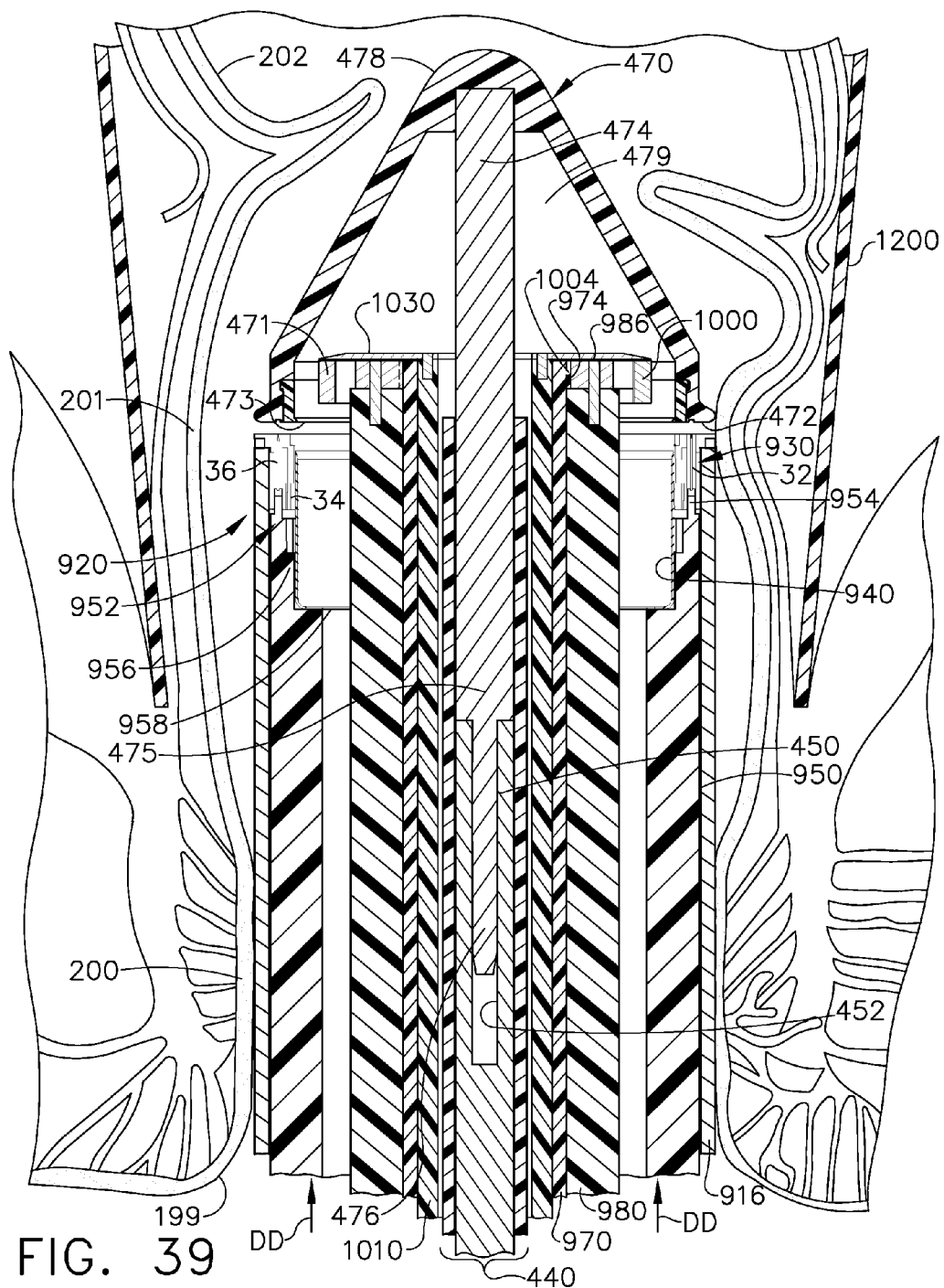
FIG. 39 is a cross-sectional view of a distal end portion of the elongated shaft of the circular stapling instrument of FIG. 38 inserted into the proximal portion of a tubular organ such as a colon.

As shown in FIG. 39, various non-limiting embodiments may also include a hollow deployment shaft 970 that is coaxially supported within a hollow tissue acquisition shaft 980. The proximal end of the deployment shaft 970 is operably attached to an arm deployment knob 910 that is rotatably supported on the handle assembly 912 in the various manners described above. Thus, rotation of the arm deployment knob 910 on the handle assembly 912 will result in the rotation of the deployment shaft 970 about the central axis A-A. More specifically and with reference to FIG. 40, in various embodiments, a distal end 972 of the deployment shaft 970 protrudes through a hole 982 in the tissue acquisition shaft 980 and has a drive gear 974 attached thereto. A distal end 984 of the tissue acquisition shaft 980 is configured to operably support at least one tissue acquisition member or arm 1000 thereon. Two or more tissue arms 1000 are preferable. In the non-limiting embodiment depicted in FIG. 40, a total of four tissue arms 1000 are pivotally pinned to the distal end 984 of the tissue acquisition shaft 980 by corresponding pins 986.

Figure 41:
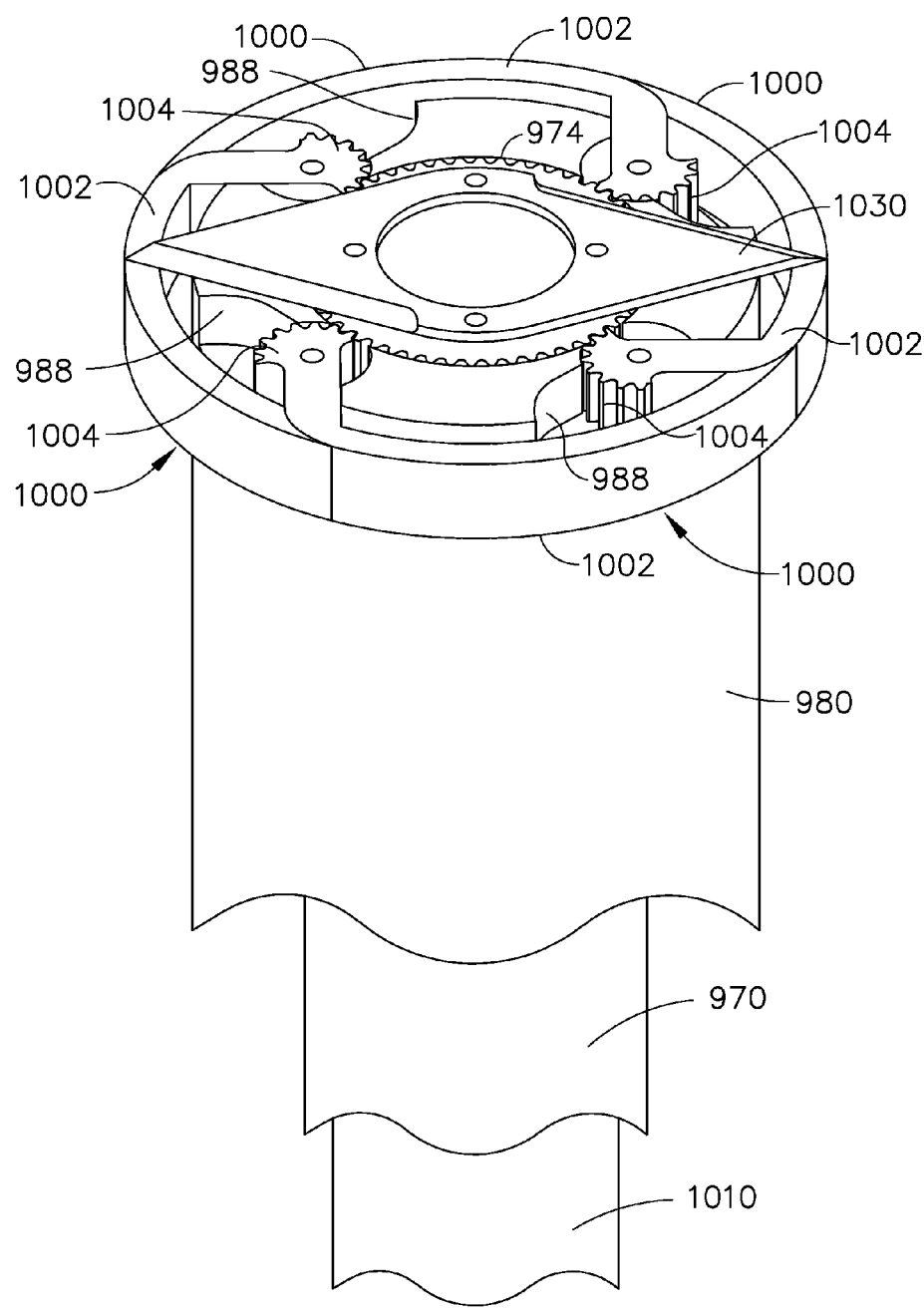
FIG. 41 is a partial perspective view of the tissue acquisition shaft of FIG. 40 with the tissue arms thereof in a retracted position.
Figure 42:
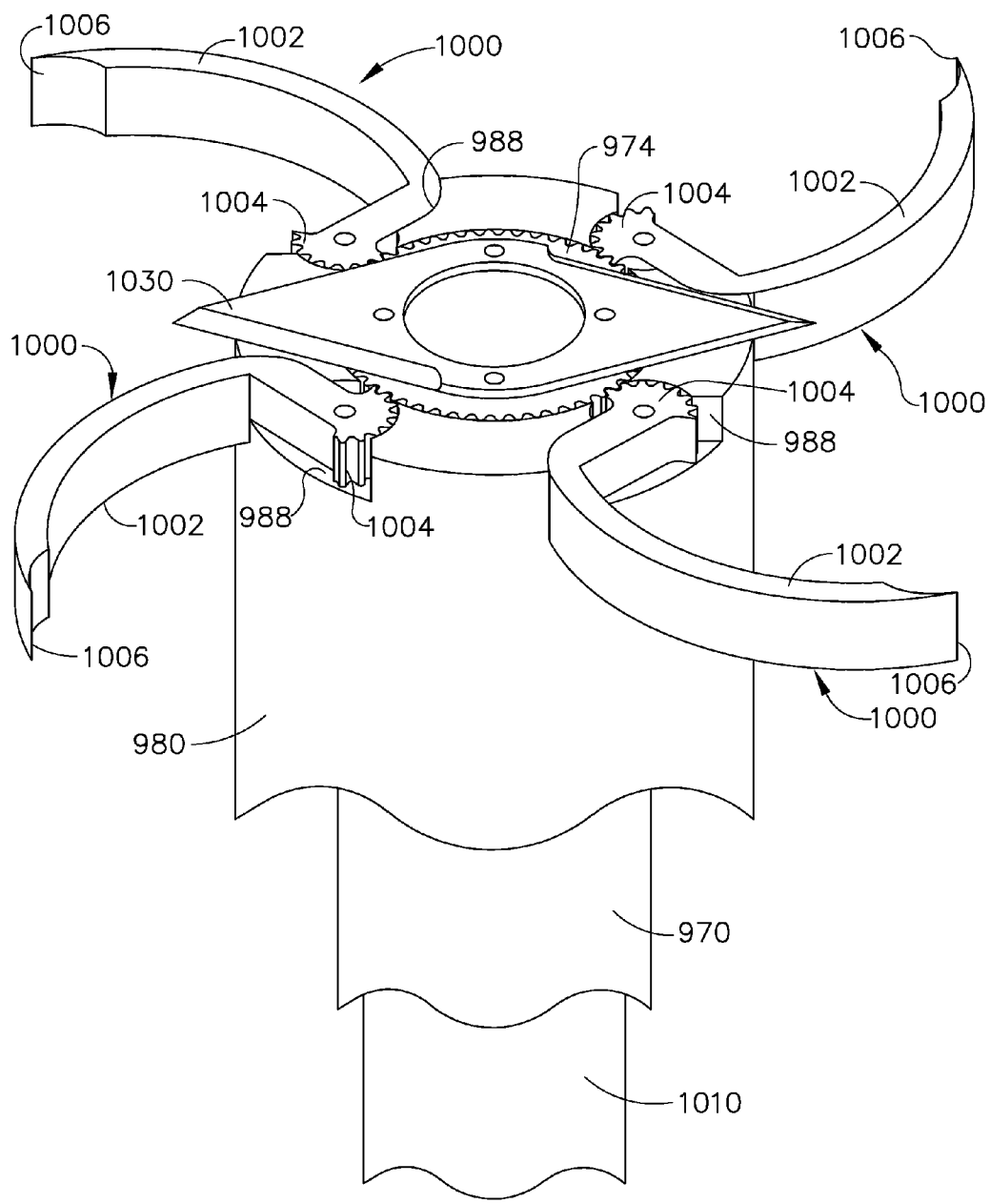
FIG. 42 is a perspective view of the acquisition shaft of FIG. 41 with the tissue arms thereof in deployed positions.
Figure 43:
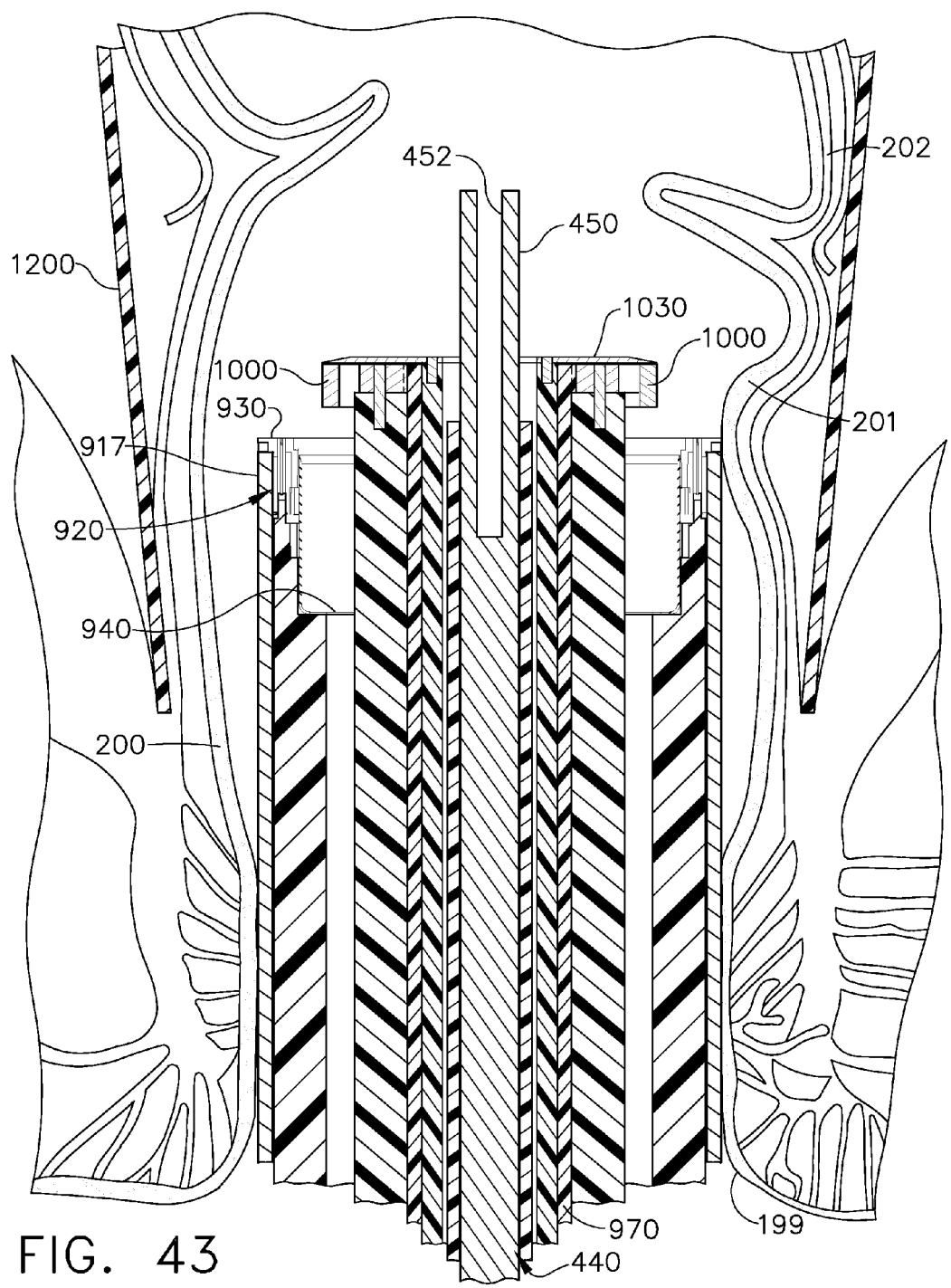
FIG. 43 is a partial cross-sectional view of a distal end portion of the elongated shaft of the surgical instrument of FIG. 38 inserted into a proximal portion of the colon with the anvil assembly removed therefrom.
Figure 44:
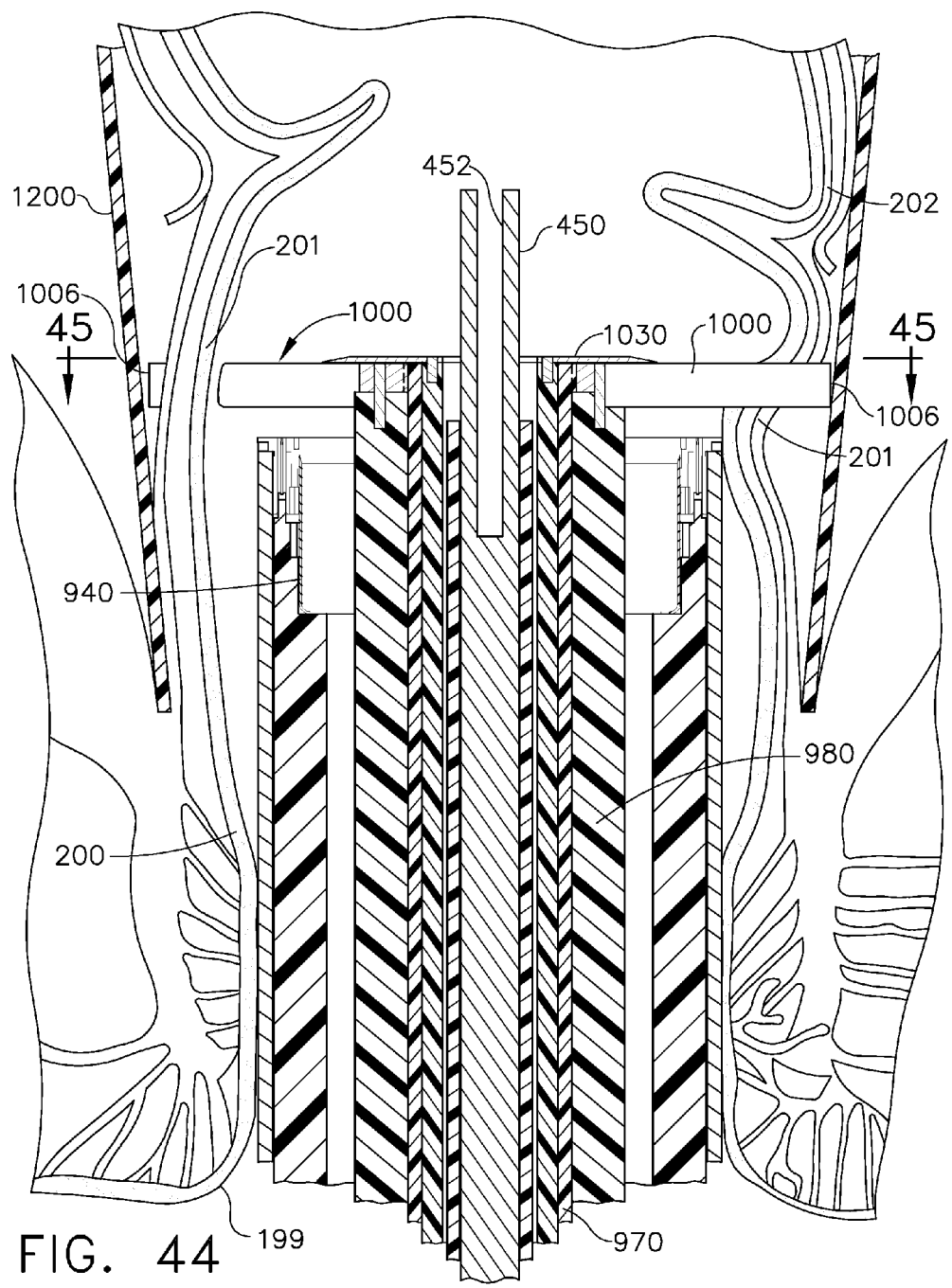
FIG. 44 is a partial cross-sectional view of the distal end portion of the elongated shaft with the tissue acquisition arms deployed through a proximal portion of the colon.
Figure 45:
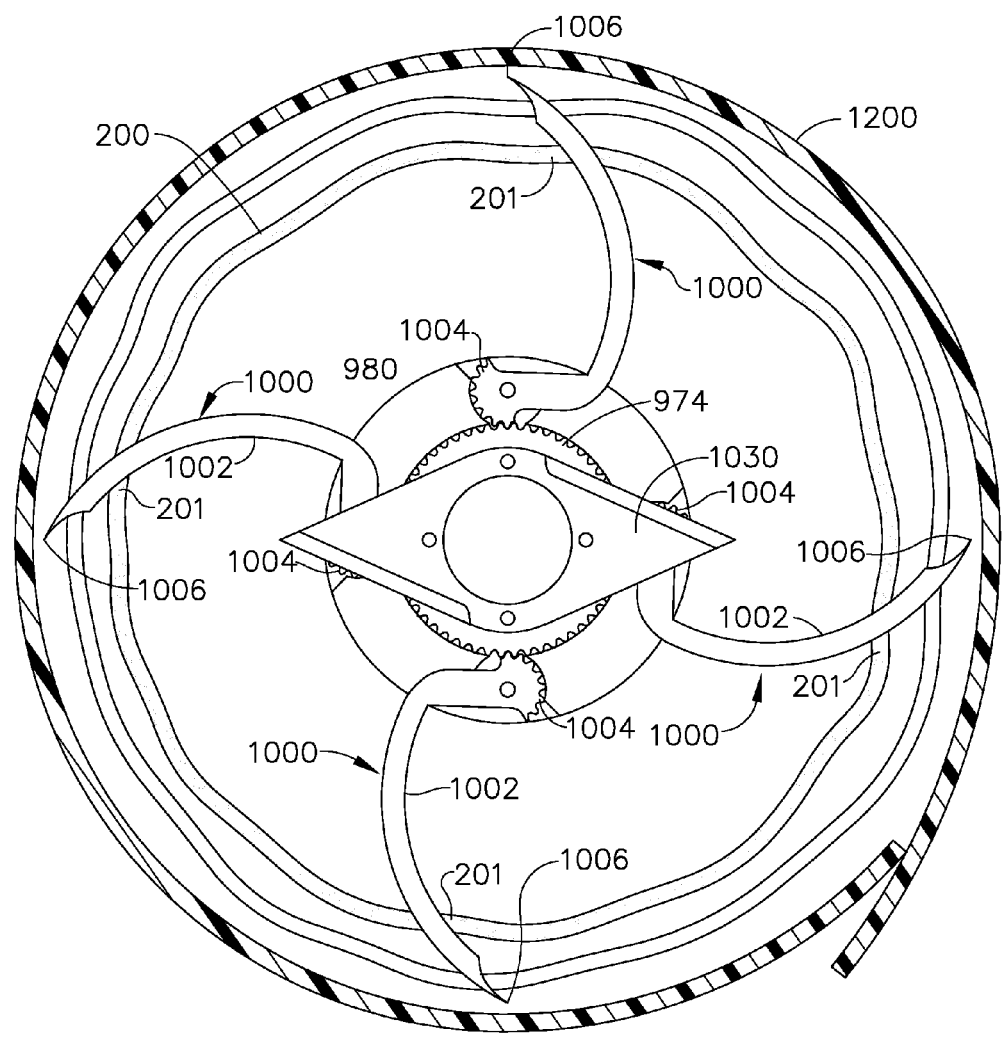
FIG. 45 is a top cross-sectional view of the distal end portion of the elongated shaft take along line 45-45 in FIG. 44.
Figure 46:
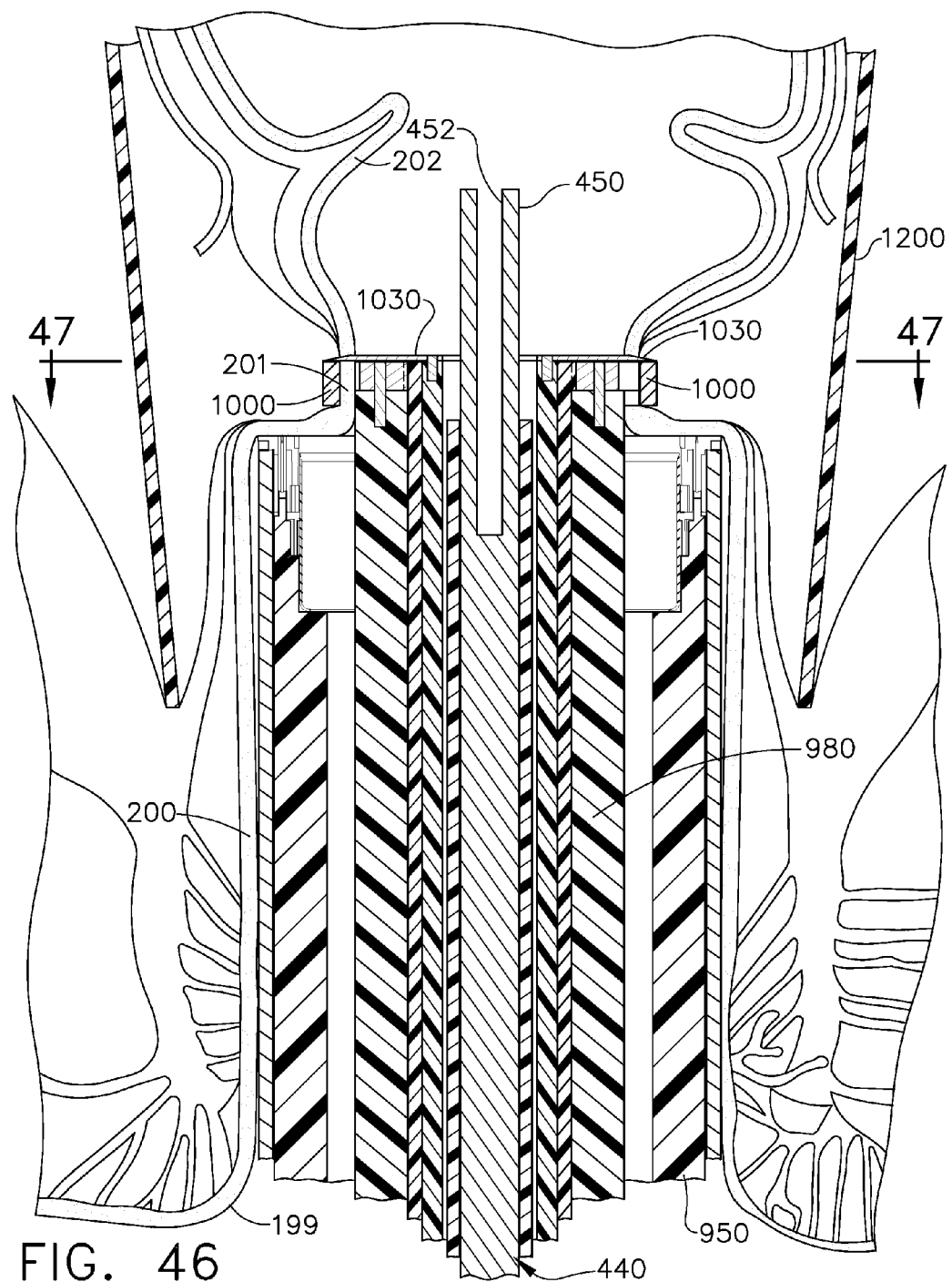
FIG. 46 is another partial cross-sectional view of the distal end portion of the elongated shaft after the tissue acquisition arms have been deployed through the proximal portion of the colon and then moved to a retracted position wherein the pierced proximal portion is trapped between the tissue acquisition arms and the tissue acquisition shaft.
Figure 47:
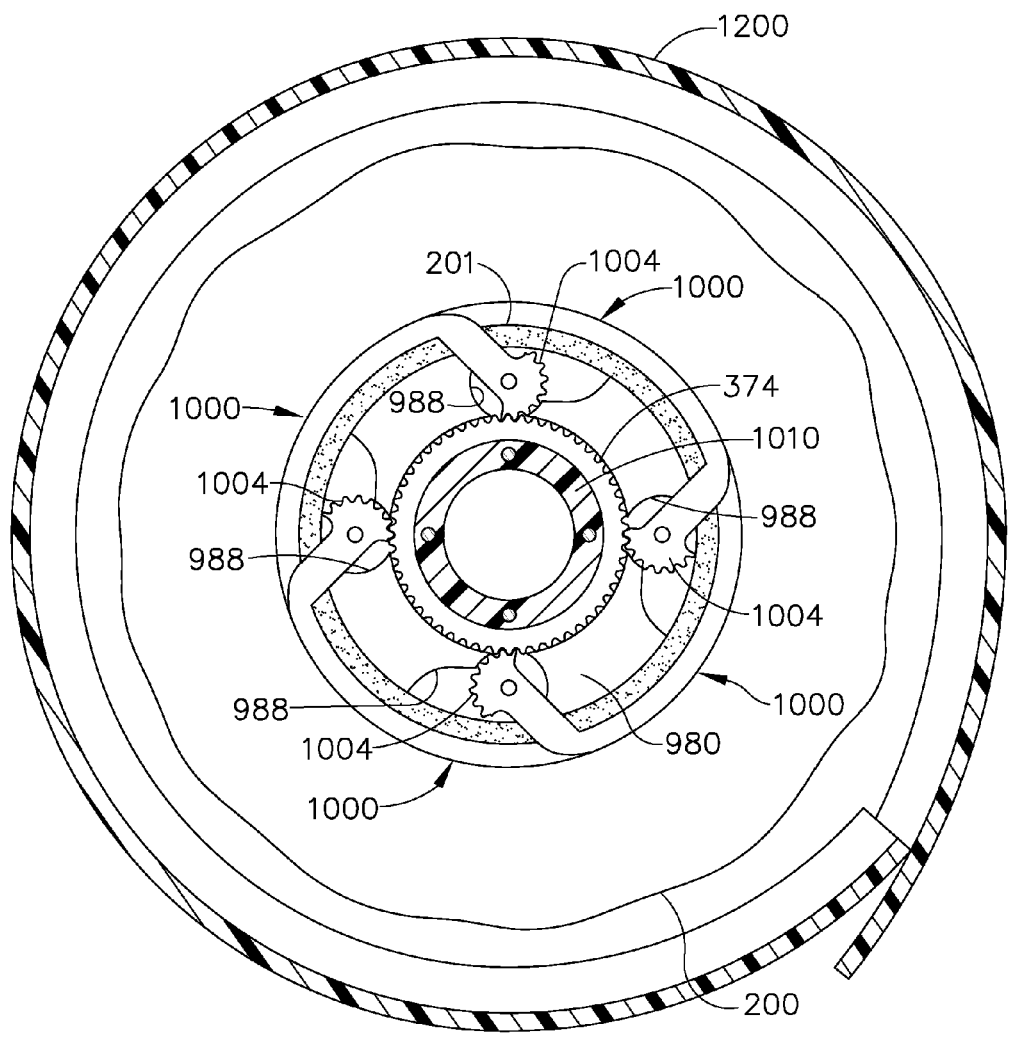
FIG. 47 is a top cross-sectional view of the distal end portion of the elongated shaft of FIG. 46 taken along line 47-47 in FIG. 46.
Figure 48:
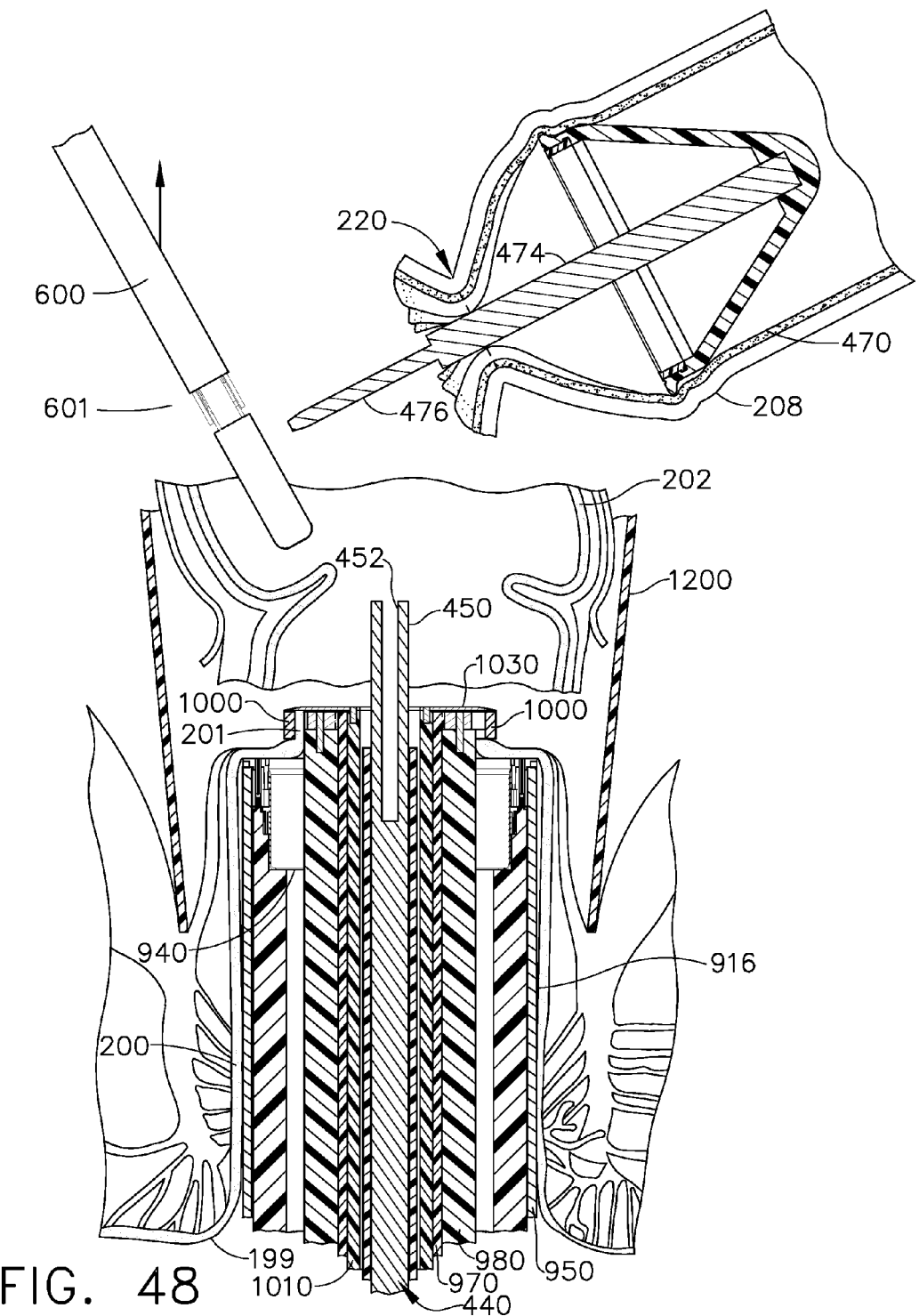
FIG. 48 is a partial cross-sectional view of the distal end portion of the elongated shaft with the diseased portion of the colon being severed from the proximal portion and distal portion and being removed from the colon by conventional graspers.

Each tissue arm 1000 may have a body portion 1002 that may be fabricated from, for example, stainless steel (300 or 400 series), titanium, titanium-steel composite, ceramic, etc. and have a driven gear 1004 attached thereto or formed thereon. The driven gear 1004 of each tissue arm 1000 is movably supported within a corresponding arm cavity 988 formed in the distal end 984 of the tissue acquisition shaft 980. Each driven gear 1004 is in meshing engagement with the drive gear 974 on the deployment shaft 970. Thus, rotation of the deployment shaft 970 will result in the pivotal deployment of the tissue arms 1000 from the retracted position depicted in FIG. 41 to the deployed position depicted in FIG. 42. In various embodiments, the body portion 1002 of each tissue arm 1000 may further have a tissue piercing tip 1006 formed thereon or otherwise attached thereto.

Figure 40:
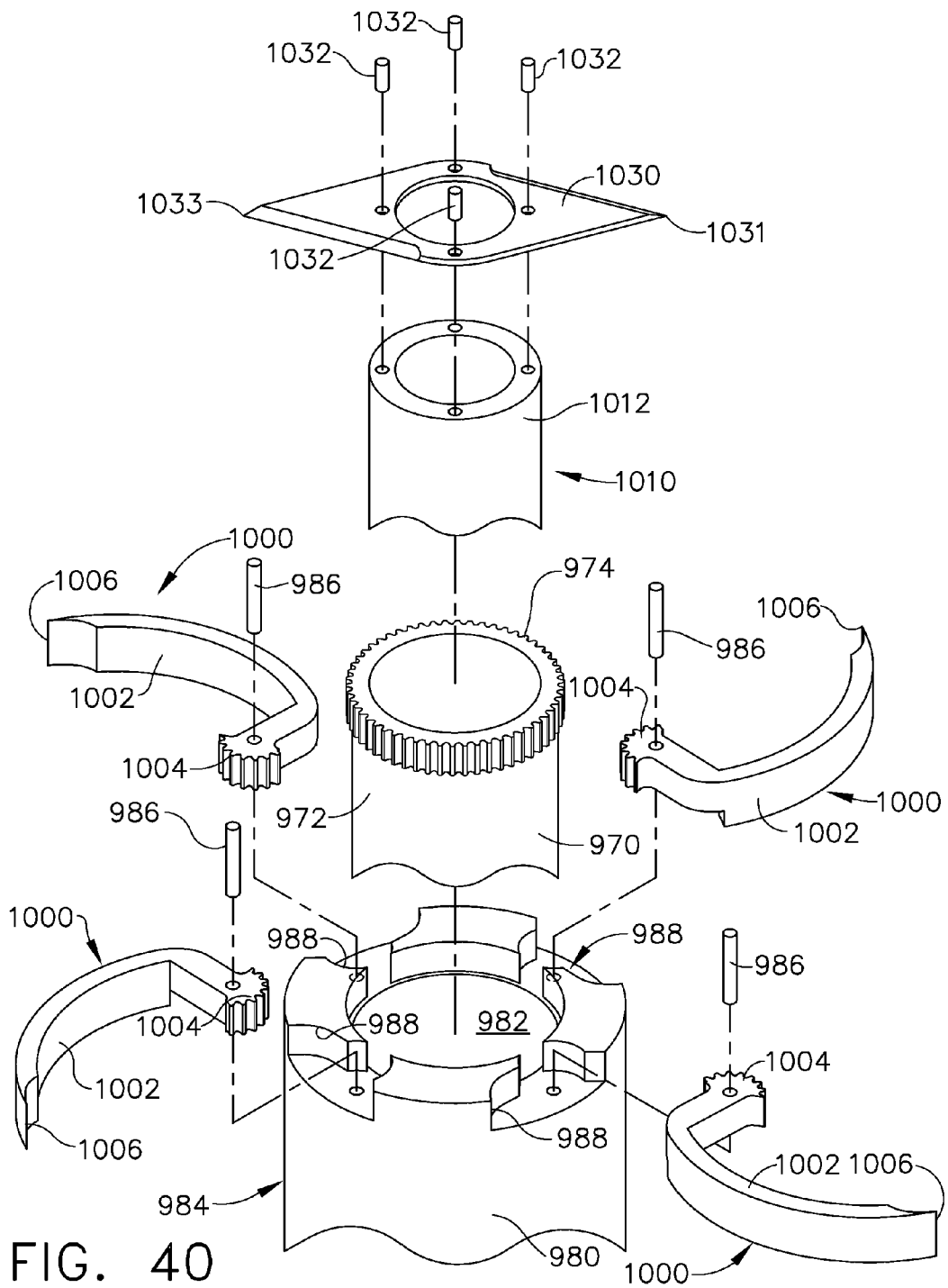
FIG. 40 is an exploded assembly view of distal end portions of a tissue acquisition shaft, a deployment shaft and a knife shaft of various non-limiting embodiments of the present invention.

In various embodiments, a knife shaft 1010 is coaxially received within the deployment shaft 970 and interfaces with a knife knob 1020 (FIG. 38) rotatably supported on the handle assembly 912 such that rotation of the knife knob 1020 results in the rotation of the knife shaft 1010. The knife shaft 1010 further has a distal end 1012 that protrudes out of the distal ends 972, 984 of the deployment shaft 970 and the tissue acquisition shaft 980, respectively. See FIG. 40. A knife 1030 may be removably attached to the distal end 1012 of the knife shaft 1010 by, for example, pins 1032 or other suitable fasteners. In various embodiments, the knife 1030 may be substantially planar and have diametrically opposed tissue-piercing points 1031, 1033 formed thereon as shown in FIG. 40.

As can also be seen in FIG. 39, various non-limiting embodiments may further include an anvil shaft assembly 440 that includes a distal end post 442 that protrudes from a portion of the firing shaft 950 that coaxially extends within the deployment shaft 970 for selective axial travel therein. The distal end post 442 supports a distal anvil connector 450 therein that is coupled to an adjustment knob 460 that is rotatably supported on the handle assembly 312 in the various manners discussed above.

The circular stapler 900 further includes an anvil 470 as shown in FIG. 39. In various non-limiting embodiments, the anvil 470 includes an anvil base 471 that has a series of staple forming pockets 472 therein. The anvil base 471 may further define a shear edge 473 for facilitating the shearing of tissue by the annular knife 940. The anvil 470 may further include an anvil shaft 474 that is removably attachable to the distal anvil connector 450. In particular, a coupling stem 476 protrudes from the proximal end 475 of the anvil shaft 474 and is sized to be slidably received in a passage 452 in the anvil shaft assembly 450. The anvil 470 may further have an anvil cap 478 thereon that serves to define a tissue cavity 479 therein as illustrated in FIG. 39.

One exemplary method of using the circular stapler 900 will be described with reference to FIGS. 39 and 43-51. Turning first to FIG. 39, the stapler head 920 is inserted into a tubular organ such as the colon 200 through the patient's anus 199. The stapler head 920 is located in the proximal portion 201 of the colon 200 that is adjacent to a diseased portion 202. Thereafter, the tissue arms 1000 are radially deployed by rotating the arm deployment knob 910 in a first direction (represented by arrow 911 in FIG. 38) which also rotates the deployment shaft 970. Rotation of the deployment shaft 970 in the first direction also rotates the drive gear 974 which is in meshing engagement with the driven gear portions 1004 of each tissue arm 1000. Thus, rotation of the drive gear 974 in the first direction causes the tissue arms 1000 to be radially deployed. As the tissue arms 1000 are radially deployed, the tissue piercing tips 1006 thereof pierce through proximal portion 201 of the colon 200. See FIGS. 44 and 45. The surgeon may then rotate the arm deployment knob 910 in the opposite or second direction (represented by arrow 913 in FIG. 38) to retract the tissue arms 1000 into their retracted position (FIG. 20). As the tissue arms 1000 are retracted, the pierced proximal portion 201 of the colon 200 is carried by the tissue arms 1000 such that the portion 201 is gathered between the tissue arms 1000 and the arm shaft 980 in a confronting position adjacent the staple cartridge 930. Thereafter, the surgeon may rotate the knife knob 1020 to cause the knife 1030 to rotate and sever the diseased portion 202 of the colon 200 from the proximal portion of the colon 201. The diseased portion 202 may be transected from a distal portion 208 of the colon using a conventional laparoscopic tissue severing instrument (not shown) inserted through a trocar sleeve (not shown) positioned in the abdominal cavity 601. After the diseased portion 202 has been cut away from the proximal portion 201 of the colon 200 and the distal portion 208, the diseased portion 202 may be removed through the trocar sleeve with a conventional grasping instrument 600. See FIG. 48.

Figure 49:
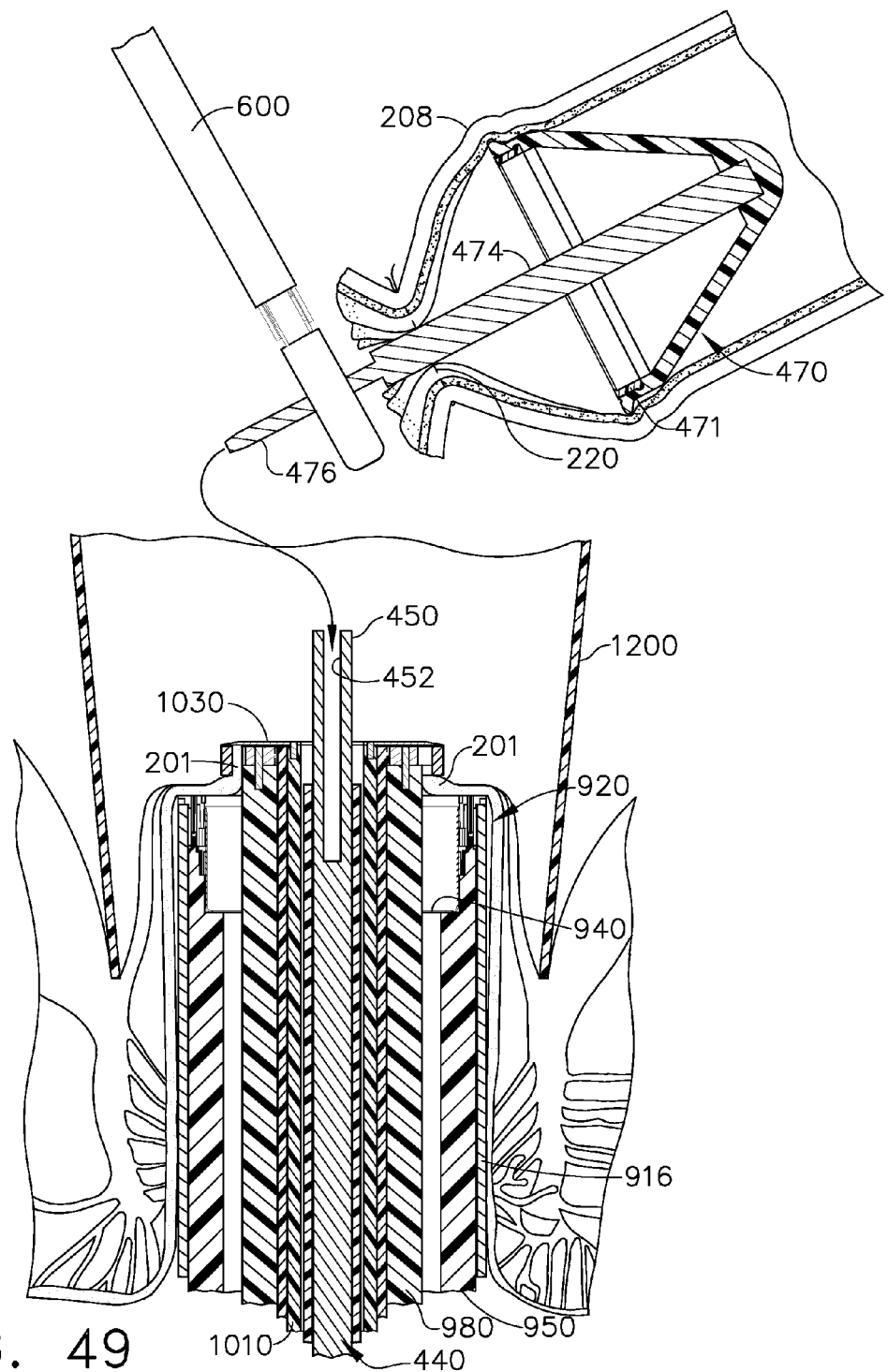
FIG. 49 is a partial cross-sectional view of the elongated shaft after the anvil has been inserted into a distal portion of the colon and secured thereto by a purse-string suture arrangement.

The surgeon may then orient the anvil 470 within the distal portion 208 of the colon 200 such that the anvil shaft coupling stem 476 of the anvil shaft 474 protrudes out of the distal portion 208 of the colon 200 as shown in FIG. 49. The surgeon may then tie the end of the distal colon portion 208 around the anvil shaft 474 using what is known in the art as a "purse string suture" 220. Once the distal colon portion 208 has been sutured around the anvil shaft, 474, the coupling stem 476 of the anvil shaft 474 is inserted into the passage 452 in the anvil shaft assembly 450. The coupling stem 476 may be sized relative to the passage 452 to establish a frictional fit therebetween to retain the coupling stem 476 therein, yet permit the coupling stem 476 to be removed therefrom at a later time. See FIG. 49.

Figure 50:
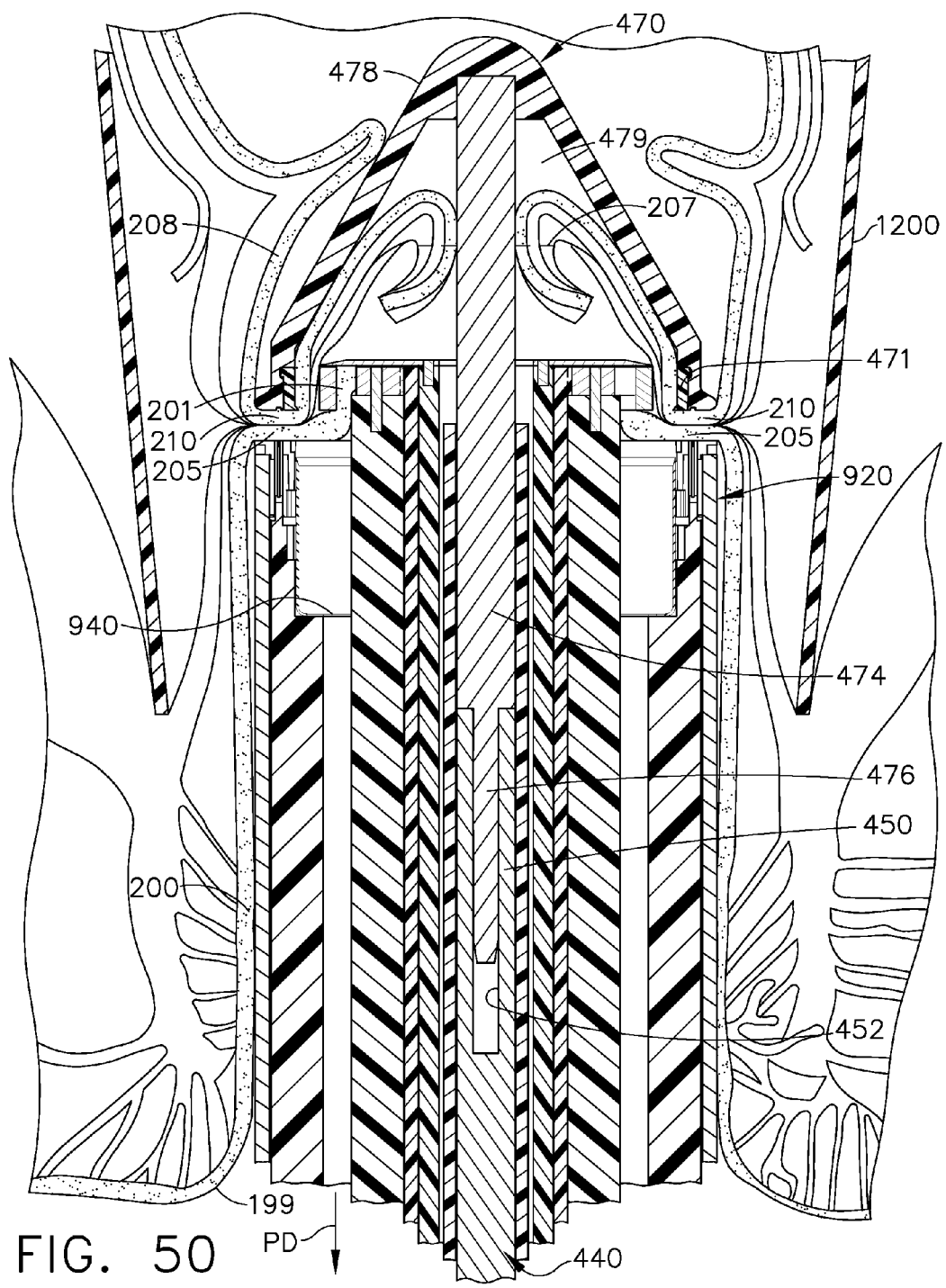
FIG. 50 is a cross-sectional view of the elongated shaft of FIG. 49 after the anvil has been coupled to the anvil assembly thereof and drawn into confronting relationship with the staple cartridge therein.
Figure 51:
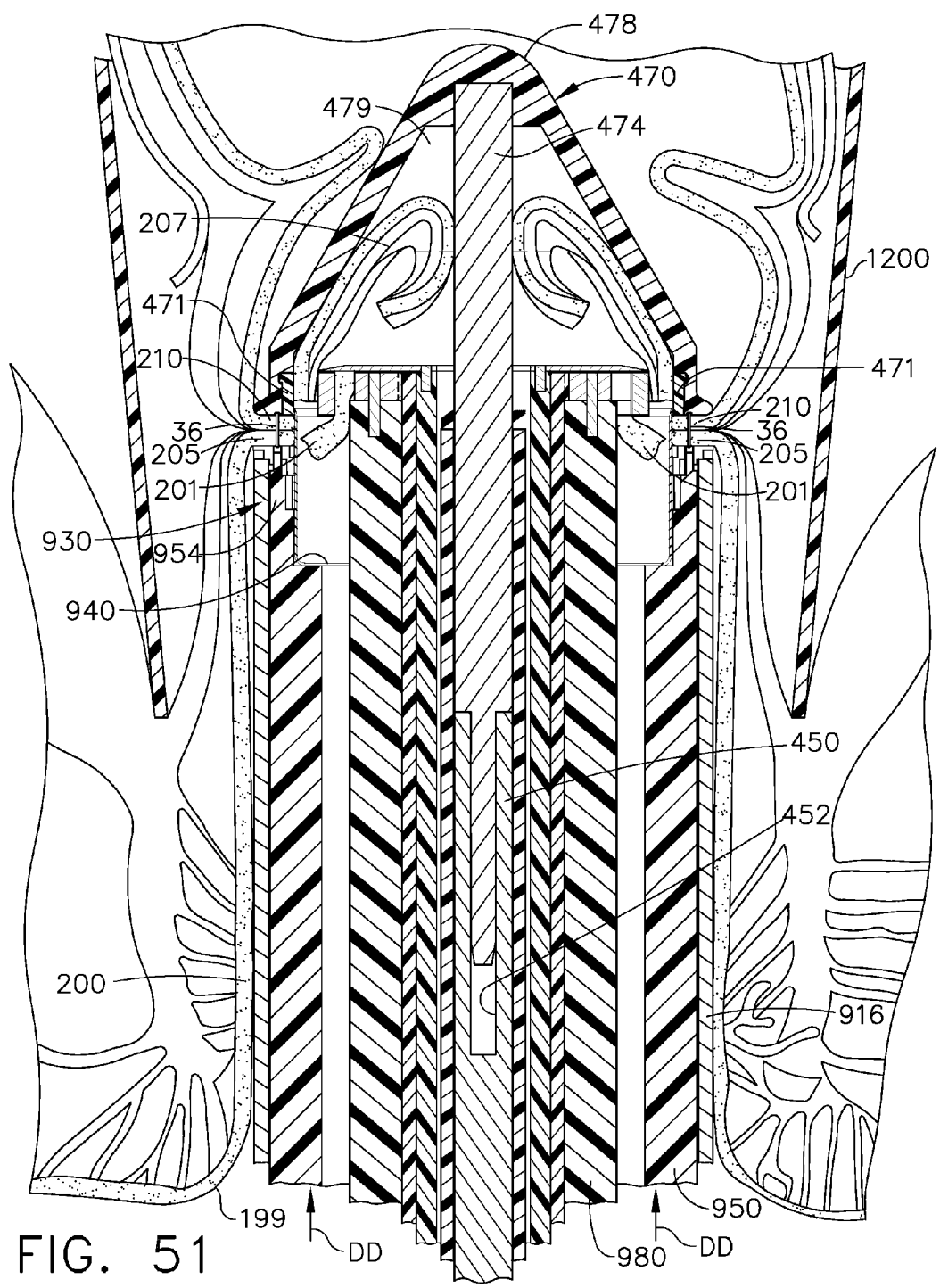
FIG. 51 is a cross-sectional view of the elongated shaft of FIG. 50 after the staple cartridge had been fired and the annular cutting member advanced through the stapled tissue portions.

The surgeon then draws the anvil 470 toward the stapler head 920 (in the proximal direction "PD") by rotating the anvil control knob 460 in the appropriate direction until portions 205, 210 of the colon 200 are clamped between the anvil 470 and the staple cartridge 930 as shown in FIG. 50. Thereafter, the surgeon actuates the firing trigger 960 to axially advance the firing shaft 950 in the distal direction "DD". As firing shaft 950 is advanced distally, the staple driver portion 954 serves to drive the staples 36 through the portions 205, 210 of colon 200 into the anvil forming pockets 472 in the anvil base 471. The firing shaft 950 also advances the annular knife 940 to sever the colon portions 201, 207 from colon portions 205, 210 respectively. The surgeon may then move the anvil 470 in the distal direction "DD" to release the stapled colon portions 205, 210 from between the anvil 470 and the stapler head 920. The instrument 900 may then be removed from the colon 200. See FIG. 51. The severed portion 207 is captured in the anvil cavity 479 and the severed portion 201 is retained between the tissue arms 1000 and the arm shaft 980. Thus, the cut portions 201, 207 of the colon 200 are removed from the repaired colon when the instrument 900 is withdrawn therefrom.

Figure 52:
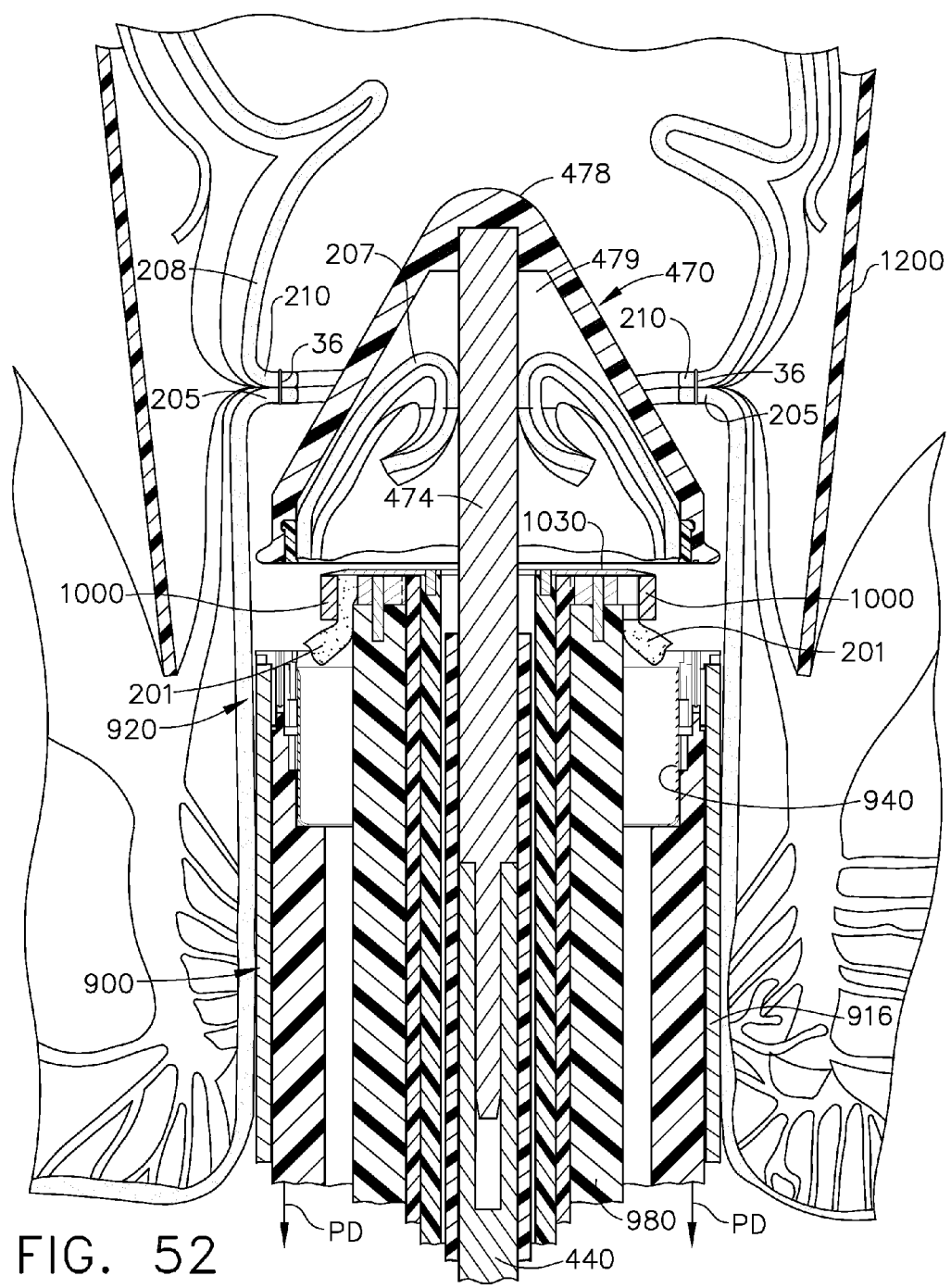
FIG. 52 is a cross-sectional view of the elongated shaft of FIG. 51 being withdrawn from the colon after completion of the stapling procedure.
Figure 53:
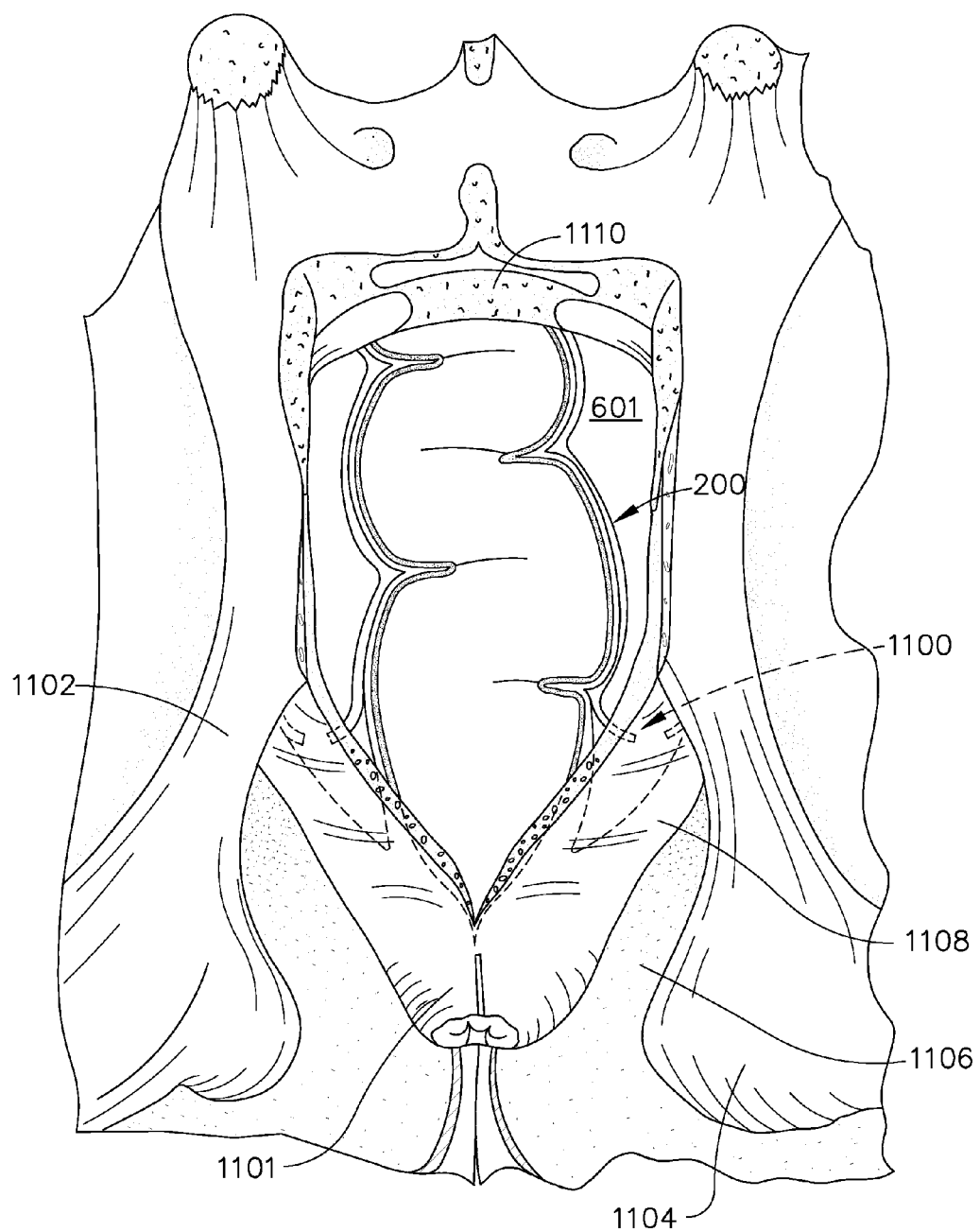
FIG. 53 is a view of a portion of a patient's opened abdominal cavity illustrating various tissues and structures adjacent a portion of the colon.

As the surgeon performs the above described procedures or other related procedures in that region of the body, care has to be taken to avoid inadvertently damaging adjacent soft tissues and bone structures. FIGS. 52 and 53 illustrate some of the adjacent tissue and bone structures that are adjacent to the colon 200. In FIG. 52, the peritoneum 1100 has been dissected to illustrate, for example, the sphincter ani 1101, the sacrotuberous ligament 1102, the ischtal tuberosity 1104, the ischiorectal fossa 1106, levator ani 1108, and the third sacral vertebra 1110. FIG. 53 further illustrates the para rectal fossa 1112, the sacrogenital fold 1114, the ureter 1116, the ductus diferens 1118, the bladder 1120, the paravesical fossa 1122, and the transvesical folds 1124. The surgeon must also be careful not to damage the muscles, nerves, vessels and arteries along the inter wall of the peritoneum 1100 when accessing the portion of the colon 200 to be transected.

FIGS. 54-57 illustrate use of a protective sheath 1200 of a non-limiting embodiment of the present invention. In various embodiments, the sheath 1200 may be fabricated from, for example, Kevlar, polyethylene, Nylon, etc. and be stressed in a fashion that naturally makes it want to coil. See FIG. 55. In various embodiments, measurement or reference indicia 1202 may be provided on the sheath 1200 to assist the surgeon in locating the operable portion of a surgical instrument (e.g., the stapler head of a circular stapler) and to prevent accidental damage of adjacent nerves, vessels and tissue. In still other embodiments, the sheath 1200 may be fabricated from a magnetic sensitive film that would enable it to be magnetically attracted to the operable portion of the instrument to protect the adjacent anatomical structures and tissues from, for example, portions of the instrument that might damage adjacent tissues, muscles, bones, nerves, etc. if the instrument portions were brought into inadvertent contact therewith. In further alternative embodiments, the sheath 1200 may have a magnetic interaction ring or portion that is attracted to the stapler head. Thus, at least a portion of the sheath 1200 may be magnetic or otherwise have magnetic material attached thereto.

Figure 54:
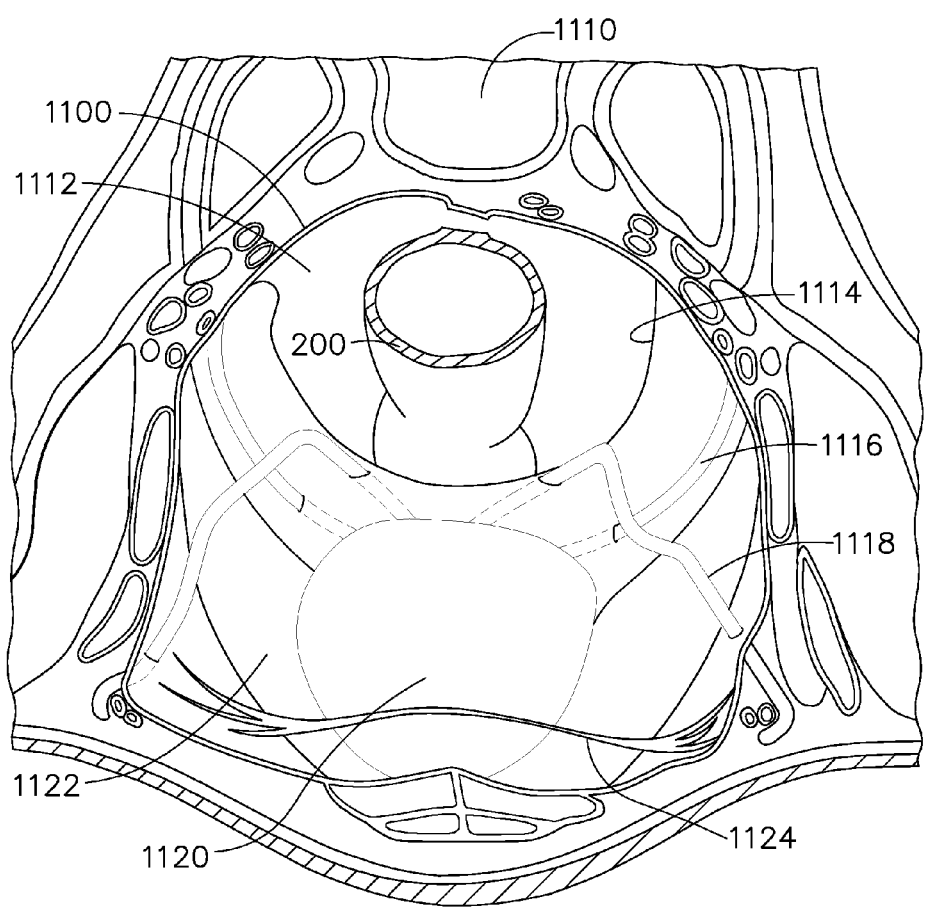
FIG. 54 is another partial view of the open abdominal cavity of FIG. 53.
Figure 55:
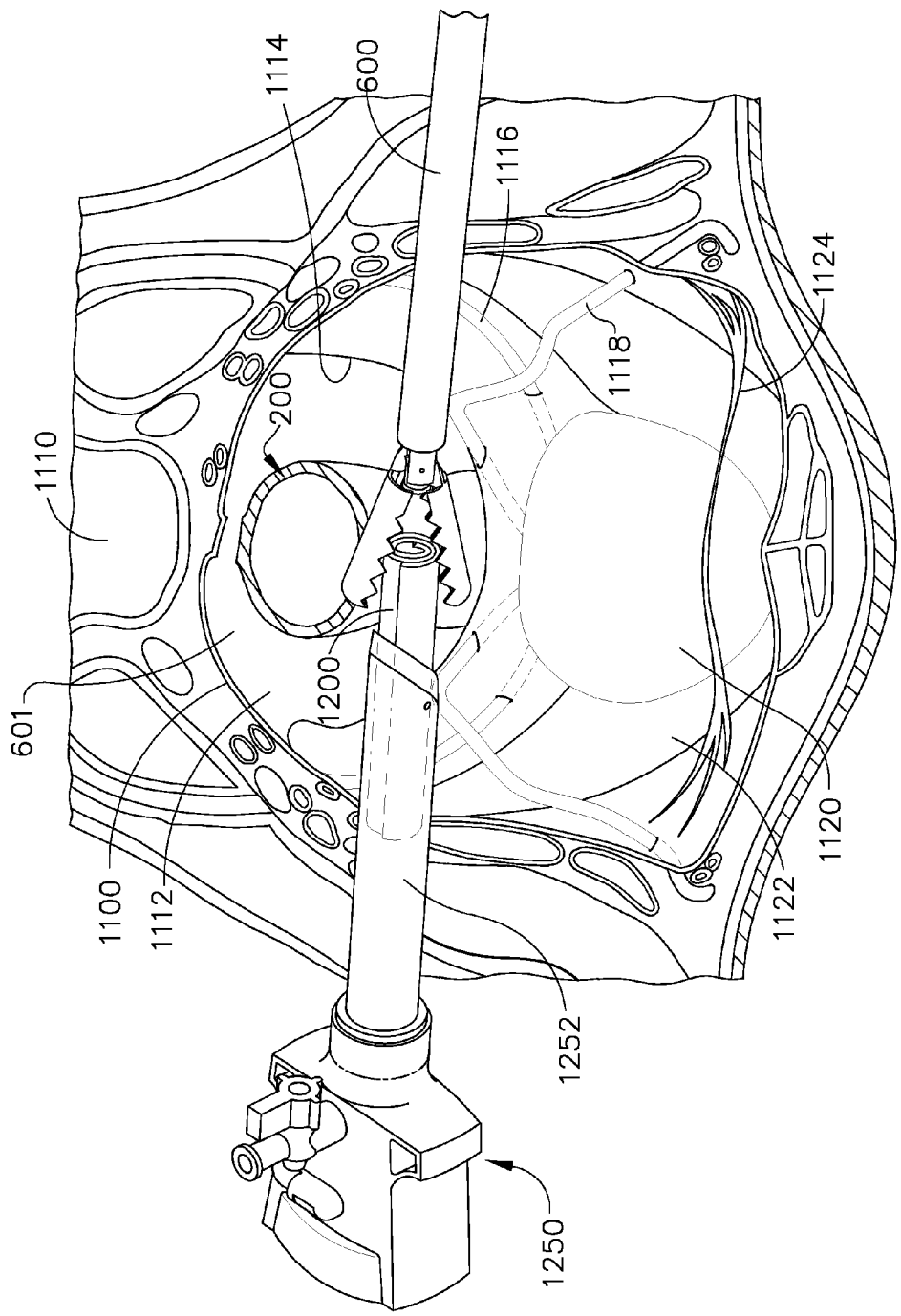
FIG. 55 is another view of the abdominal cavity of FIG. 53 illustrating the insertion of a trocar into the abdominal cavity to deliver a protective sheath embodiment of the present invention therein.
Figure 56:
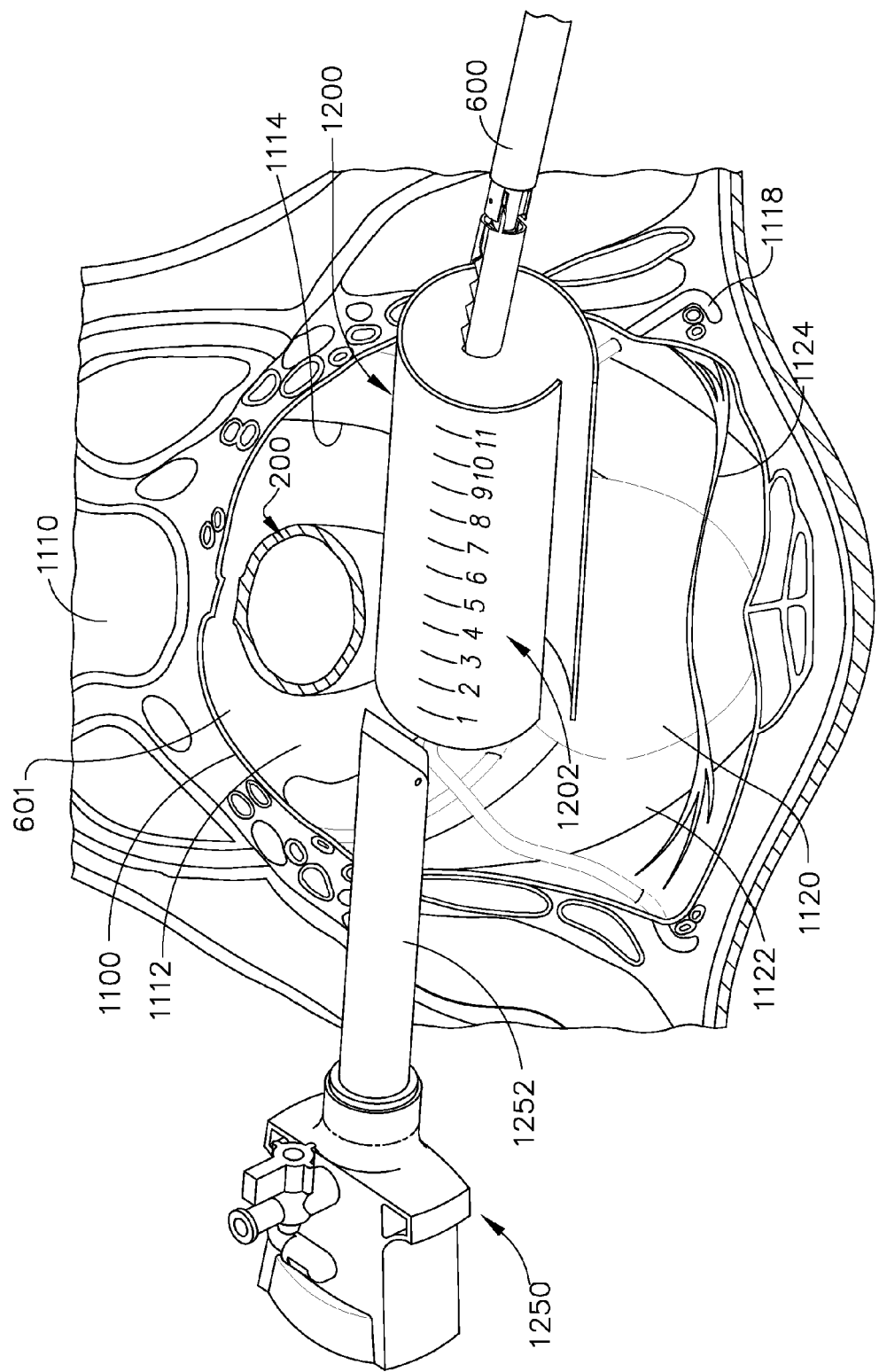
FIG. 56 is another view of the abdominal cavity of FIG. 55 with the protective sheath embodiment being withdrawn from the trocar sleeve by a conventional grasping device.
Figure 57:
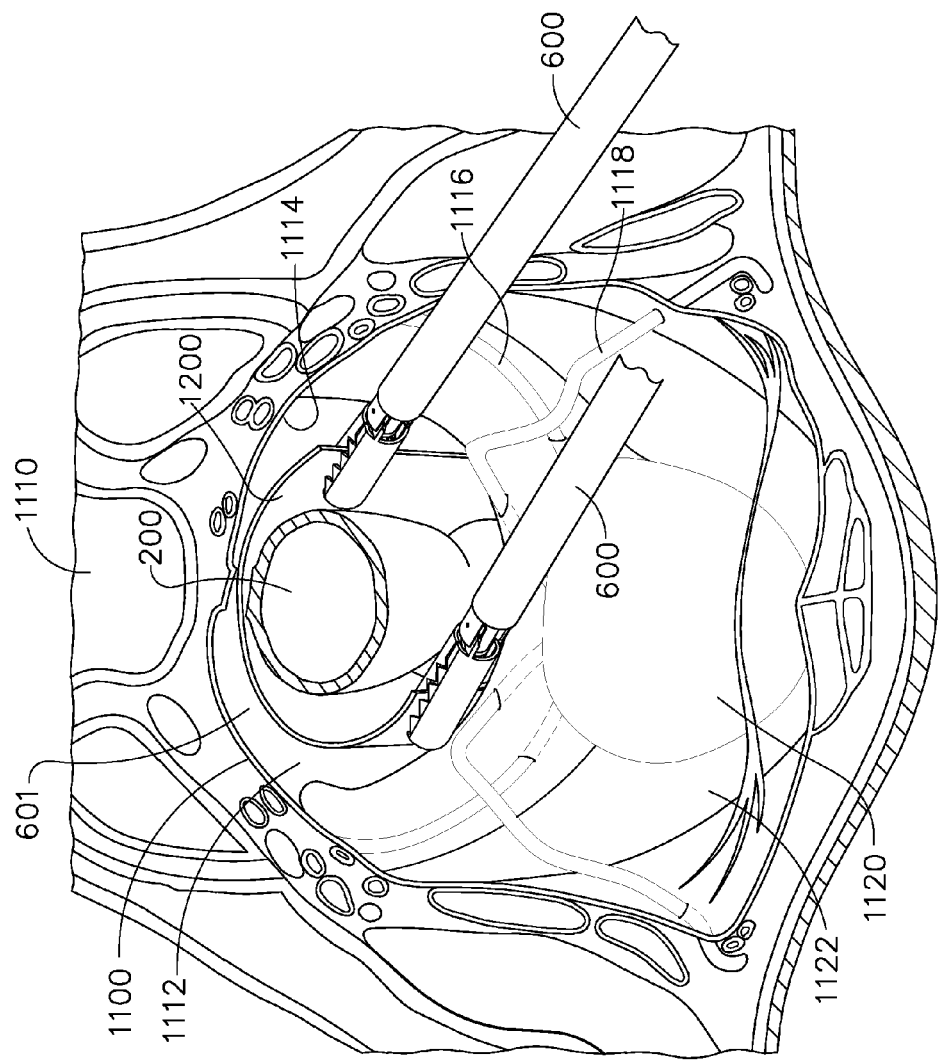
FIG. 57 is another view of the abdominal cavity of FIG. 56 illustrating one method of positioning the protective sheath around the circumference of a portion of the colon to be treated.
Figure 58:
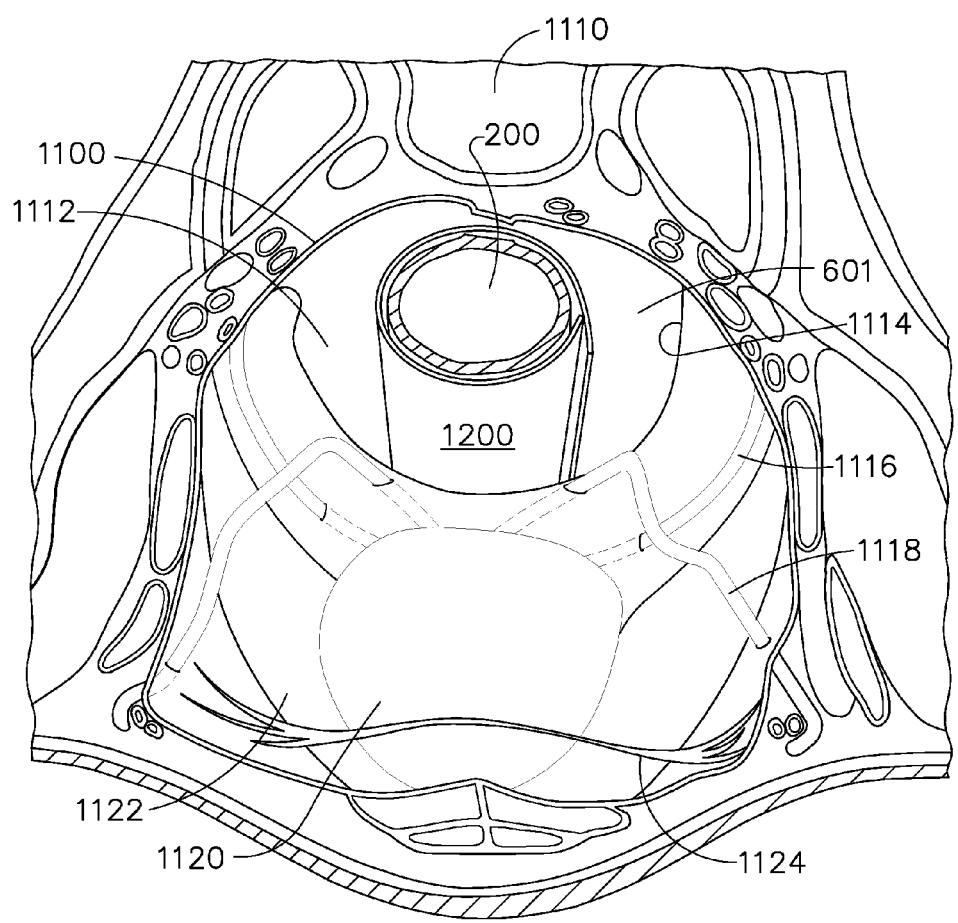
FIG. 58 is another view of the abdominal cavity of FIG. 57 after the protective sheath embodiment has been positioned around the outer circumference of the portion of colon to be treated.

The sheath 1200 may be installed through a cannula 1252 of a conventional trocar 1250 that is laparoscopically inserted through the abdominal wall into the abdominal cavity as shown in FIG. 54. A conventional laparoscopic grasping instrument 600 may be used as shown in FIGS. 54 and 55 to remove the sheath 1200 from the trocar cannula 1252. Thereafter, the surgeon may wrap the unrolled sheath 1200 around the colon 200 using conventional grasping devices 600 as shown in FIG. 56. FIG. 57 illustrates the sheath 1200 after it has been wrapped around the colon 200 and prior to commencing insertion of the circular stapling instrument into the colon. The natural coiling nature of the sheath serves to retain it in a coiled orientation about the colon 200.

The sheath 1200 of the present invention may be effectively employed to protect adjacent tissues and organs during use of any of the above-mentioned embodiments. See, for example, FIGS. 5-16, 23-31, 36, 39, and 43-51, wherein the sheath 1200 has been installed around the colon 200 in the above-described manner. In addition, the non-limiting embodiments of the sheath 1200 may be effectively used in connection with conventional circular stapling devices and the like without departing from the spirit and scope of the present invention. For those instrument embodiments that employ lights on the detection members or the like, the sheath 1200 may be fabricated from, for example, light sensitive film that would cause portions of the sheath 1200 to change color in those areas adjacent to the lighted detection members. See For example, the non-limiting embodiment depicted in FIG. 36.

The various embodiments of the present invention represent a vast improvement over prior circular staple arrangements and procedures associated therewith. While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument comprising:
    an elongated shaft defining a central axis and having a distal end portion configured to operably support a circular staple cartridge therein;
    a tissue acquisition shaft rotatably supported within said elongated shaft and having a distal portion that protrudes distally beyond the distal end portion of the elongated shaft; and
    at least one tissue acquisition member pivotally attached to said distal portion of the tissue acquisition shaft such that said at least one tissue acquisition member is selectively pivotable about a corresponding acquisition axis that is spaced from and substantially parallel to said central axis from a retracted position to deployed positions upon application of a deployment motion thereto.

2. The surgical instrument of claim 1 further comprising an annular cutting member that operably supported by said distal end portion of said elongated shaft for selective axial travel relative thereto.

3. The surgical instrument of claim 1 further comprising a deployment member operably supported within said elongated shaft and operably interfacing with each said at least one tissue acquisition member, said deployment member configured to receive said deployment actuation motion to cause said at least one tissue acquisition member to move between said retracted and deployed positions.

4. The surgical instrument of claim 3 wherein said deployment member comprises a deployment shaft extending through said elongated shaft and being selectively rotatably movable relative thereto, said deployment shaft in meshing engagement with each of said tissue acquisition members such that rotation of said deployment shaft in one direction about the central axis causes said tissue acquisition members to pivot from said retracted position to a deployed position and rotation of said deployment shaft in an opposite direction about said central axis causes said tissue acquisition members to pivot from said deployed position to said retracted position.

5. The surgical instrument of claim 1 further comprising at least one tissue acquisition pin protruding radially from said distal portion of said tissue acquisition shaft.

6. The surgical instrument of claim 1 wherein each one of said at least one tissue acquisition members has a tissue-piercing tip.

7. The surgical instrument of claim 1 wherein each said at least one tissue acquisition member has a tissue cutting edge formed thereon.

8. The surgical instrument of claim 7 further comprising a shear plate attached to said distal portion of said tissue acquisition shaft and cooperating with said cutting edge of each said tissue acquisition member to shear tissue drawn therebetween.

9. The surgical instrument of claim 8 wherein said at least one tissue acquisition member comprises four tissue acquisition members that each have an arcuate shaped body such that when the tissue acquisition members are in the retracted position, said tissue acquisition members form a substantially continuous circular disc assembly at the distal portion of said tissue acquisition shaft adjacent said shear plate.

10. A surgical instrument comprising:
    an elongated shaft defining a central axis and having a distal end portion configured to operably support a circular staple cartridge therein;
    a tissue acquisition shaft rotatably supported within said elongated shaft and having a distal portion that protrudes distally beyond the distal end portion of the elongated shaft;
    at least one tissue acquisition member pivotally attached to said distal portion of the tissue acquisition shaft such that said at least one tissue acquisition member is selectively pivotable about a corresponding acquisition axis that is substantially parallel to said central axis from a retracted position to deployed positions upon application of a deployment motion thereto; and
    a deployment member operably supported within said elongated shaft and operably interfacing with each said at least one tissue acquisition member, said deployment member configured to receive said deployment actuation motion to cause said at least one tissue acquisition member to move between said retracted and deployed positions.

11. The surgical instrument of claim 10 wherein said deployment member comprises a deployment shaft extending through said elongated shaft and being selectively rotatably movable relative thereto, said deployment shaft in meshing engagement with each of said tissue acquisition members such that rotation of said deployment shaft in one direction about the central axis causes said tissue acquisition members to pivot from said retracted position to a deployed position and rotation of said deployment shaft in an opposite direction about said central axis causes said tissue acquisition members to pivot from said deployed position to said retracted position.

12. A surgical instrument comprising:
- an elongated shaft defining a central axis and having a distal end portion configured to operably support a circular staple cartridge therein;
- a tissue acquisition shaft rotatably supported within said elongated shaft and having a distal portion that protrudes distally beyond the distal end portion of the elongated shaft;
- at least one tissue acquisition member pivotally attached to said distal portion of the tissue acquisition shaft such that said at least one tissue acquisition member is selectively pivotable about a corresponding acquisition axis that is substantially parallel to said central axis from a retracted position to deployed positions upon application of a deployment motion thereto; and
- at least one tissue acquisition pin protruding radially from said distal portion of said tissue acquisition shaft and including a distal end that is configured to impale tissue.

13. A surgical instrument comprising:
- an elongated shaft defining a central axis and having a distal end portion configured to operably support a circular staple cartridge therein;
- a tissue acquisition shaft rotatably supported within said elongated shaft and having a distal portion that protrudes distally beyond the distal end portion of the elongated shaft; and
- at least one tissue acquisition member pivotally attached to said distal portion of the tissue acquisition shaft such that said at least one tissue acquisition member is selectively pivotable about a corresponding acquisition axis that is substantially parallel to said central axis from a retracted position to deployed positions upon application of a deployment motion thereto and wherein each one of said at least one tissue acquisition members has a tissue-piercing tip.

14. A surgical instrument comprising:
- an elongated shaft defining a central axis and having a distal end portion configured to operably support a circular staple cartridge therein;
- a tissue acquisition shaft rotatably supported within said elongated shaft and having a distal portion that protrudes distally beyond the distal end portion of the elongated shaft; and
- at least one tissue acquisition member pivotally attached to said distal portion of the tissue acquisition shaft such that said at least one tissue acquisition member is selectively pivotable about a corresponding acquisition axis that is substantially parallel to said central axis from a retracted position to deployed positions upon application of a deployment motion thereto and wherein each said at least one tissue acquisition member has a tissue cutting edge formed thereon.

15. The surgical instrument of claim 14 further comprising a shear plate attached to said distal portion of said tissue acquisition shaft and cooperating with said cutting edge of each said tissue acquisition member to shear tissue drawn therebetween.

16. A surgical instrument comprising:
- an elongated shaft defining a central axis and having a distal end portion configured to operably support a circular staple cartridge therein;
- a tissue acquisition shaft rotatably supported within said elongated shaft and having a distal portion that protrudes distally beyond the distal end portion of the elongated shaft;
- a shear plate attached to said distal portion of said tissue acquisition shaft; and
- four tissue acquisition members pivotally attached to said distal portion of the tissue acquisition shaft such that each said tissue acquisition member is selectively pivotable about a corresponding acquisition axis that is substantially parallel to said central axis from a retracted position to deployed positions upon application of a deployment motion thereto, each said tissue acquisition member including an arcuate shaped body such that when the tissue acquisition members are in the retracted position, said tissue acquisition members form a substantially continuous circular disc assembly at the distal portion of said tissue acquisition shaft adjacent said shear plate and wherein each said tissue acquisition member has a tissue cutting edge formed thereon cooperating with said shear plate to shear tissue drawn therebetween.

* * * * *